United States Patent
Suzumura et al.

(10) Patent No.: US 12,428,454 B2
(45) Date of Patent: Sep. 30, 2025

(54) WATER-ABSORBING AND QUICK-DRYING PROPERTY-IMPARTING AGENT, AND METHOD FOR IMPARTING WATER-ABSORBING AND QUICK-DRYING PROPERTIES

(71) Applicant: Spiber Inc., Tsuruoka (JP)

(72) Inventors: Hiroaki Suzumura, Tsuruoka (JP); Yui Hirose, Tsuruoka (JP)

(73) Assignee: Spiber Inc., Tsuruoka (JP)

( * ) Notice: Subject to any disclaimer, the term of this patent is extended or adjusted under 35 U.S.C. 154(b) by 710 days.

(21) Appl. No.: 17/617,566

(22) PCT Filed: Jun. 9, 2020

(86) PCT No.: PCT/JP2020/022742
§ 371 (c)(1),
(2) Date: Dec. 8, 2021

(87) PCT Pub. No.: WO2020/250904
PCT Pub. Date: Dec. 17, 2020

(65) Prior Publication Data
US 2022/0235100 A1      Jul. 28, 2022

(30) Foreign Application Priority Data
Jun. 11, 2019   (JP) .................. 2019-109042

(51) Int. Cl.
| | |
|---|---|
| *C07K 14/435* | (2006.01) |
| *C08J 7/04* | (2020.01) |
| *C08J 7/056* | (2020.01) |
| *C09D 5/00* | (2006.01) |
| *C09D 7/40* | (2018.01) |
| *C09D 189/00* | (2006.01) |
| *D01F 4/02* | (2006.01) |
| *D06M 15/15* | (2006.01) |

(52) U.S. Cl.
CPC ....... *C07K 14/43518* (2013.01); *C08J 7/0427* (2020.01); *C08J 7/056* (2020.01); *C09D 5/00* (2013.01); *C09D 7/70* (2018.01); *C09D 189/00* (2013.01); *D01F 4/02* (2013.01); *D06M 15/15* (2013.01); *C08J 2489/00* (2013.01)

(58) Field of Classification Search
CPC ...... C07K 14/43518; C09D 7/70; C09D 5/00; C09D 189/00; C08J 7/0427; C08J 7/056; C08J 2489/00; D01F 4/02; D06M 15/15
See application file for complete search history.

(56) References Cited

U.S. PATENT DOCUMENTS

| | | | |
|---|---|---|---|
| 2018/0132487 A1* | 5/2018 | Kormann | ............... A01N 63/16 |
| 2019/0135880 A1 | 5/2019 | Morita et al. | |
| 2020/0031887 A1 | 1/2020 | Sugahara et al. | |
| 2020/0207817 A1 | 7/2020 | Morita et al. | |
| 2024/0083955 A1 | 3/2024 | Sugahara et al. | |

FOREIGN PATENT DOCUMENTS

| | | |
|---|---|---|
| CN | 108623759 A | 10/2018 |
| EP | 4039857 A1 | 8/2022 |
| JP | H06-330449 A | 11/1994 |
| JP | H06-330461 A | 11/1994 |
| JP | H07-279053 A | 10/1995 |
| JP | H07-292306 A | 11/1995 |
| JP | H07-310019 A | 11/1995 |
| JP | 10219568 A  * | 8/1998 |
| JP | 3213540 U | 11/2017 |
| JP | 6337252 B1 | 6/2018 |
| WO | 2008083908 A1 † | 7/2008 |
| WO | 2018/163758 A1 | 9/2018 |
| WO | 2019/022163 A1 | 1/2019 |
| WO | 2019/066053 A1 | 4/2019 |

OTHER PUBLICATIONS

Huemmerich et al., "Primary Structure Elements of Spider Dragline Silks and Their Contribution to Protein Solubility", Biochemistry, 43: 13604-13612 (2004).
Third Party Observations filed in European Patent Application No. 20822137.4 dated Jan. 20, 2023.
International Preliminary Report on Patentability and Written Opinion issued in corresponding International Patent Application No. PCT/JP2020/022742 dated Dec. 23, 2021.
Extended European Search Report issued in counterpart European Patent Application No. 20822137.4 dated Jun. 13, 2023.
International Search Report issued in corresponding International Patent Application No. PCT/JP2020/022742 dated Aug. 11, 2020.

\* cited by examiner
† cited by third party

*Primary Examiner* — Anthony J Green
(74) *Attorney, Agent, or Firm* — Studebaker Brackett PLLC

(57) ABSTRACT

Provided is a water-absorbing and quick-drying property-imparting agent capable of easily imparting water-absorbing and quick-drying properties to various materials or articles in a simple process, and a method capable of easily imparting water-absorbing and quick-drying properties to predetermined materials or articles.
A water-absorbing and quick-drying property-imparting agent containing modified fibroin as an active ingredient, and a method for imparting water-absorbing and quick-drying properties to an article, the method including a step of incorporating modified fibroin into the article.

14 Claims, 5 Drawing Sheets
Specification includes a Sequence Listing.

WATER-ABSORBING AND QUICK-DRYING PROPERTY-IMPARTING AGENT, AND METHOD FOR IMPARTING WATER-ABSORBING AND QUICK-DRYING PROPERTIES

SEQUENCE LISTING SUBMISSION VIA EFS-WEB

A computer readable text file, entitled "SequenceListing.txt" created on Nov. 25, 2021 with a file size of 249,751 bytes contains the sequence listing for this application and is hereby incorporated by reference in its entirety.

TECHNICAL FIELD

The present invention relates to a water-absorbing and quick-drying property-imparting agent, and a method for imparting water-absorbing and quick-drying properties.

BACKGROUND ART

In general, clothing such as underwear, innerwear, and sportswear, and bedclothes and the like are required to have so-called water-absorbing and quick-drying properties such as absorbing sweat well and drying quickly. Therefore, many underwear, bedclothes, and the like are produced using cotton spun yarns having relatively high hygroscopic properties.

Although cotton has high water-absorbing properties, it is difficult to say that cotton has sufficient quick-drying properties because absorbed moisture evaporates slowly. In addition, in sportswear and the like, polyurethane fibers and polyester fibers are often used because followability to movement of a human body and stretchability are emphasized, but these synthetic fibers are inferior in water-absorbing properties.

Under such circumstances, various techniques for improving water-absorbing and quick-drying properties of various fibers, fabrics, and the like have been proposed. For example, Patent Literature 1 discloses a water-absorptive quick-drying spun yarn composed of a false-twisted spun yarn including a core made of polyester fibers having a heteromorphic cross section and a sheath made of short fibers including cotton fibers, the core being in a non-twisted state and the sheath being in a bound state.

CITATION LIST

Patent Literature

Patent Literature 1: JU 3213540

SUMMARY OF INVENTION

Technical Problem

For example, as in the water-absorptive quick-drying spun yarn described in Patent Literature 1, the water-absorbing and quick-drying properties of conventional fibers, fabrics, and the like are achieved by using fibers or the like artificially imparted with a special structure. Therefore, the conventional water-absorptive quick-drying fibers and water-absorptive quick-drying fabrics inevitably require complicated production processes.

An object of the present invention is to provide a water-absorbing and quick-drying property-imparting agent capable of easily imparting water-absorbing and quick-drying properties to various materials or articles in a simple process, and a method capable of easily imparting water-absorbing and quick-drying properties to predetermined materials or articles.

Solution to Problem

The present inventors have found that modified fibroin has excellent water-absorbing and quick-drying properties. The present invention is based on this novel finding.

The present invention relates to, for example, the following inventions.

[1]
A water-absorbing and quick-drying property-imparting agent containing modified fibroin as an active ingredient.

[2]
The water-absorbing and quick-drying property-imparting agent according to [1], wherein the modified fibroin contains modified fibroin having an average value of hydropathy indices (average hydropathy index (HI)) of 0 or less.

[3]
The water-absorbing and quick-drying property-imparting agent according to [1] or [2], wherein the modified fibroin contains modified spider silk fibroin.

[4]
The water-absorbing and quick-drying property-imparting agent according to any one of [1] to [3], wherein the water-absorbing and quick-drying property-imparting agent is in the form of a fiber.

[5]
A method of imparting water-absorbing and quick-drying properties to an article, the method including:
a step of incorporating modified fibroin into the article.

Advantageous Effects of Invention

According to the present invention, it is possible to provide a water-absorbing and quick-drying property-imparting agent capable of easily imparting water-absorbing and quick-drying properties to various materials or articles in a simple process, and a method capable of easily imparting water-absorbing and quick-drying properties to predetermined materials or articles.

According to the present invention, for example, by mixing the water-absorbing and quick-drying property-imparting agent according to the present invention with a material having biodegradability, water-absorbing and quick-drying properties can be imparted without impairing biodegradability. According to the present invention, by adjusting the amount of modified fibroin (active ingredient) contained in a predetermined article, the degree of water-absorbing and quick-drying properties of the article can also be adjusted.

DESCRIPTION OF EMBODIMENTS

Figure 1:
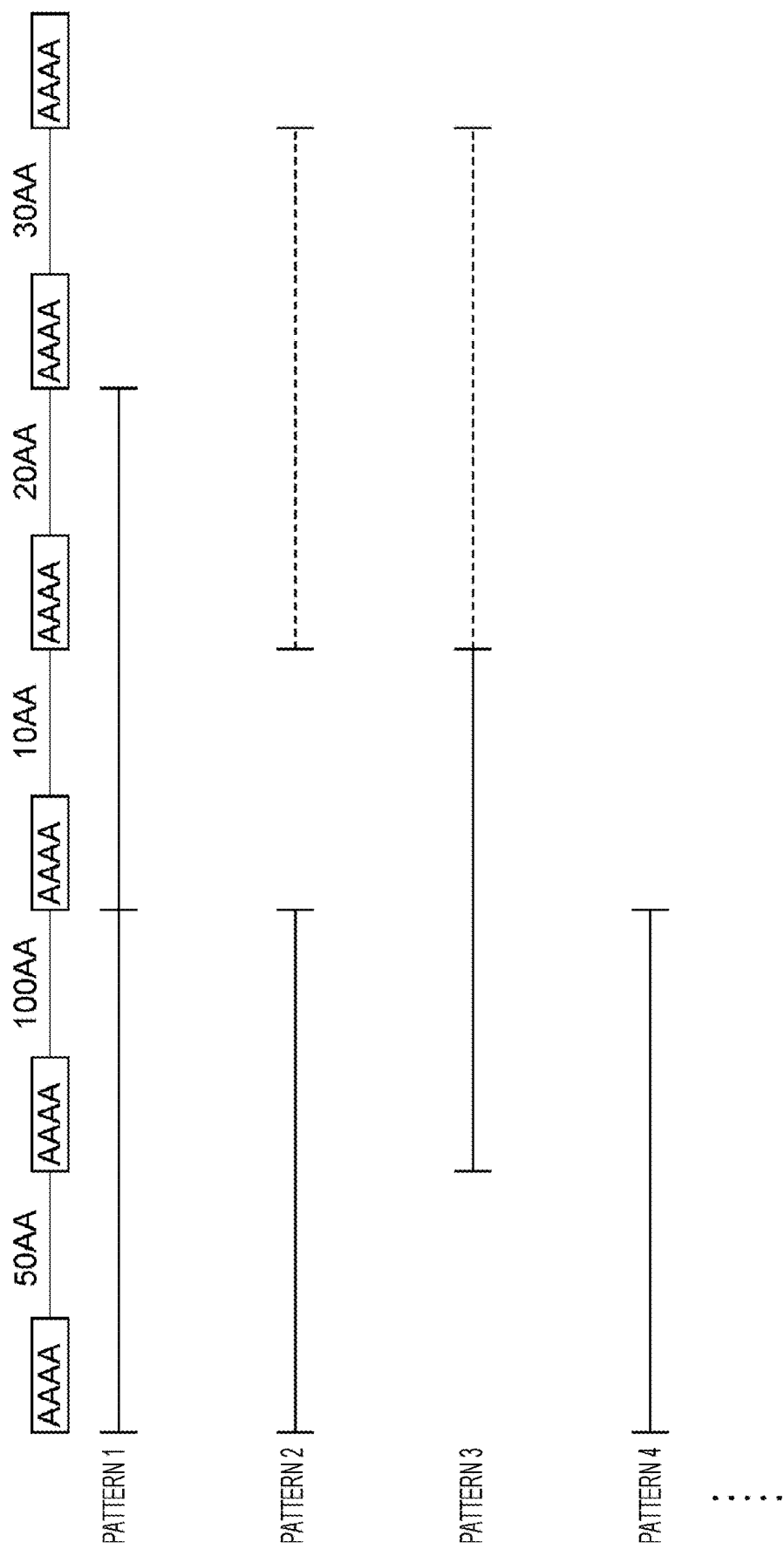
FIG. 1 is a schematic diagram illustrating an example of a domain sequence of modified fibroin.

Hereinafter, embodiments of the present invention will be described in detail. However, the present invention is not limited to the following embodiments.

[Water-Absorbing and Quick-Drying Property-Imparting Agent]

The water-absorbing and quick-drying property-imparting agent according to the present embodiment contains modified fibroin as an active ingredient. The water-absorbing and quick-drying properties refer to a property of absorbing moisture such as sweat and quickly drying. In the present specification, the moisture may be liquid water or gaseous water. That is, in the present specification, water absorption includes moisture absorption. The water-absorbing and quick-drying property-imparting agent according to the present embodiment utilizes the property of modified fibroin excellent in water-absorbing and quick-drying properties.

(Modified Fibroin)

The modified fibroin according to the present embodiment is a protein including a domain sequence represented by Formula 1: [(A)$_n$ motif-REP]$_m$ or Formula 2: [(A)$_n$ motif-REP]$_m$-(A)$_n$ motif. An amino acid sequence (N-terminal sequence and C-terminal sequence) may be further added to either or both of the N-terminal side and the C-terminal side of the domain sequence of the modified fibroin. The N-terminal sequence and the C-terminal sequence, although not limited thereto, are typically regions that do not have repetitions of amino acid motifs characteristic of fibroin and consist of amino acids of about 100 residues.

The term "modified fibroin" in the present specification refers to artificially produced fibroin (artificial fibroin). The modified fibroin may be fibroin in which a domain sequence is different from an amino acid sequence of naturally derived fibroin or may be fibroin in which a domain sequence is the same as an amino acid sequence of naturally derived fibroin. The term "naturally derived fibroin" as used herein is also a protein including a domain sequence represented by Formula 1: [(A)$_n$ motif-REP]$_m$ or Formula 2: [(A)$_n$ motif-REP]$_m$-(A)$_n$ motif.

The "modified fibroin" may be fibroin obtained by using an amino acid sequence of naturally derived fibroin as it is, fibroin in which an amino acid sequence is modified based on an amino acid sequence of naturally derived fibroin (for example, fibroin in which an amino acid sequence is modified by modifying a cloned gene sequence of naturally derived fibroin), or fibroin artificially designed and synthesized independently of naturally derived fibroin (for example, fibroin having a desired amino acid sequence by chemically synthesizing a nucleic acid encoding a designed amino acid sequence).

The term "domain sequence" in the present specification is an amino acid sequence that produces a crystal region (typically, corresponding to the (A)$_n$ motif of the amino acid sequence) and an amorphous region (typically, corresponding to REP of the amino acid sequence) specific to fibroin, and means an amino acid sequence represented by Formula 1: [(A)$_n$ motif-REP]$_m$ or Formula 2: [(A)$_n$ motif-REP]$_m$-(A)$_n$ motif. Here, the (A)$_n$ motif represents an amino acid sequence mainly composed of alanine residues, and the number of amino acid residues therein is 2 to 27. The number of the amino acid residues in the (A)$_n$ motif may be an integer of 2 to 20, 4 to 27, 4 to 20, 8 to 20, 10 to 20, 4 to 16, 8 to 16, or 10 to 16. In addition, the proportion of the number of alanine residues in the total number of amino acid residues in the (A)$_n$ motif may be 40% or more, or may also be 60% or more, 70% or more, 80% or more, 83% or more, 85% or more, 86% or more, 90% or more, 95% or more, or 100% (meaning that the (A)$_n$ motif only consists of alanine residues). At least seven of a plurality of (A)$_n$ motifs in the domain sequence may consist of only alanine residues. The REP represents an amino acid sequence consisting of 2 to 200 amino acid residues. The REP may be an amino acid sequence consisting of 10 to 200 amino acid residues. m represents an integer of 2 to 300, and may be an integer of 10 to 300. A plurality of (A)$_n$ motifs may be the same amino acid sequences or different amino acid sequences. A plurality of REPs may be the same amino acid sequences or different amino acid sequences.

The modified fibroin according to the present embodiment can be obtained by, for example, performing modification of an amino acid sequence corresponding to substitution, deletion, insertion, and/or addition of one or a plurality of amino acid residues with respect to a cloned gene sequence of naturally derived fibroin. Substitution, deletion, insertion, and/or addition of the amino acid residues can be performed by methods well known to those skilled in the art, such as site-directed mutagenesis. Specifically, the modification may be performed in accordance with a method described in literatures such as Nucleic Acid Res. 10, 6487 (1982), and Methods in Enzymology, 100, 448 (1983).

The naturally derived fibroin is a protein including a domain sequence represented by Formula 1: [(A)$_n$ motif-REP]$_m$ or Formula 2: [(A)$_n$ motif-REP]$_m$-(A)$_n$ motif, and a specific example thereof can include fibroin produced by insects or spiders.

Examples of the fibroin produced by insects can include silk proteins produced by silkworms such as *Bombyx mori, Bombyx mandarina, Antheraea yamamai, Anteraea pernyi, Eriogyna pyretorum, Pilosamia Cynthia ricini, Samia cynthia, Caligura japonica, Antheraea mylitta*, and *Antheraea assama* and a hornet silk protein secreted by larvae of *Vespasimillima xanthoptera*.

More specific examples of the fibroin produced by insects can include the silkworm fibroin L chain (GenBank Accession Nos. M76430 (nucleotide sequence) and AAA27840.1 (amino acid sequence)).

Examples of the fibroin produced by spiders can include spider silk proteins produced by spiders belonging to the order Araneae. More specific examples thereof can include spider silk proteins produced by spiders belonging to the genus *Araneus*, such as *Araneus ventricosus, Araneus diadematus, Araneus pinguis, Araneus pentagrammicus*, and *Araneus nojimai*, spiders belonging to the genus *Neoscona*, such as *Neoscona scylla, Neoscona nautica, Neoscona adianta*, and *Neoscona scylloides*, spiders belonging to the genus *Pronus*, such as *Pronous minutus*, spiders belonging to the genus *Cyrtarachne*, such as *Cyrtarachne bufo* and *Cyrtarachne inaequalis*, spiders belonging to the genus *Gasteracantha*, such as *Gasteracantha kuhlii* and *Gasteracantha mammosa*, spiders belonging to the genus *Ordgarius*, such as *Ordgarius hobsoni* and *Ordgarius sexspinosus*, spiders belonging to the genus *Argiope*, such as *Argiope amoena, Argiope minuta*, and *Argiope bruennichi*, spiders belonging to the genus *Arachnura*, such as *Arachnura logio*, spiders belonging to the genus *Acusilas*, such as *Acusilas coccineus*, spiders belonging to the genus *Cytophora*, such as *Cyrtophora moluccensis, Cyrtophora exanthematica*, and *Cyrtophora unicolor*, spiders belonging to the genus *Poltys*, such as *Poltys illepidus*, spiders belonging to the genus

*Cyclosa*, such as *Cyclosa octotuberculata, Cyclosa sedeculata, Cyclosa vallata*, and *Cyclosa atrata*, and spiders belonging to the genus *Chorizopes*, such as *Chorizopes nipponicus*, and spider silk proteins produced by spiders belonging to the family Tetragnathidae, such as spiders belonging to the genus *Tetragnatha*, such as *Tetragnatha praedonia, Tetragnatha maxillosa, Tetragnatha extensa*, and *Tetragnatha squamata*, spiders belonging to the genus *Leucauge*, such as *Leucauge magnifica, Leucauge blanda*, and *Leucauge subblanda*, spiders belonging to the genus *Nephila*, such as *Nephila clavata* and *Nephila pilipes*, spiders belonging to the genus *Menosira*, such as *Menosira ornata*, spiders belonging to the genus *Dyschiriognatha*, such as *Dyschiriognatha tenera*, spiders belonging to the genus *Latrodectus*, such as *Latrodectus mactans, Latrodectus hasseltii, Latrodectus geometricus*, and *Latrodectus tredecimguttatus*, and spiders belonging to the genus *Euprosthenops*. Examples of the spider silk protein can include dragline silk proteins such as MaSps (MaSp1 and MaSp2) and ADFs (ADF3 and ADF4), MiSps (MiSp1 and MiSp2), AcSp, PySp, and Flag.

More specific examples of the spider silk protein produced by spiders include fibroin-3 (adf-3) [derived from *Araneus diadematus*] (GenBank Accession No. AAC47010 (amino acid sequence), U47855 (nucleotide sequence)), fibroin-4 (adf-4) [derived from *Araneus diadematus*] (GenBank Accession No. AAC47011 (amino acid sequence), U47856 (nucleotide sequence)), dragline silk protein spidroin 1 [derived from *Nephila clavipes*] (GenBank Accession No. AAC04504 (amino acid sequence), U37520 (nucleotide sequence)), major ampullate spidroin 1 [derived from *Latrodectus hesperus*] (GenBank Accession No. ABR68856 (amino acid sequence), EF595246 (nucleotide sequence)), dragline silk protein spidroin 2 [derived from *Nephila clavata*] (GenBank Accession No. AAL32472 (amino acid sequence), AF441245 (nucleotide sequence)), major ampullate spidroin 1 [derived from *Euprosthenops australis*] (GenBank Accession No. CAJ00428 (amino acid sequence), AJ973155 (nucleotide sequence)), and major ampullate spidroin 2 [*Euprosthenops australis*] (GenBank Accession No. CAM32249.1 (amino acid sequence), AM490169 (nucleotide sequence)), minor ampullate silk protein 1 [*Nephila clavipes*] (GenBank Accession No. AAC14589.1 (amino acid sequence)), minor ampullate silk protein 2 [*Nephila clavipes*] (GenBank Accession No. AAC14591.1 (amino acid sequence)), and minor ampullate spidroin-like protein [*Nephilengys cruentata*] (GenBank Accession No. ABR37278.1 (amino acid sequence).

More specific examples of the naturally derived fibroin can include fibroin whose sequence information is registered in NCBI GenBank. For example, sequences thereof may be confirmed by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

The modified fibroin according to the present embodiment may be modified silk fibroin (in which an amino acid sequence of a silk protein produced by silkworm is modified), or may be modified spider silk fibroin (in which an amino acid sequence of a spider silk protein produced by spiders is modified).

Specific examples of the modified fibroin can include modified fibroin derived from a major dragline silk protein produced in a major ampullate gland of a spider (first modified fibroin), modified fibroin having a domain sequence in which the content of glycine residues is reduced (second modified fibroin), modified fibroin having a domain sequence in which the content of an $(A)_n$ motif is reduced (third modified fibroin), modified fibroin in which the content of glycine residues and the content of an $(A)_n$ motif are reduced (fourth modified fibroin), modified fibroin having a domain sequence including a region locally having a high hydropathy index (fifth modified fibroin), and modified fibroin having a domain sequence in which the content of glutamine residues is reduced (sixth modified fibroin).

An example of the first modified fibroin can include a protein including a domain sequence represented by Formula 1: $[(A)_n \text{ motif-REP}]_m$. In the first modified fibroin, the number of amino acid residues in the $(A)_n$ motif is preferably an integer of 3 to 20, more preferably an integer of 4 to 20, still more preferably an integer of 8 to 20, even still more preferably an integer of 10 to 20, still further preferably an integer of 4 to 16, particularly preferably an integer of 8 to 16, and most preferably an integer of 10 to 16. In the first modified fibroin, the number of amino acid residues constituting REP in Formula 1 is preferably 10 to 200 residues, more preferably 10 to 150 residues, and still more preferably 20 to 100 residues, and still even more preferably 20 to 75 residues. In the first modified fibroin, the total number of glycine residues, serine residues, and alanine residues included in the amino acid sequence represented by Formula 1: $[(A)_n \text{ motif-REP}]$, is preferably 40% or more, more preferably 60% or more, and still more preferably 70% or more, relative to the total number of amino acid residues.

The first modified fibroin may be a polypeptide including an amino acid sequence unit represented by Formula 1: $[(A)_n \text{ motif-REP}]_m$, and including a C-terminal sequence which is an amino acid sequence set forth in any one of SEQ ID NO: 1 to 3 or a C-terminal sequence which is an amino acid sequence having 90% or more homology with the amino acid sequence set forth in any one of SEQ ID NO: 1 to 3.

The amino acid sequence set forth in SEQ ID NO: 1 is identical to an amino acid sequence consisting of 50 amino acid residues of the C-terminal of an amino acid sequence of ADF3 (GI: 1263287, NCBI). The amino acid sequence set forth in SEQ ID NO: 2 is identical to an amino acid sequence set forth in SEQ ID NO: 1 in which 20 amino acid residues have been removed from the C-terminal. The amino acid sequence set forth in SEQ ID NO: 3 is identical to an amino acid sequence set forth in SEQ ID NO: 1 in which 29 amino acid residues have been removed from the C-terminal.

A specific example of the first modified fibroin can include modified fibroin including (1-i) the amino acid sequence set forth in SEQ ID NO: 4 (recombinant spider silk protein ADF3KaiLargeNRSH1), or (1-ii) an amino acid sequence having 90% or more sequence identity with the amino acid sequence set forth in SEQ ID NO: 4. The sequence identity is preferably 95% or more.

The amino acid sequence set forth in SEQ ID NO: 4 is obtained by the following mutation: in an amino acid sequence of ADF3 in which an amino acid sequence (SEQ ID NO: 5) consisting of a start codon, a His 10-tag, and an HRV3C protease (Human rhinovirus 3C protease) recognition site is added to the N-terminal, the 1st to 13th repetitive regions are about doubled and the translation ends at the 1154th amino acid residue. The C-terminal amino acid sequence of the amino acid sequence set forth in SEQ ID NO: 4 is identical to the amino acid sequence set forth in SEQ ID NO: 3.

The modified fibroin of (1-i) may consist of the amino acid sequence set forth in SEQ ID NO: 4.

The domain sequence of the second modified fibroin has an amino acid sequence in which the content of glycine residues is reduced, as compared with naturally derived fibroin. It can be said that the second modified fibroin has an amino acid sequence corresponding to an amino acid sequence in which at least one or a plurality of glycine residues in REP are substituted with another amino acid residue, as compared with naturally derived fibroin.

The domain sequence of the second modified fibroin may have an amino acid sequence corresponding to an amino acid sequence in which one glycine residue in at least one or the plurality of motif sequences is substituted with another amino acid residue, in at least one motif sequence selected from GGX and GPGXX (where G represents a glycine residue, P represents a proline residue, and X represents an amino acid residue other than glycine) in REP, as compared with naturally derived fibroin.

In the second modified fibroin, the proportion of the motif sequence in which the glycine residue has been substituted with another amino acid residue may be 10% or more relative to the entire motif sequence.

The second modified fibroin includes a domain sequence represented by Formula 1: $[(A)_n\ \text{motif-REP}]_m$, and may have an amino acid sequence in which z/w is 30% or more, 40% or more, 50% or more, or 50.9% or more in a case where the total number of amino acid residues in the amino acid sequence consisting of XGX (where X represents an amino acid residue other than glycine) included in all REPs in a sequence excluding the sequence from the $(A)_n$ motif located at the most C-terminal side to the C-terminal of the domain sequence from the domain sequence is defined as z, and the total number of amino acid residues in the sequence excluding the sequence from the $(A)_n$ motif located at the most C-terminal side to the C-terminal of the domain sequence from the domain sequence is defined as w. The number of alanine residues with respect to the total number of amino acid residues in the $(A)_n$ motif is 83% or more, preferably 86% or more, more preferably 90% or more, still more preferably 95% or more, and even still more preferably 100% (meaning that the $(A)_n$ motif consists of only alanine residues).

The second modified fibroin is preferably one in which the content ratio of the amino acid sequence consisting of XGX is increased by substituting one glycine residue of the GGX motif with another amino acid residue. In the second modified fibroin, the content ratio of the amino acid sequence consisting of GGX in the domain sequence is preferably 30% or less, more preferably 20% or less, still more preferably 10% or less, even still more preferably 6% or less, still further preferably 4% or less, and particularly preferably 2% or less. The content ratio of the amino acid sequence consisting of GGX in the domain sequence can be calculated by the same method as the calculation method of the content ratio (z/w) of the amino acid sequence consisting of XGX described below.

The method of calculating z/w will be described in more detail. First, the amino acid sequence consisting of XGX is extracted from all REPs included in a sequence excluding the sequence from the $(A)_n$ motif located at the most C-terminal side to the C-terminal of the domain sequence from the domain sequence in the fibroin including a domain sequence represented by Formula 1: $[(A)_n\ \text{motif-REP}]_m$ (modified fibroin or naturally derived fibroin). The total number of amino acid residues constituting XGX is z. For example, in a case where 50 amino acid sequences consisting of XGX are extracted (there is no overlap), z is 50×3=150. Also, for example, in a case where X (central X) included in two XGXs exists as in a case of the amino acid sequence consisting of XGXGX, z is calculated by subtracting the overlapping portion (in a case of XGXGX, it is 5 amino acid residues). w is the total number of amino acid residues included in a sequence excluding the sequence from the $(A)_n$ motif located at the most C-terminal side to the C-terminal of the domain sequence from the domain sequence. For example, in a case of the domain sequence shown in FIG. 1, w is 4+50+4+100+4+10+4+20+4+30=230 (excluding the $(A)_n$ motif located at the most C-terminal side). Next, z/w (%) can be calculated by dividing z by w.

Figure 2:
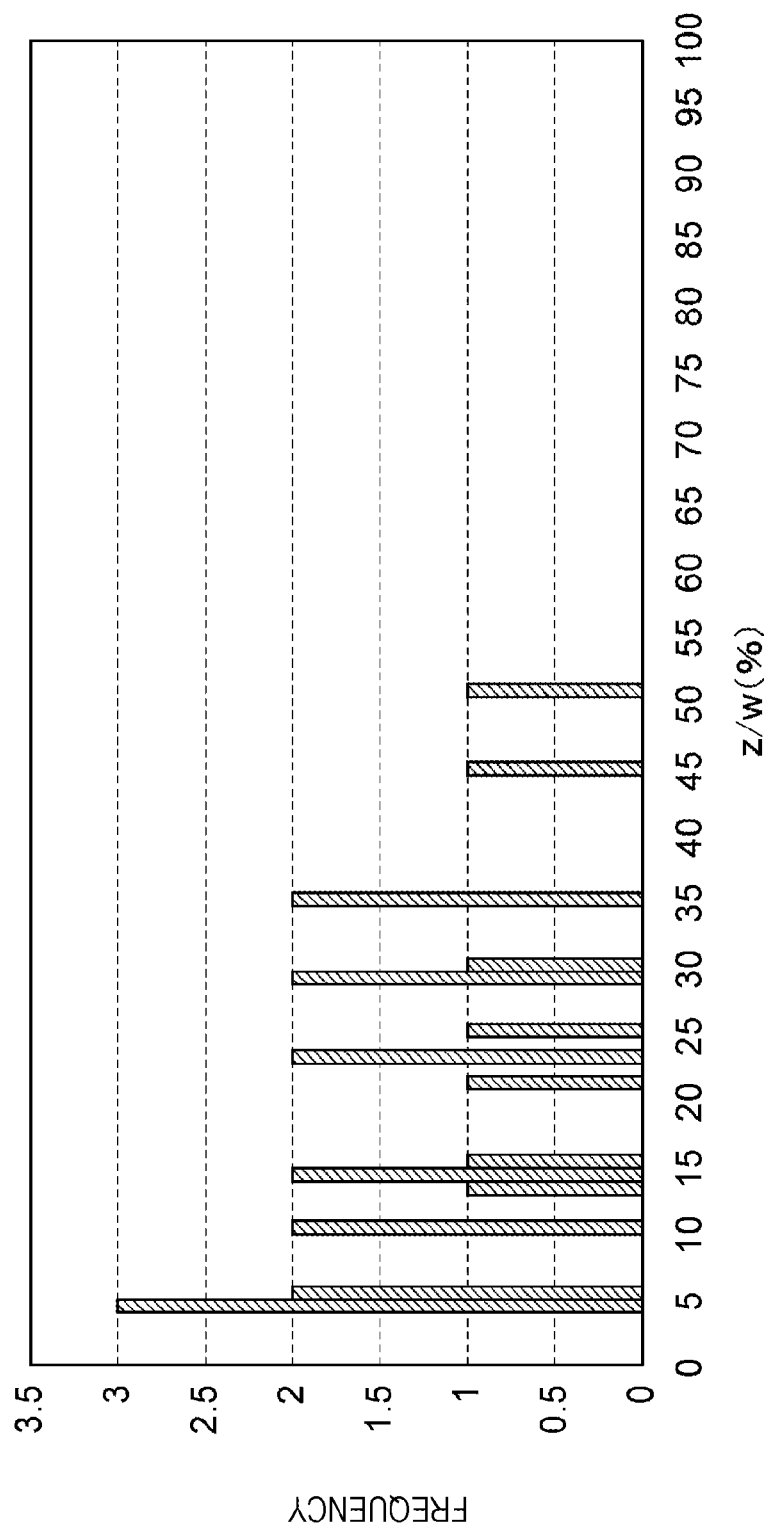
FIG. 2 is a graph illustrating a distribution of values of z/w (%) in naturally derived fibroin.

Here, z/w in naturally derived fibroin will be described. First, as described above, 663 types of fibroins (415 types of fibroins derived from spiders among them) were extracted by confirming fibroins with amino acid sequence information registered in NCBI GenBank by an exemplified method. The values of z/w were calculated by the calculation method described above, from amino acid sequences of naturally derived fibroins which include a domain sequence represented by Formula 1: $[(A)_n\ \text{motif-REP}]_m$ and in which the content ratio of the amino acid sequence consisting of GGX in the fibroin is 6% or less, among all the extracted fibroins. The results are shown in FIG. 2. In FIG. 2, the horizontal axis represents z/w (%), and the vertical axis represents a frequency. As is clear from FIG. 2, the values of z/w in naturally derived fibroin are all smaller than 50.9% (the largest value is 50.86%).

In the second modified fibroin, z/w is preferably 50.9% or more, more preferably 56.1% or more, still more preferably 58.7% or more, even still more preferably 70% or more, and still further preferably 80% or more. The upper limit of z/w is not particularly limited, but may be 95% or less, for example.

The second modified fibroin can be obtained by, for example, substituting and modifying at least a part of a nucleotide sequence encoding a glycine residue from a cloned gene sequence of naturally derived fibroin so as to encode another amino acid residue. In this case, one glycine residue in a GGX motif or a GPGXX motif may be selected as the glycine residue to be modified, and substitution may be performed so that z/w is 50.9% or more. In addition, the second modified fibroin can also be obtained by, for example, designing an amino acid sequence satisfying each of the above aspects from the amino acid sequence of naturally derived fibroin, and chemically synthesizing a nucleic acid encoding the designed amino acid sequence. In any case, in addition to the modification corresponding to substitution of a glycine residue in REP with another amino acid residue from the amino acid sequence of naturally derived fibroin, modification of the amino acid sequence corresponding to substitution, deletion, insertion, and/or addition of one or a plurality of amino acid residues may be performed.

The above-described another amino acid residue is not particularly limited as long as it is an amino acid residue other than a glycine residue, but it is preferably a hydrophobic amino acid residue such as a valine (V) residue, a leucine (L) residue, an isoleucine (I) residue, a methionine (M) residue, a proline (P) residue, a phenylalanine (F) residue, or a tryptophan (W) residue, or a hydrophilic amino acid residue such as a glutamine (Q) residue, an asparagine (N) residue, a serine (S) residue, a lysine (K) residue, or a glutamic acid (E) residue, more preferably a valine (V) residue, a leucine (L) residue, an isoleucine (I) residue, a phenylalanine (F) residue, or a glutamine (Q) residue, and still more preferably a glutamine (Q) residue.

A more specific example of the second modified fibroin can include modified fibroin including (2-i) the amino acid sequence set forth in SEQ ID NO: 6 (Met-PRT380), SEQ ID NO: 7 (Met-PRT410), SEQ ID NO: 8 (Met-PRT525), or SEQ ID NO: 9 (Met-PRT799), or (2-ii) an amino acid sequence having 90% or more sequence identity with the amino acid sequence set forth in SEQ ID NO: 6, SEQ ID NO: 7, SEQ ID NO: 8, or SEQ ID NO: 9.

The modified fibroin of (2-i) will be described. The amino acid sequence set forth in SEQ ID NO: 6 is obtained by substituting all GGXs with GQX in REP of the amino acid sequence set forth in SEQ ID NO: 10 (Met-PRT313) corresponding to naturally derived fibroin. The amino acid sequence set forth in SEQ ID NO: 7 is obtained by deleting every other two $(A)_n$ motifs from the N-terminal side to the C-terminal side from the amino acid sequence set forth in SEQ ID NO: 6 and further inserting one [$(A)_n$ motif-REP] before the C-terminal sequence. The amino acid sequence set forth in SEQ ID NO: 8 is obtained by inserting two alanine residues on the C-terminal side of each $(A)_n$ motif of the amino acid sequence set forth in SEQ ID NO: 7 and further substituting a part of glutamine (Q) residues with a serine (S) residue to delete a part of amino acids on the C-terminal side so as to be almost the same as the molecular weight of SEQ ID NO: 7. The amino acid sequence set forth in SEQ ID NO: 9 is obtained by adding a predetermined hinge sequence and a His tag sequence to the C-terminal of a sequence obtained by repeating a region of 20 domain sequences (where several amino acid residues on the C-terminal side of the region are substituted) present in the amino acid sequence set forth in SEQ ID NO: 7 four times.

The value of z/w in the amino acid sequence set forth in SEQ ID NO: 10 (corresponding to naturally derived fibroin) is 46.8%. The values of z/w in the amino acid sequence set forth in SEQ ID NO: 6, the amino acid sequence set forth in SEQ ID NO: 7, the amino acid sequence set forth in SEQ ID NO: 8, and the amino acid sequence set forth in SEQ ID NO: 9 are 58.7%, 70.1%, 66.1%, and 70.0%, respectively. In addition, the values of x/y in the amino acid sequences set forth in SEQ ID NO: 10, SEQ ID NO: 6, SEQ ID NO: 7, SEQ ID NO: 8, and SEQ ID NO: 9 at a Giza ratio (described below) of 1:1.8 to 11.3 are 15.0%, 15.0%, 93.4%, 92.7%, and 89.8%, respectively.

The modified fibroin of (2-i) may consist of the amino acid sequence set forth in SEQ ID NO: 6, SEQ ID NO: 7, SEQ ID NO: 8, or SEQ ID NO: 9.

The modified fibroin of (2-ii) includes an amino acid sequence having 90% or more sequence identity with the amino acid sequence set forth in SEQ ID NO: 6, SEQ ID NO: 7, SEQ ID NO: 8, or SEQ ID NO: 9. The modified fibroin of (2-ii) is also a protein including a domain sequence represented by Formula 1: $[(A)_n$ motif-REP$]_m$. The sequence identity is preferably 95% or more.

It is preferred that the modified fibroin of (2-ii) preferably has 90% or more sequence identity with the amino acid sequence set forth in SEQ ID NO: 6, SEQ ID NO: 7, SEQ ID NO: 8, or SEQ ID NO: 9, and z/w is 50.9% or more in a case where the total number of amino acid residues in the amino acid sequence consisting of XGX (where X represents an amino acid residue other than glycine) included in REP is defined as z, and the total number of amino acid residues of REP in the domain sequence is defined as w.

The second modified fibroin may have a tag sequence at either or both of the N-terminal and the C-terminal. This enables the modified fibroin to be isolated, immobilized, detected, and visualized.

The tag sequence may be, for example, an affinity tag utilizing specific affinity (binding property, affinity) with another molecule. A specific example of the affinity tag includes a histidine tag (His tag). The His tag is a short peptide in which about 4 to 10 histidine residues are arranged and has a property of specifically binding to a metal ion such as nickel. Thus, the His tag can be used for isolation of modified fibroin by chelating metal chromatography. A specific example of the tag sequence can include the amino acid sequence set forth in SEQ ID NO: 11 (amino acid sequence including a His tag sequence and a hinge sequence).

Also, a tag sequence such as glutathione-S-transferase (GST) that specifically binds to glutathione, and a maltose binding protein (MBP) that specifically binds to maltose can also be utilized.

Further, an "epitope tag" utilizing an antigen-antibody reaction can also be utilized. Adding a peptide (epitope) exhibiting antigenicity as a tag sequence allows an antibody against the epitope to be bound. Examples of the epitope tag include an HA (peptide sequence of hemagglutinin of influenza virus) tag, a myc tag, and a FLAG tag. The modified fibroin can easily be purified with high specificity by utilizing an epitope tag.

Moreover, it is possible to use a tag sequence which can be cleaved with a specific protease. The modified fibroin from which the tag sequence has been cleaved can be recovered by treating a protein adsorbed through the tag sequence with protease.

A more specific example of the modified fibroin including a tag sequence can include modified fibroin including (2-iii) the amino acid sequence set forth in SEQ ID NO: 12 (PRT380), SEQ ID NO: 13 (PRT410), SEQ ID NO: 14 (PRT525), or SEQ ID NO: 15 (PRT799), or (2-iv) an amino acid sequence having 90% or more sequence identity with the amino acid sequence set forth in SEQ ID NO: 12, SEQ ID NO: 13, SEQ ID NO: 14, or SEQ ID NO: 15.

Each of the amino acid sequences set forth in SEQ ID NO: 16 (PRT313), SEQ ID NO: 12, SEQ ID NO: 13, SEQ ID NO: 14, and SEQ ID NO: 15 is obtained by adding the amino acid sequence set forth in SEQ ID NO: 11 (including a His tag sequence and a hinge sequence) to the N-terminal of each of the amino acid sequences set forth in SEQ ID NO: 10, SEQ ID NO: 6, SEQ ID NO: 7, SEQ ID NO: 8, and SEQ ID NO: 9.

The modified fibroin of (2-iii) may consist of the amino acid sequence set forth in SEQ ID NO: 12, SEQ ID NO: 13, SEQ ID NO: 14, or SEQ ID NO: 15.

The modified fibroin of (2-iv) includes an amino acid sequence having 90% or more sequence identity with the amino acid sequence set forth in SEQ ID NO: 12, SEQ ID NO: 13, SEQ ID NO: 14, or SEQ ID NO: 15. The modified fibroin of (2-iv) is also a protein including a domain sequence represented by Formula 1: $[(A)_n$ motif-REP$]_m$. The sequence identity is preferably 95% or more.

It is preferred that the modified fibroin of (2-iv) has 90% or more sequence identity with the amino acid sequence set forth in SEQ ID NO: 12, SEQ ID NO: 13, SEQ ID NO: 14, or SEQ ID NO: 15, and z/w is 50.9% or more in a case where the total number of amino acid residues in the amino acid sequence consisting of XGX (where X represents the amino acid residue other than glycine) in REP is defined as z, and the total number of amino acid residues in REP in the domain sequence is defined as w.

The second modified fibroin may include a secretory signal for releasing the protein produced in the recombinant protein production system to the outside of a host. The sequence of the secretory signal can be appropriately set depending on the type of the host.

The domain sequence of the third modified fibroin has an amino acid sequence in which the content of the $(A)_n$ motif is reduced, as compared with naturally derived fibroin. It can be said that the domain sequence of the third modified fibroin has an amino acid sequence corresponding to an amino acid sequence in which at least one or a plurality of $(A)_n$ motifs are deleted, as compared with naturally derived fibroin.

The third modified fibroin may have an amino acid sequence corresponding to an amino acid sequence in which 10 to 40% of the $(A)_n$ motifs are deleted from naturally derived fibroin.

The domain sequence of the third modified fibroin may have an amino acid sequence corresponding to an amino acid sequence in which at least one $(A)_n$ motif of every one to three $(A)_n$ motifs is deleted from the N-terminal side to the C-terminal side, as compared with naturally derived fibroin.

The third modified fibroin may have an amino acid sequence corresponding to an amino acid sequence in which deletion of at least two consecutive $(A)_n$ motifs and deletion of one $(A)_n$ motif are repeated in this order from the N-terminal side to the C-terminal side, as compared with naturally derived fibroin.

The third modified fibroin may have a domain sequence having an amino acid sequence corresponding to an amino acid sequence in which at least $(A)_n$ motif every other two positions is deleted from the N-terminal side to the C-terminal side.

The third modified fibroin includes a domain sequence represented by Formula 1: $[(A)_n$ motif-REP$]_m$, and may have an amino acid sequence in which x/y is 20% or more, 30% or more, 40% or more, or 50% or more in a case where the numbers of amino acid residues in REPs of two adjacent $[(A)_n$ motif-REP] units are sequentially compared from the N-terminal side to the C-terminal side, and the number of amino acid residues in one REP having a smaller number of amino acid residues is defined as 1, the maximum value of the total value of the number of amino acid residues in the two adjacent $[(A)_n$ motif-REP] units where the ratio of the number of amino acid residues in the other REP is 1.8 to 11.3 is defined as x, and the total number of amino acid residues in the domain sequence is defined as y. The number of alanine residues with respect to the total number of amino acid residues in the $(A)_n$ motif is 83% or more, preferably 86% or more, more preferably 90% or more, still more preferably 95% or more, and even still more preferably 100% (meaning that the $(A)_n$ motif consists of only alanine residues).

The method of calculating x/y will be described in more detail with reference to FIG. 1. FIG. 1 shows a domain sequence excluding the N-terminal sequence and the C-terminal sequence from the modified fibroin. The domain sequence has a sequence of $(A)_n$ motif-first REP (50 amino acid residues)-$(A)_n$ motif-second REP (100 amino acid residues)-$(A)_n$ motif-third REP (10 amino acid residues)-$(A)_n$ motif-fourth REP (20 amino acid residues)-$(A)_n$ motif-fifth REP (30 amino acid residues)-$(A)_n$ motif from the N-terminal side (left side).

The two adjacent $[(A)_n$ motif-REP] units are sequentially selected from the N-terminal side to the C-terminal side so as not to overlap. At this time, an unselected $[(A)_n$ motif-REP] unit may exist. FIG. 1 shows a pattern 1 (a comparison between the first REP and the second REP, and a comparison between the third REP and the fourth REP), a pattern 2 (a comparison between the first REP and the second REP, and a comparison between the fourth REP and the fifth REP), a pattern 3 (a comparison between the second REP and the third REP, and a comparison between the fourth REP and the fifth REP), and a pattern 4 (a comparison between the first REP and the second REP). There are other selection methods besides this.

Subsequently, the number of amino acid residues of each REP in the selected two adjacent $[(A)_n$ motif-REP] units is compared for each pattern. The comparison is performed by determining the ratio of the number of amino acid residues of the other REP in a case where one REP having a smaller number of amino acid residues is defined as 1. For example, in a case of comparing the first REP (50 amino acid residues) and the second REP (100 amino acid residues), the ratio of the number of amino acid residues of the second REP is 100/50=2 in a case where the first REP having a smaller number of amino acid residues is defined as 1. Similarly, in a case of comparing the fourth REP (20 amino acid residues) and the fifth REP (30 amino acid residues), the ratio of the number of amino acid residues of the fifth REP is 30/20=1.5 in a case where the fourth REP having a smaller number of amino acid residues is defined as 1.

In FIG. 1, a set of $[(A)_n$ motif-REP] units in which the ratio of the number of amino acid residues of the other REP is 1.8 to 11.3 in a case where one REP having a smaller number of amino acid residues is defined as 1 is indicated by a solid line. In the present specification, the ratio is referred to as a Giza ratio. A set of $[(A)_n$ motif-REP] units in which the ratio of the number of amino acid residues of the other REP is less than 1.8 or more than 11.3 in a case where one REP having a smaller number of amino acid residues is defined as 1 is indicated by a broken line.

In each pattern, the number of all amino acid residues of two adjacent $[(A)_n$ motif-REP] units indicated by solid lines (including not only the number of amino acid residues of REP but also the number of amino acid residues of the (A)n motif) is combined. Then, the total values combined are compared, and the total value of the pattern whose total value is the maximum (the maximum value of the total value) is defined as x. In the example shown in FIG. 1, the total value of the pattern 1 is the maximum.

Then, x/y (%) can be calculated by dividing x by the total number of amino acid residues y of the domain sequence.

In the third modified fibroin, x/y is preferably 50% or more, more preferably 60% or more, still more preferably 65% or more, even still more preferably 70% or more, still further preferably 75% or more, and particularly preferably 80% or more. The upper limit of x/y is not particularly limited, but may be, for example, 100% or less. In a case where the Giza ratio is 1:1.9 to 11.3, x/y is preferably 89.6% or more; in a case where the Giza ratio is 1:1.8 to 3.4, x/y is preferably 77.1% or more; in a case where the Giza ratio is 1:1.9 to 8.4, x/y is preferably 75.9% or more; and in a case where the Giza ratio is 1:1.9 to 4.1, x/y is preferably 64.2% or more.

In a case where the third modified fibroin is modified fibroin in which at least seven of a plurality of $(A)_n$ motifs in the domain sequence consist of only alanine residues, x/y is preferably 46.4% or more, more preferably 50% or more, still more preferably 55% or more, even still more preferably 60% or more, still further preferably 70% or more, and particularly preferably 80% or more. The upper limit of x/y is not particularly limited, but is only required to be 100% or less.

Here, x/y in naturally derived fibroin will be described. First, as described above, 663 types of fibroins (415 types of fibroins derived from spiders among them) were extracted by confirming fibroins with amino acid sequence information registered in NCBI GenBank by an exemplified method. The values of x/y were calculated by the calculation method described above, from amino acid sequences of naturally derived fibroins consisting of a domain sequence represented by Formula 1: $[(A)_n$ motif-REP$]_m$, among all the extracted fibroins. The results in a case where the Giza ratio is 1:1.9 to 4.1 are shown in FIG. 3.

Figure 3:
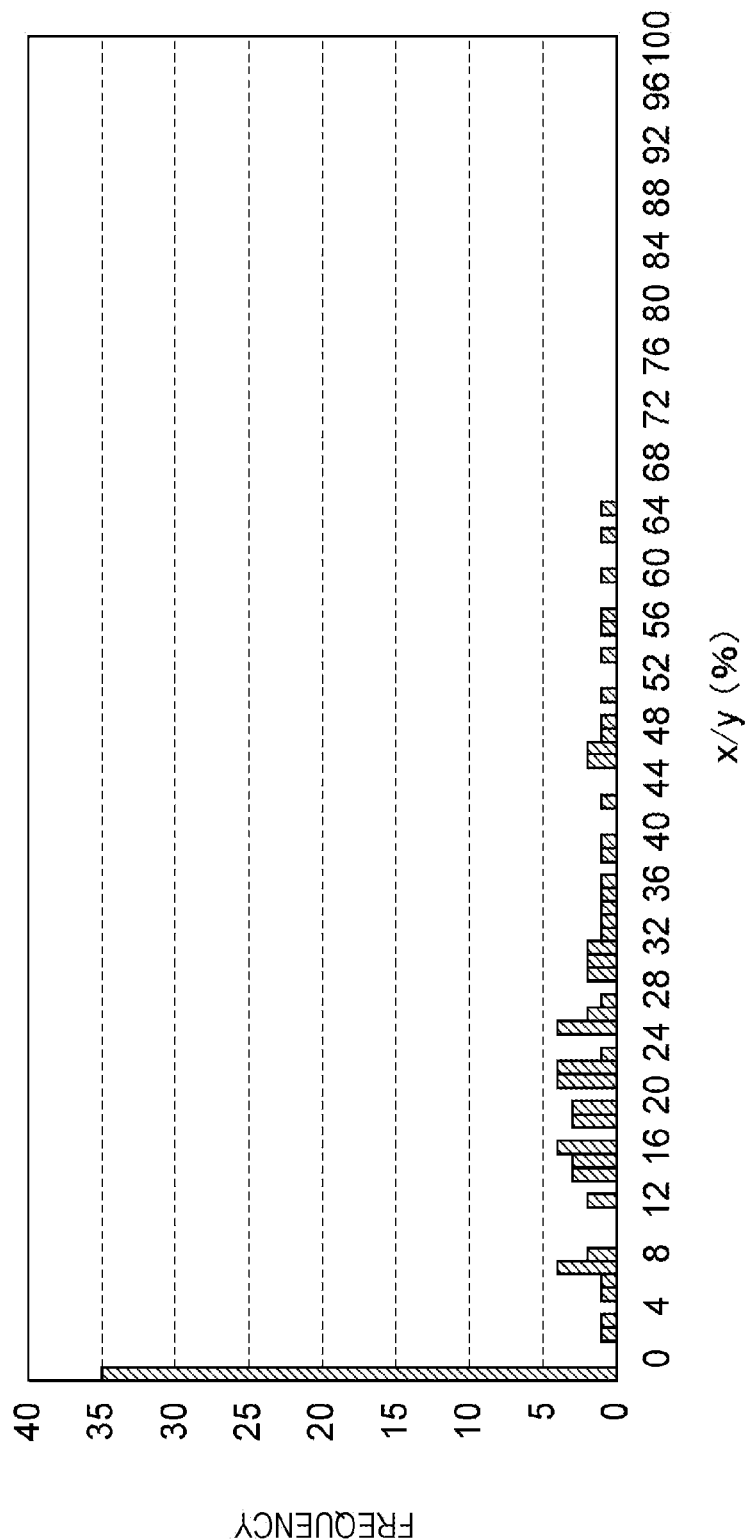
FIG. 3 is a graph illustrating a distribution of values of x/y (%) in naturally derived fibroin.

The horizontal axis in FIG. 3 represents x/y (%), and the vertical axis represents a frequency. As is clear from FIG. 3, the values of x/y in naturally derived fibroin are all smaller than 64.2% (the largest value is 64.14%).

The third modified fibroin can be obtained from, for example, a cloned gene sequence of naturally derived fibroin, by deleting one or a plurality of sequences encoding an $(A)_n$ motif so that x/y is 64.2% or more. In addition, for example, the third modified fibroin can also be obtained, from the amino acid sequence of naturally derived fibroin, by designing an amino acid sequence corresponding to an amino acid sequence in which one or a plurality of $(A)_n$ motifs are deleted so that x/y is 64.2% or more, and chemically synthesizing a nucleic acid encoding the designed amino acid sequence. In any case, in addition to the modification corresponding to deletion of the $(A)_n$ motif from the amino acid sequence of naturally derived fibroin, modification of the amino acid sequence corresponding to substitution, deletion, insertion, and/or addition of one or a plurality of amino acid residues may be performed.

A more specific example of the third modified fibroin can include modified fibroin including (3-i) the amino acid sequence set forth in SEQ ID NO: 17 (Met-PRT399), SEQ ID NO: 7 (Met-PRT410), SEQ ID NO: 8 (Met-PRT525), or SEQ ID NO: 9 (Met-PRT799), or (3-ii) an amino acid sequence having 90% or more sequence identity with the amino acid sequence set forth in SEQ ID NO: 17, SEQ ID NO: 7, SEQ ID NO: 8, or SEQ ID NO: 9.

The modified fibroin of (3-i) will be described. The amino acid sequence set forth in SEQ ID NO: 17 is obtained by deleting every other two $(A)_n$ motifs from the N-terminal side to the C-terminal side from the amino acid sequence set forth in SEQ ID NO: 10 (Met-PRT313) corresponding to naturally derived fibroin and further inserting one $[(A)_n$ motif-REP] before the C-terminal sequence. The amino acid sequence set forth in SEQ ID NO: 7, SEQ ID NO: 8, or SEQ ID NO: 9 is as described in the second modified fibroin.

The value of x/y in the amino acid sequence set forth in SEQ ID NO: 10 (corresponding to naturally derived fibroin) at a Giza ratio of 1:1.8 to 11.3 is 15.0%. Both the value of x/y in the amino acid sequence set forth in SEQ ID NO: 17 and the value of x/y in the amino acid sequence set forth in SEQ ID NO: 7 are 93.4%. The value of x/y in the amino acid sequence set forth in SEQ ID NO: 8 is 92.7%. The value of x/y in the amino acid sequence set forth in SEQ ID NO: 9 is 89.8%. The values of z/w in the amino acid sequences set forth in SEQ ID NO: 10, SEQ ID NO: 17, SEQ ID NO: 7, SEQ ID NO: 8, and SEQ ID NO: 9 are 46.8%, 56.2%, 70.1%, 66.1%, and 70.0%, respectively.

The modified fibroin of (3-i) may consist of the amino acid sequence set forth in SEQ ID NO: 17, SEQ ID NO: 7, SEQ ID NO: 8, or SEQ ID NO: 9.

The modified fibroin of (3-ii) includes an amino acid sequence having 90% or more sequence identity with the amino acid sequence set forth in SEQ ID NO: 17, SEQ ID NO: 7, SEQ ID NO: 8, or SEQ ID NO: 9. The modified fibroin of (3-ii) is also a protein including a domain sequence represented by Formula 1: $[(A)_n$ motif-REP$]_m$. The sequence identity is preferably 95% or more.

It is preferred that the modified fibroin of (3-ii) has 90% or more sequence identity with the amino acid sequence set forth in SEQ ID NO: 17, SEQ ID NO: 7, SEQ ID NO: 8, or SEQ ID NO: 9, and x/y is 64.2% or more in a case where the numbers of amino acid residues in REPs of two adjacent $[(A)_n$ motif-REP] units are sequentially compared from the N-terminal side to the C-terminal side, and the number of amino acid residues in one REP having a small number of amino acid residues is defined as 1, the maximum value of the total value of the number of amino acid residues in the two adjacent $[(A)_n$ motif-REP] units where the ratio of the number of amino acid residues in the other REP is 1.8 to 11.3 (the Giza ratio is 1:1.8 to 11.3) is defined as x, and the total number of amino acid residues in the domain sequence is defined as y.

The third modified fibroin may include the above-described tag sequence at either or both of the N-terminal and the C-terminal.

A more specific example of the modified fibroin including a tag sequence can include modified fibroin including (3-iii) the amino acid sequence set forth in SEQ ID NO: 18 (PRT399), SEQ ID NO: 13 (PRT410), SEQ ID NO: 14 (PRT525), or SEQ ID NO: 15 (PRT799), or (3-iv) an amino acid sequence having 90% or more sequence identity with the amino acid sequence set forth in SEQ ID NO: 18, SEQ ID NO: 13, SEQ ID NO: 14, or SEQ ID NO: 15.

Each of the amino acid sequences set forth in SEQ ID NO: 18, SEQ ID NO: 13, SEQ ID NO: 14, and SEQ ID NO: 15 is obtained by adding the amino acid sequence set forth in SEQ ID NO: 11 (including a His tag sequence and a hinge sequence) to the N-terminal of each of the amino acid sequences set forth in SEQ ID NO: 17, SEQ ID NO: 7, SEQ ID NO: 8, and SEQ ID NO: 9.

The modified fibroin of (3-iii) may consist of the amino acid sequence set forth in SEQ ID NO: 18, SEQ ID NO: 13, SEQ ID NO: 14, or SEQ ID NO: 15.

The modified fibroin of (3-iv) includes an amino acid sequence having 90% or more sequence identity with the amino acid sequence set forth in SEQ ID NO: 18, SEQ ID NO: 13, SEQ ID NO: 14, or SEQ ID NO: 15. The modified fibroin of (3-iv) is also a protein including a domain sequence represented by Formula 1: $[(A)_n$ motif-REP$]_m$. The sequence identity is preferably 95% or more.

It is preferred that the modified fibroin of (3-iv) has 90% or more sequence identity with the amino acid sequence set forth in SEQ ID NO: 18, SEQ ID NO: 13, SEQ ID NO: 14, or SEQ ID NO: 15, and x/y is 64.2% or more in a case where the number of amino acid residues in REPs in two adjacent $[(A)_n$ motif-REP] units are sequentially compared from the N-terminal side to the C-terminal side, and the number of amino acid residues in one REP having a small number of amino acid residues is defined as 1, the maximum value of the total value of the number of amino acid residues in the two adjacent $[(A)_n$ motif-REP] units where the ratio of the number of amino acid residues in the other REP is 1.8 to 11.3 is defined as x, and the total number of amino acid residues in the domain sequence is defined as y.

The third modified fibroin may include a secretory signal for releasing the protein produced in the recombinant protein production system to the outside of a host. The sequence of the secretory signal can be appropriately set depending on the type of the host.

The domain sequence of the fourth modified fibroin has an amino acid sequence in which the content of an $(A)_n$ motif and the content of glycine residues are reduced, as compared with naturally derived fibroin. It can be said that the domain sequence of the fourth modified fibroin has an amino acid sequence corresponding to an amino acid sequence in which at least one or a plurality of $(A)_n$ motifs are deleted and at least one or a plurality of glycine residues in REP are substituted with another amino acid residue, as compared with naturally derived fibroin. That is, the fourth modified fibroin is modified fibroin having the characteristics of the above-described second modified fibroin and third modified fibroin. Specific aspects thereof, and the like are as in the descriptions for the second modified fibroin and the third modified fibroin.

A more specific example of the fourth modified fibroin can include modified fibroin including (4-i) the amino acid sequence set forth in SEQ ID NO: 7 (Met-PRT410), SEQ ID NO: 8 (Met-PRT525), SEQ ID NO: 9 (Met-PRT799), SEQ ID NO: 13 (PRT410), SEQ ID NO: 14 (PRT525), or SEQ ID NO: 15 (PRT799), or (4-ii) an amino acid sequence having 90% or more sequence identity with the amino acid sequence set forth in SEQ ID NO: 7, SEQ ID NO: 8, SEQ ID NO: 9, SEQ ID NO: 13, SEQ ID NO: 14, or SEQ ID NO: 15. Specific aspects of the modified fibroin including the amino acid sequence set forth in SEQ ID NO: 7, SEQ ID NO: 8, SEQ ID NO: 9, SEQ ID NO: 13, SEQ ID NO: 14, or SEQ ID NO: 15 are as described above.

The domain sequence of the fifth modified fibroin may have an amino acid sequence including a region locally having a high hydropathy index corresponding to an amino acid sequence in which one or a plurality of amino acid residues in REP are substituted with amino acid residues having a high hydropathy index and/or one or a plurality of amino acid residues having a high hydropathy index are inserted into REP, as compared with naturally derived fibroin.

The region locally having a high hydropathy index preferably consists of consecutive two to four amino acid residues.

The above-described amino acid residue having a high hydropathy index is more preferably an amino acid residue selected from isoleucine (I), valine (V), leucine (L), phenylalanine (F), cysteine (C), methionine (M), and alanine (A).

The fifth modified fibroin may be further subjected to modification of an amino acid sequence corresponding to substitution, deletion, insertion, and/or addition of one or a plurality of amino acid residues as compared with naturally derived fibroin, in addition to modification corresponding to substitution of one or a plurality of amino acid residues in REP with amino acid residues having a high hydropathy index and/or insertion of one or a plurality of amino acid residues having a high hydropathy index into REP, as compared with naturally derived fibroin.

The fifth modified fibroin can be obtained by, for example, substituting one or a plurality of hydrophilic amino acid residues in REP (for example, amino acid residues having a negative hydropathy index) with hydrophobic amino acid residues (for example, amino acid residues having a positive hydropathy index) from a cloned gene sequence of naturally derived fibroin, and/or inserting one or a plurality of hydrophobic amino acid residues into REP. In addition, the fifth modified fibroin can be obtained by, for example, designing an amino acid sequence corresponding to an amino acid sequence in which one or a plurality of hydrophilic amino acid residues in REP are substituted with hydrophobic amino acid residues from an amino acid sequence of naturally derived fibroin, and/or one or a plurality of hydrophobic amino acid residues are inserted into REP, and chemically synthesizing a nucleic acid encoding the designed amino acid sequence. In any case, in addition to modification corresponding to substitution of one or a plurality of hydrophilic amino acid residues in REP with hydrophobic amino acid residues from an amino acid sequence of naturally derived fibroin, and/or insertion of one or a plurality of hydrophobic amino acid residues into REP, modification of an amino acid sequence corresponding to substitution, deletion, insertion, and/or addition of one or a plurality of amino acid residues may be further performed.

The fifth modified fibroin includes a domain sequence represented by Formula 1: $[(A)_n$ motif-REP$]_m$, and may have an amino acid sequence in which p/q is 6.2% or more in a case where in all REPs included in a sequence excluding the sequence from the $(A)_n$ motif located at the most C-terminal side to the C-terminal of the domain sequence from the domain sequence, the total number of amino acid residues included in a region where the average value of hydropathy indices of four consecutive amino acid residues is 2.6 or more is defined as p, and the total number of amino acid residues included in the sequence excluding the sequence from the $(A)_n$ motif located at the most C-terminal side to the C-terminal of the domain sequence from the domain sequence is defined as q.

A known index (Hydropathy index: Kyte J, & Doolittle R (1982), "A simple method for displaying the hydropathic character of a protein", J. Mol. Biol., 157, pp. 105-132) is used as the hydropathy index of the amino acid residue. Specifically, the hydropathy index (hereinafter, also referred to as "HI") of each amino acid is as shown in Table 1.

TABLE 1

| Amino acid | HI | Amino acid | HI |
| --- | --- | --- | --- |
| Isoleucine (Ile) | 4.5 | Tryptophan (Trp) | −0.9 |
| Valine (Val) | 4.2 | Tyrosine (Tyr) | −1.3 |
| Leucine (Leu) | 3.8 | Proline (Pro) | −1.6 |
| Phenylalanine (Phe) | 2.8 | Histidine (His) | −3.2 |
| Cysteine (Cys) | 2.5 | Asparagine (Asn) | −3.5 |
| Methionine (Met) | 1.9 | Aspartic acid (Asp) | −3.5 |
| Alanine (Ala) | 1.8 | Glutamine (Gln) | −3.5 |
| Glycine (Gly) | −0.4 | Glutamine acid (Glu) | −3.5 |
| Threonine (Thr) | −0.7 | Lysine (Lys) | −3.9 |
| Serine (Ser) | −0.8 | Arginine (Arg) | −4.5 |

The method of calculating p/q will be described in more detail. In the calculation, a sequence excluding the sequence from the $(A)_n$ motif located at the most C-terminal side to the C-terminal of the domain sequence from the domain sequence represented by Formula 1 $[(A)_n$ motif-REP$]_m$ (hereinafter also referred to as "sequence A") is used. First, in all REPs included in the sequence A, the average values of hydropathy indices of four consecutive amino acid residues are calculated. The average value of hydropathy indices is determined by dividing the sum of HIs of respective amino acid residues included in the four consecutive amino acid residues by 4 (number of amino acid residues). The average value of hydropathy indices is determined for all of the four consecutive amino acid residues (each of the amino acid residues is used for calculating the average value 1 to 4 times). Then, a region where the average value of hydropathy indices of the four consecutive amino acid residues is 2.6 or more is specified. Even in a case where a certain amino acid residue corresponds to the "four consecutive amino acid residues having an average value of hydropathy indices of 2.6 or more" multiple times, the amino acid residue is included as one amino acid residue in the region. The total number of amino acid residues included in the region is p. Also, the total number of amino acid residues included in the sequence A is q.

Figure 4:
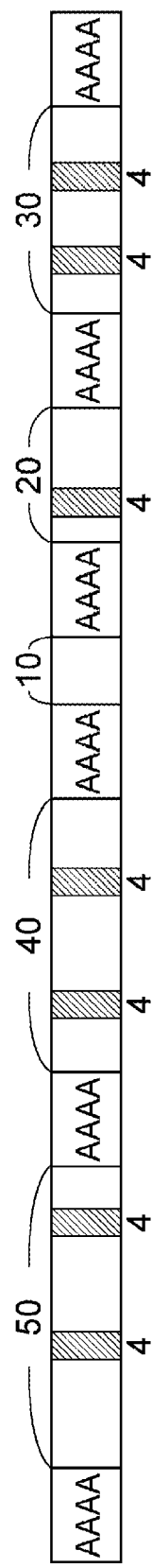
FIG. 4 is a schematic diagram illustrating an example of a domain sequence of modified fibroin.

For example, in a case where the "four consecutive amino acid residues having an average value of hydropathy indices of 2.6 or more" are extracted from 20 places (no overlap), in the region where the average value of hydropathy indices of four consecutive amino acid residues is 2.6 or more, 20 of the four consecutive amino acid residues (no overlap) are included, and thus p is 20×4=80. Further, for example, in a case where two of the "four consecutive amino acid residues having an average value of hydropathy indices of 2.6 or more" overlap by one amino acid residue, in the region where the average value of hydropathy indices of the four consecutive amino acid residues is 2.6 or more, seven amino acid residues are included (p=2×4−1=7. "−1" is the deduction of the overlapping portion). For example, in a case of the domain sequence shown in FIG. 4, seven sets of "four consecutive amino acid residues having an average value of hydropathy indices of 2.6 or more" are present without overlaps, and thus, p is 7×4=28. Furthermore, for example, in the case of the domain sequence shown in FIG. 4, q is 4+50+4+40+4+10+4+20+4+30=170 (the $(A)_n$ motif located at the end of the C-terminal side is excluded). Next, p/q (%) can be calculated by dividing p by q. In the case of FIG. 4, p/q is 28/170=16.47%.

In the fifth modified fibroin, p/q is preferably 6.2% or more, more preferably 7% or more, still more preferably 10% or more, even still more preferably 20% or more, and still further preferably 30% or more. The upper limit of p/q is not particularly limited, but may be 45% or less, for example.

The fifth modified fibroin can be obtained by, for example, substituting one or a plurality of hydrophilic amino acid residues in REP (for example, amino acid residues having a negative hydropathy index) with hydrophobic amino acid residues (for example, amino acid residues having a positive hydropathy index) so that a cloned amino acid sequence of naturally derived fibroin satisfies the condition of p/q, and/or modifying the cloned amino acid sequence of naturally derived fibroin into an amino acid sequence including a region locally having a high hydropathy index by inserting one or a plurality of hydrophobic amino acid residues into REP. In addition, the fifth modified fibroin can also be obtained by, for example, designing an amino acid sequence satisfying the condition of p/q from the amino acid sequence of naturally derived fibroin, and chemically synthesizing a nucleic acid encoding the designed amino acid sequence. In any case, modification corresponding to substitution, deletion, insertion, and/or addition of one or a plurality of amino acid residues may also be performed, in addition to modification corresponding to substitution of one or a plurality of amino acid residues in REP with amino acid residues having a high hydropathy index, and/or insertion of one or a plurality of amino acid residues having a high hydropathy index into REP, as compared with naturally derived fibroin.

The amino acid residue having a high hydropathy index is not particularly limited, but is preferably isoleucine (I), valine (V), leucine (L), phenylalanine (F), cysteine (C), methionine (M), and alanine (A), and more preferably valine (V), leucine (L), and isoleucine (I).

A more specific example of the fifth modified fibroin can include modified fibroin including (5-i) the amino acid sequence set forth in SEQ ID NO: 19 (Met-PRT720), SEQ ID NO: 20 (Met-PRT665), or SEQ ID NO: 21 (Met-PRT666), or (5-ii) an amino acid sequence having 90% or more sequence identity with the amino acid sequence set forth in SEQ ID NO: 19, SEQ ID NO: 20, or SEQ ID NO: 21.

The modified fibroin of (5-i) will be described. The amino acid sequence set forth in SEQ ID NO: 19 is obtained by inserting an amino acid sequence consisting of three amino acid residues (VLI) at two sites for each REP into the amino acid sequence set forth in SEQ ID NO: 7 (Met-PRT410), except for the domain sequence at the end on the C-terminal side, and further substituting a part of glutamine (Q) residues with serine (S) residues, and deleting a part of amino acids on the C-terminal side. The amino acid sequence set forth in SEQ ID NO: 20 is obtained by inserting the amino acid sequence consisting of three amino acid residues (VLI) at one site for each REP into the amino acid sequence set forth in SEQ ID NO: 8 (Met-PRT525). The amino acid sequence set forth in SEQ ID NO: 21 is obtained by inserting the amino acid sequence consisting of three amino acid residues (VLI) at two sites for each REP into the amino acid sequence set forth in SEQ ID NO: 8.

The modified fibroin of (5-i) may consist of the amino acid sequence set forth in SEQ ID NO: 19, SEQ ID NO: 20, or SEQ ID NO: 21.

The modified fibroin of (5-ii) includes an amino acid sequence having 90% or more sequence identity with the amino acid sequence set forth in SEQ ID NO: 19, SEQ ID NO: 20, or SEQ ID NO: 21. The modified fibroin of (5-ii) is also a protein including a domain sequence represented by Formula 1: $[(A)_n \text{ motif-REP}]_m$. The sequence identity is preferably 95% or more.

It is preferred that the modified fibroin of (5-ii) has 90% or more sequence identity with the amino acid sequence set forth in SEQ ID NO: 19, SEQ ID NO: 20, or SEQ ID NO: 21, and p/q is 6.2% or more in a case where in all REPs included in a sequence excluding the sequence from the $(A)_n$ motif located at the most C-terminal side to the C-terminal of the domain sequence from the domain sequence, the total number of amino acid residues included in a region where the average value of hydropathy indices of four consecutive amino acid residues is 2.6 or more is defined as p, and the total number of amino acid residues included in the sequence excluding the sequence from the $(A)_n$ motif located at the most the C-terminal side to the C-terminal of the domain sequence from the domain sequence is defined as q.

The fifth modified fibroin may include a tag sequence at either or both of the N-terminal and the C-terminal.

A more specific example of the modified fibroin including a tag sequence can include modified fibroin including (5-iii) the amino acid sequence set forth in SEQ ID NO: 22 (PRT720), SEQ ID NO: 23 (PRT665), or SEQ ID NO: 24 (PRT666), or (5-iv) an amino acid sequence having 90% or more sequence identity with the amino acid sequence set forth in SEQ ID NO: 22, SEQ ID NO: 23, or SEQ ID NO: 24.

Each of the amino acid sequences set forth in SEQ ID NO: 22, SEQ ID NO: 23, and SEQ ID NO: 24 is obtained by adding the amino acid sequence set forth in SEQ ID NO: 11 (including a His tag sequence and a hinge sequence) to the N-terminal of each of the amino acid sequences set forth in SEQ ID NO: 19, SEQ ID NO: 20, and SEQ ID NO: 21.

The modified fibroin of (5-iii) may consist of the amino acid sequence set forth in SEQ ID NO: 22, SEQ ID NO: 23, or SEQ ID NO: 24.

The modified fibroin of (5-iv) includes an amino acid sequence having 90% or more sequence identity with the amino acid sequence set forth in SEQ ID NO: 22, SEQ ID NO: 23, or SEQ ID NO: 24. The modified fibroin of (5-iv) is also a protein including a domain sequence represented by Formula 1: $[(A)_n$ motif-REP$]_m$. The sequence identity is preferably 95% or more.

It is preferred that the modified fibroin of (5-iv) has 90% or more sequence identity with the amino acid sequence set forth in SEQ ID NO: 22, SEQ ID NO: 23, or SEQ ID NO: 24, and p/q is 6.2% or more in a case where in all REPs included in a sequence excluding the sequence from the $(A)_n$ motif located at the most C-terminal side to the C-terminal of the domain sequence from the domain sequence, the total number of amino acid residues included in a region where the average value of hydropathy indices of four consecutive amino acid residues is 2.6 or more is defined as p, and the total number of amino acid residues included in the sequence excluding the sequence from the $(A)_n$ motif located at the most C-terminal side to the C-terminal of the domain sequence from the domain sequence is defined as q.

The fifth modified fibroin may include a secretory signal for releasing the protein produced in the recombinant protein production system to the outside of a host. The sequence of the secretory signal can be appropriately set depending on the type of the host.

The sixth modified fibroin has an amino acid sequence in which the content of glutamine residues is reduced, as compared with naturally derived fibroin.

In the sixth modified fibroin, at least one motif selected from a GGX motif and a GPGXX motif is preferably included in the amino acid sequence of REP.

In a case where the sixth modified fibroin has the GPGXX motif in REP, the GPGXX motif content is usually 1% or more, may also be 5% or more, and preferably 10% or more. The upper limit of the GPGXX motif content is not particularly limited, and may be 50% or less, or may also be 30% or less.

In the present specification, the "GPGXX motif content" is a value calculated by the following method.

The content rate of the GPGXX motif in fibroin (modified fibroin or naturally derived fibroin) including a domain sequence represented by Formula 1: $[(A)_n$ motif-REP$]_m$ or Formula 2: $[(A)_n$ motif-REP$]_m$-$(A)_n$ motif is calculated as s/t, in a case where the number obtained by tripling the total number of GPGXX motifs in regions of all REPs included in a sequence excluding the sequence from the $(A)_n$ motif located at the most C-terminal side to the C-terminal of the domain sequence from the domain sequence (that is, corresponding to the total number of G and P in the GPGXX motifs) is defined as s, and the total number of amino acid residues in all REPs excluding a sequence from the $(A)_n$ motif located at the most C-terminal side to the C-terminal of the domain sequence from the domain sequence and further excluding the $(A)_n$ motifs is defined as t.

In the calculation of the content rate of the GPGXX motif, the "sequence excluding the sequence from the $(A)_n$ motif located at the most C-terminal side to the C-terminal of the domain sequence from the domain sequence" is used to exclude the effect occurring due to the fact that the "sequence from the $(A)_n$ motif located at the most C-terminal side to the C-terminal of the domain sequence" (a sequence corresponding to REP) may include a sequence having a low correlation with the sequence characteristic of fibroin, which influences the calculation result of the content rate of the GPGXX motif in a case where m is small (that is, in a case where the domain sequence is short). Incidentally, in a case where the "GPGXX motif" is located at the C-terminal of REP, even when "XX" is "AA", for example, it is treated as the "GPGXX motif".

Figure 5:
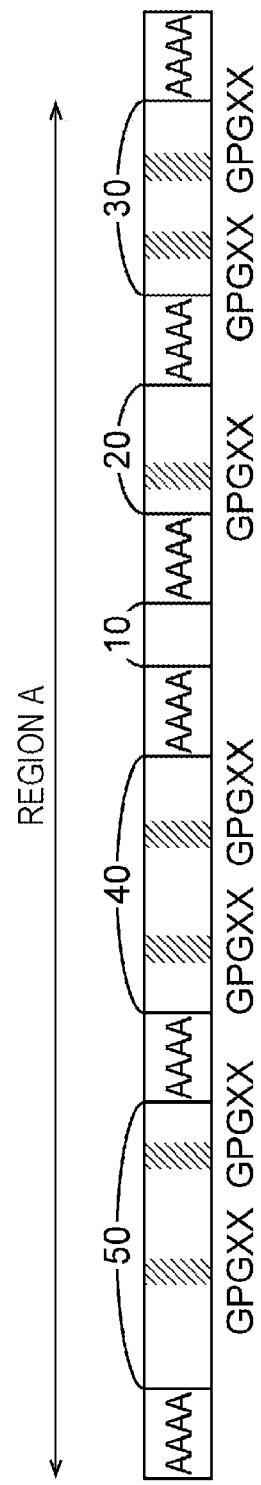
FIG. 5 is a schematic diagram illustrating an example of a domain sequence of modified fibroin.

FIG. 5 is a schematic diagram illustrating a domain sequence of modified fibroin. The method for calculating the content rate of the GPGXX motif will be specifically described with reference to FIG. 5. First, in the domain sequence of the modified fibroin shown in FIG. 5 (which is the "$[(A)_n$ motif-REP$]_m$-$(A)_n$ motif" type), all REPs are included in the "sequence excluding the sequence from the $(A)_n$ motif located at the most C-terminal side to the C-terminal of the domain sequence from the domain sequence" (in FIG. 5, the sequence indicated as a "region A"), and therefore, the number of the GPGXX motifs for calculating s is 7, and s is 7×3=21. Similarly, since all REPs are included in the "sequence excluding the sequence from the $(A)_n$ motif located at the most C-terminal side to the C-terminal of the domain sequence from the domain sequence" (in FIG. 5, the sequence indicated as the "region A"), the total number t of the amino acid residues in all REPs when the $(A)_n$ motifs are further excluded from the sequence is 50+40+10+20+30=150. Next, s/t (%) can be calculated by dividing s by t, and in the case of the modified fibroin of FIG. 5, s/t is 21/150=14.0%.

In the sixth modified fibroin, the glutamine residue content is preferably 9% or less, more preferably 7% or less, still more preferably 4% or less, and particularly preferably 0%.

In the present specification, the "glutamine residue content" is a value calculated by the following method.

The glutamine residue content in fibroin (modified fibroin or naturally derived fibroin) including a domain sequence represented by Formula 1: $[(A)_n$ motif-REP$]_m$ or Formula 2: $[(A)_n$ motif-REP$]_m$-$(A)_n$ motif is calculated as u/t, in a case where the total number of glutamine residues included in regions of all REPs included in a sequence excluding the sequence from the $(A)_n$ motif located at the most C-terminal side to the C-terminal of the domain sequence from the domain sequence (a sequence corresponding to the "region A" in FIG. 5) is defined as u, and the total number of amino acid residues in all REPs in the sequence excluding the sequence from the $(A)_n$ motif located at the most C-terminal side to the C-terminal of the domain sequence from the domain sequence and further excluding the $(A)_n$ motifs is defined as t. In the calculation of the glutamine residue content, the reason for targeting the "sequence excluding the sequence from the $(A)_n$ motif located at the most C-terminal side to the C-terminal of the domain sequence from the domain sequence" is the same as the reason descried above.

The domain sequence of the sixth modified fibroin may have an amino acid sequence corresponding to an amino acid sequence in which one or a plurality of glutamine residues in REP are deleted, or one or a plurality of glutamine residues are substituted with another amino acid residue, as compared with naturally derived fibroin.

The "another amino acid residue" may be an amino acid residue other than the glutamine residue, but is preferably an amino acid residue having a higher hydropathy index than that of the glutamine residue. The hydropathy index of the amino acid residue is as shown in Table 1.

As shown in Table 1, examples of the amino acid residue having a higher hydropathy index than that of the glutamine residue include amino acid residues selected from isoleucine (I), valine (V), leucine (L), phenylalanine (F), cysteine (C), methionine (M), alanine (A), glycine (G), threonine (T), serine (S), tryptophan (W), tyrosine (Y), proline (P), and histidine (H). Among them, the amino acid residue is more preferably an amino acid residue selected from isoleucine (I), valine (V), leucine (L), phenylalanine (F), cysteine (C), methionine (M), and alanine (A), and still more preferably an amino acid residue selected from isoleucine (I), valine (V), leucine (L), and phenylalanine (F).

In the sixth modified fibroin, the hydrophobicity of REP is preferably −0.8 or more, more preferably −0.7 or more, still more preferably 0 or more, even still more preferably 0.3 or more, and particularly preferably 0.4 or more. The upper limit of the hydrophobicity of REP is not particularly limited, but may be 1.0 or less or 0.7 or less.

In the present specification, the "hydrophobicity of REP" is a value calculated by the following method.

The hydrophobicity of REP in fibroin including a domain sequence represented by Formula 1: [(A)$_n$ motif-REP]$_m$ or Formula 2: [(A)$_n$ motif-REP]$_m$-(A)$_n$ motif (modified fibroin or naturally derived fibroin) is calculated as v/t, in a case where the sum of hydropathy indices of amino acid residues in regions of all REPs included in a sequence excluding the sequence from the (A)$_n$ motif located at the most C-terminal side to the C-terminal of the domain sequence from the domain sequence (a sequence corresponding to the "region A" in FIG. 5) is defined as v, and the total number of amino acid residues in all REPs in the sequence excluding the sequence from the (A)$_n$ motif located at the most C-terminal side to the C-terminal of the domain sequence from the domain sequence and further excluding the (A)$_n$ motifs is defined as t. In the calculation of the hydrophobicity of REP, the reason for targeting the "sequence excluding the sequence from the (A)$_n$ motif located at the most C-terminal side to the C-terminal of the domain sequence from the domain sequence" is the same as the reason descried above.

The domain sequence of the sixth modified fibroin may be further subjected to modification of an amino acid sequence corresponding to substitution, deletion, insertion, and/or addition of one or a plurality of amino acid residues, in addition to modification corresponding to deletion of one or a plurality of glutamine residues in REP, and/or substitution of one or a plurality of glutamine residues in REP with another amino acid residue, as compared with naturally derived fibroin.

The sixth modified fibroin can be obtained by, for example, deleting one or a plurality of glutamine residues in REP from a cloned gene sequence of naturally derived fibroin, and/or substituting one or a plurality of glutamine residues in REP with another amino acid residue. In addition, the sixth modified fibroin can be obtained by, for example, designing an amino acid sequence corresponding to an amino acid sequence in which one or a plurality of glutamine residues in REP are deleted from an amino acid sequence of naturally derived fibroin, and/or one or a plurality of glutamine residues in REP are substituted with another amino acid residue, and chemically synthesizing a nucleic acid encoding the designed amino acid sequence.

A more specific example of the sixth modified fibroin can include modified fibroin including (6-i) the amino acid sequence set forth in SEQ ID NO: 25 (Met-PRT888), SEQ ID NO: 26 (Met-PRT965), SEQ ID NO: 27 (Met-PRT889), SEQ ID NO: 28 (Met-PRT916), SEQ ID NO: 29 (Met-PRT918), SEQ ID NO: 30 (Met-PRT699), SEQ ID NO: 31 (Met-PRT698), SEQ ID NO: 32 (Met-PRT966), SEQ ID NO: 41 (Met-PRT917), or SEQ ID NO: 42 (Met-PRT1028), and modified fibroin including (6-ii) an amino acid sequence having 90% or more sequence identity with the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin of (6-i) will be described. The amino acid sequence set forth in SEQ ID NO: 25 is obtained by substituting all QQs in the amino acid sequence set forth in SEQ ID NO: 7 (Met-PRT410) with VL. The amino acid sequence set forth in SEQ ID NO: 26 is obtained by substituting all QQs in the amino acid sequence set forth in SEQ ID NO: 7 with TS and substituting the remaining Q with A. The amino acid sequence set forth in SEQ ID NO: 27 is obtained by substituting all QQs in the amino acid sequence set forth in SEQ ID NO: 7 with VL and substituting the remaining Q with I. The amino acid sequence set forth in SEQ ID NO: 28 is obtained by substituting all QQs in the amino acid sequence set forth in SEQ ID NO: 7 with VI and substituting the remaining Q with L. The amino acid sequence set forth in SEQ ID NO: 29 is obtained by substituting all QQs in the amino acid sequence set forth in SEQ ID NO: 7 with VF and substituting the remaining Q with I.

The amino acid sequence set forth in SEQ ID NO: 30 is obtained by substituting all QQs in the amino acid sequence set forth in SEQ ID NO: 8 (Met-PRT525) with VL. The amino acid sequence set forth in SEQ ID NO: 31 is obtained by substituting all QQs in the amino acid sequence set forth in SEQ ID NO: 8 with VL and substituting the remaining Q with I.

The amino acid sequence set forth in SEQ ID NO: 32 is obtained by substituting, with VF, all QQs in a sequence obtained by repeating a region of 20 domain sequences present in the amino acid sequence set forth in SEQ ID NO: 7 (Met-PRT410) two times and substituting the remaining Q with I.

The amino acid sequence set forth in SEQ ID NO: 41 (Met-PRT917) is obtained by substituting all QQs in the amino acid sequence set forth in SEQ ID NO: 7 with LI and substituting the remaining Q with V. The amino acid sequence set forth in SEQ ID NO: 42 (Met-PRT1028) is obtained by substituting all QQs in the amino acid sequence set forth in SEQ ID NO: 7 with IF and substituting the remaining Q with T.

The glutamine residue content in each of the amino acid sequences set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42 is 9% or less (Table 2).

TABLE 2

| Modified Fibroin | Glutamine residue content | GPGXX motif content | Hydrophobicity of REP |
|---|---|---|---|
| Met-PRT410 (SEQ ID NO: 7) | 17.7% | 27.9% | −1.52 |
| Met-PRT888 (SEQ ID NO: 25) | 6.3% | 27.9% | −0.07 |
| Met-PRT965 (SEQ ID NO: 26) | 0.0% | 27.9% | −0.65 |
| Met-PRT889 (SEQ ID NO: 27) | 0.0% | 27.9% | 0.35 |
| Met-PRT916 (SEQ ID NO: 28) | 0.0% | 27.9% | 0.47 |
| Met-PRT918 (SEQ ID NO: 29) | 0.0% | 27.9% | 0.45 |
| Met-PRT699 (SEQ ID NO: 30) | 3.6% | 26.4% | −0.78 |
| Met-PRT698 (SEQ ID NO: 31) | 0.0% | 26.4% | −0.03 |
| Met-PRT966 (SEQ ID NO: 32) | 0.0% | 28.0% | 0.35 |
| Met-PRT917 (SEQ ID NO: 41) | 0.0% | 27.9% | 0.46 |
| Met-PRT1028 (SEQ ID NO: 42) | 0.0% | 28.1% | 0.05 |

The modified fibroin of (6-i) may consist of the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin of (6-ii) includes an amino acid sequence having 90% or more sequence identity with the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42. The modified fibroin of (6-ii) is also a protein including a domain sequence represented by Formula 1: [(A)$_n$ motif-REP], or Formula 2: [(A)$_n$ motif-REP]$_m$-(A)$_n$ motif. The sequence identity is preferably 95% or more.

In the modified fibroin of (6-ii), the glutamine residue content is preferably 9% or less. In the modified fibroin of (6-ii), the GPGXX motif content is preferably 10% or more.

The sixth modified fibroin may have a tag sequence at either or both of the N-terminal and the C-terminal. This enables the modified fibroin to be isolated, immobilized, detected, and visualized.

A more specific example of the modified fibroin including a tag sequence can include modified fibroin including (6-iii) the amino acid sequence set forth in SEQ ID NO: 33 (PRT888), SEQ ID NO: 34 (PRT965), SEQ ID NO: 35 (PRT889), SEQ ID NO: 36 (PRT916), SEQ ID NO: 37 (PRT918), SEQ ID NO: 38 (PRT699), SEQ ID NO: 39 (PRT698), SEQ ID NO: 40 (PRT966), SEQ ID NO: 43 (PRT917), or SEQ ID NO: 44 (PRT1028), or modified fibroin including (6-iv) an amino acid sequence having 90% or more sequence identity with the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

Each of the amino acid sequences set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, and SEQ ID NO: 44 is obtained by adding the amino acid sequence set forth in SEQ ID NO: 11 (including a His tag sequence and a hinge sequence) to the N-terminal of each of the amino acid sequences set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42. Since only the tag sequence is added to the N-terminal, the glutamine residue content is not changed, and the glutamine residue content in each of the amino acid sequences set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44 is 9% or less (Table 3).

TABLE 3

| Modified Fibroin | Glutamine residue content | GPGXX motif content | Hydrophobicity of REP |
|---|---|---|---|
| PRT888 (SEQ ID NO: 33) | 6.3% | 27.9% | −0.07 |
| PRT965 (SEQ ID NO: 34) | 0.0% | 27.9% | −0.65 |
| PRT889 (SEQ ID NO: 35) | 0.0% | 27.9% | 0.35 |
| PRT916 (SEQ ID NO: 36) | 0.0% | 27.9% | 0.47 |
| PRT918 (SEQ ID NO: 37) | 0.0% | 27.9% | 0.45 |
| PRT699 (SEQ ID NO: 38) | 3.6% | 26.4% | −0.78 |
| PRT698 (SEQ ID NO: 39) | 0.0% | 26.4% | −0.03 |
| PRT966 (SEQ ID NO: 40) | 0.0% | 28.0% | 0.35 |
| PRT917 (SEQ ID NO: 43) | 0.0% | 27.9% | 0.46 |
| PRT1028 (SEQ ID NO: 44) | 0.0% | 28.1% | 0.05 |

The modified fibroin of (6-iii) may consist of the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

The modified fibroin of (6-iv) includes an amino acid sequence having 90% or more sequence identity with the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44. The modified fibroin of (6-iv) is also a protein including a domain sequence represented by Formula 1: [(A)$_n$ motif-REP]$_m$ or Formula 2: [(A)$_n$ motif-REP]$_m$-(A)$_n$ motif. The sequence identity is preferably 95% or more.

In the modified fibroin of (6-iv), the glutamine residue content is preferably 9% or less. In the modified fibroin of (6-iv), the GPGXX motif content is preferably 10% or more.

The sixth modified fibroin may include a secretory signal for releasing the protein produced in the recombinant protein production system to the outside of a host. The sequence of the secretory signal can be appropriately set depending on the type of the host.

The modified fibroin may also be modified fibroin having at least two or more characteristics among the characteristics of the first modified fibroin, the second modified fibroin, the third modified fibroin, the fourth modified fibroin, the fifth modified fibroin, and the sixth modified fibroin.

The modified fibroin is preferably a hydrophilic modified fibroin because it is more excellent in water-absorbing and quick-drying properties. In the present specification, the "hydrophilic modified fibroin" is modified fibroin of which a value calculated by obtaining the sum of hydropathy indices (HIs) of all amino acid residues constituting the modified fibroin and then dividing the sum by the total number of amino acid residues (average HI) is 0 or less. The hydropathy index is as shown in Table 1. Modified fibroin having an average HI of more than 0 may also be referred to as hydrophobic modified fibroin.

Examples of the hydrophilic modified fibroin can include modified fibroin including the amino acid sequence set forth in SEQ ID NO: 4, the amino acid sequence set forth in SEQ ID NO: 6, SEQ ID NO: 7, SEQ ID NO: 8, or SEQ ID NO: 9, the amino acid sequence set forth in SEQ ID NO: 13, SEQ ID NO: 11, SEQ ID NO: 14, or SEQ ID NO: 15, the amino acid sequence set forth in SEQ ID NO: 18, SEQ ID NO: 7, SEQ ID NO: 8, or SEQ ID NO: 9, the amino acid sequence set forth in SEQ ID NO: 17, SEQ ID NO: 11, SEQ ID NO: 14, or SEQ ID NO: 15, or the amino acid sequence set forth in SEQ ID NO: 19, SEQ ID NO: 20, or SEQ ID NO: 21.

Examples of the hydrophobic modified fibroin can include modified fibroin including the amino acid sequence set forth in SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43, or the amino acid sequence set forth in SEQ ID NO: 35, SEQ ID NO: 37, SEQ ID NO: 38, SEQ ID NO: 39, SEQ ID NO: 40, SEQ ID NO: 41, or SEQ ID NO: 44.

The modified fibroin according to the present embodiment can be produced by an ordinary method using a nucleic acid encoding the modified fibroin. The nucleic acid encoding the modified fibroin may be chemically synthesized based on nucleotide sequence information, or may be synthesized using a PCR method or the like. Isolation and purification of the produced modified fibroin can be performed by a commonly used method.

(Water-Absorbing and Quick-Drying Property-Imparting Agent)

The water-absorbing and quick-drying property-imparting agent according to the present embodiment may contain one type of modified fibroin alone or a combination of two or more types thereof.

The water-absorbing properties of the water-absorbing and quick-drying property-imparting agent according to the present embodiment as evaluated in accordance with JIS L 1907 may be 60 seconds or less, 30 seconds or less, 20 seconds or less, 10 seconds or less, or 5 seconds or less. Water-absorbing properties can be evaluated, for example, by a method described in Examples described later.

The quick-drying properties of the water-absorbing and quick-drying property-imparting agent according to the present embodiment as evaluated through measurement of the diffusible residual moisture content may be 100 minutes or less, 90 minutes or less, 80 minutes or less, or 70 minutes or less. The diffusible residual moisture content (%) is a value calculated by the following equation.

Diffusible residual moisture content(%)=weight (g) of water at each time/weight (g) of water at the start of measurement×100

The quick-drying properties means a time required until the diffusible residual moisture content reaches 10% or less. The quick-drying properties can be evaluated, for example, by a method described in Examples described later.

The water-absorbing and quick-drying property-imparting agent according to the present embodiment may further contain other additives (components other than the active ingredient) according to its form, application, and the like. Examples of the additive include a plasticizer, a leveling agent, a crosslinking agent, a nucleating agent, an antioxidant, an ultraviolet absorber, a coloring agent, a filler, and a synthetic resin. The content of the additive may be 50 parts by mass or less with respect to 100 parts by mass of the total amount of the water-absorbing and quick-drying property-imparting agent.

The water-absorbing and quick-drying property-imparting agent according to the present embodiment may be in any form of, for example, a powder, a paste, and a liquid (for example, a suspension or solution). The water-absorbing and quick-drying property-imparting agent according to the present embodiment may also be in the form of, for example, a fiber, a film, a gel, a porous body, a particle, or the like. The form of the water-absorbing and quick-drying property-imparting agent according to the present embodiment may be appropriately set according to the object to which water-absorbing and quick-drying properties are imparted (water-absorbing and quick-drying property-imparted article) and the application thereof.

Since the water-absorbing and quick-drying property-imparting agent according to the present embodiment contains modified fibroin as a main component, the water-absorbing and quick-drying property-imparting agent can be formed into any form described above. The formed body may be formed of modified fibroin itself, or may be formed of a combination of modified fibroin and another material.

When the water-absorbing and quick-drying property-imparting agent according to the present embodiment is prepared in the form of a powder, for example, a protein obtained by the above-described method for producing modified fibroin may be dried into a powder. The protein powder may contain other additives as necessary.

When the water-absorbing and quick-drying property-imparting agent according to the present embodiment is prepared in the form of a liquid (for example, a solution), for example, a protein obtained by the above-described method for producing modified fibroin may be dissolved in a solvent that can dissolve modified fibroin to obtain a liquid (modified fibroin solution). The modified fibroin solution may contain other additives as necessary. Examples of the solvent that can dissolve modified fibroin can include dimethyl sulfoxide (DMSO), N,N-dimethylformamide (DMF), formic acid, and hexafluoroisopropanol (HFIP). An inorganic salt may be added to the solvent as a dissolution promoter.

When the water-absorbing and quick-drying property-imparting agent according to the present embodiment is prepared in the form of a fiber, for example, the modified fibroin solution may be used as a dope solution, and the dope solution is spun into fibers (modified fibroin fibers) by a known spinning method such as wet spinning, dry spinning, dry-wet spinning, or melt spinning. The form of the fiber may be a single yarn, may be a composite yarn such as a blended yarn, a combined filament yarn, a union yarn, a mix-weaved yarn, a piled yarn, and a covering yarn, or may be a nonwoven fabric or the like.

The modified fibroin fiber may be a short fiber or a long fiber. The modified fibroin fiber may also be a modified fibroin fiber alone or may be combined with other fibers. That is, a single yarn composed of only modified fibroin fibers, or a composite yarn composed of a combination of modified fibroin fibers and other fibers may be used singly or in combination. The single yarn and the composite yarn may be spun yarns in which short fibers are twisted, or may be filament yarns in which long fibers are twisted or not twisted. The modified fibroin fiber may be either a short fiber or a long fiber, and may be used as a fiber alone or in combination with another fiber without being processed into a yarn. Examples of the other fiber include synthetic fibers such as nylon and polyester, regenerated fibers such as cupra and rayon, and natural fibers such as cotton and hemp. When the modified fibroin fiber is used in combination with the other fiber, the content of the modified fibroin fiber is preferably 20 mass % or more, more preferably 30 mass % or more, still more preferably 40 mass % or more, and even still more preferably 50 mass % or more, based on the total amount of fibers.

When the water-absorbing and quick-drying property-imparting agent according to the present embodiment is prepared in the form of a film, a gel, a porous body, a particle, or the like, the water-absorbing and quick-drying property-imparting agent can be produced, for example, in accordance with the methods described in JP 2009-505668 A, JP 2009-505668 A, JP 5678283 B2, JP 4638735 B2, and the like.

[Method for Imparting Water-Absorbing and Quick-Drying Properties to Article]

A method for imparting water-absorbing and quick-drying properties to an article according to the present embodiment includes a step of incorporating modified fibroin into the article. Since the modified fibroin according to the present invention is excellent in water-absorbing and quick-drying properties, it is possible to impart water-absorbing and quick-drying properties to an article by incorporating the modified fibroin into the article.

The article is not particularly limited as long as it should impart water-absorbing and quick-drying properties. Specific examples thereof include fibers, woven fabrics, knitted fabrics, nonwoven fabrics, cotton, sponges, films, resins, composite materials (the form of the water-absorbing and quick-drying property-imparting agent according to the present embodiment is not limited), and various articles produced using these materials.

The step of incorporating the modified fibroin may be a step of incorporating the modified fibroin by blending the water-absorbing and quick-drying property-imparting agent according to the present invention described above. The method for incorporating the modified fibroin is not particularly limited, and may be a method of mixing the modified fibroin with the material (raw material), or a method of forming an article by combining the water-absorbing and quick-drying property-imparting agent prepared in the form of the above-described formed body with another material (formed body or the like). Alternatively, a method of forming an article (formed body) by forming modified fibroin itself (other additives may be included as necessary) may be used.

The content of the modified fibroin in the article is preferably 20 mass % or more, more preferably 30 mass % or more, still more preferably 40 mass % or more, and even still more preferably 50 mass % or more, based on the total amount of the article. The upper limit of the content of the modified fibroin may be 100 mass % or 90 mass % or less, based on the total amount of the article. By adjusting the content of the modified fibroin in the article, the water-absorbing and quick-drying properties of the article can be controlled. That is, since the modified fibroin according to the present invention is excellent in water-absorbing and quick-drying properties, the water-absorbing and quick-drying properties of the article can be further enhanced as the content of the modified fibroin in the article is increased.

EXAMPLES

Hereinafter, the present invention will be described more specifically based on Examples and the like. However, the present invention is not limited to the following Examples.
[Production of Modified Fibroin]
(1) Production of Expression Vector Modified fibroin having the amino acid sequence set forth in SEQ ID NO: 37 (PRT918) and modified fibroin having the amino acid sequence shown in SEQ ID NO: 15 (PRT799) were designed. A nucleic acid encoding the designed modified fibroin was synthesized. In the nucleic acid, an NdeI site was added to the 5' end and an EcoRI site was added downstream of the stop codon. The nucleic acid was cloned into a cloning vector (pUC118). Thereafter, the nucleic acid was enzymatically cleaved by treatment with NdeI and EcoRI, and then recombined into a protein expression vector pET-22b(+) to obtain an expression vector.
(2) Expression of Protein

*Escherichia coli* BLR (DE3) was transformed with the obtained expression vector. The transformed *Escherichia coli* was cultured in 2 mL of an LB culture medium containing ampicillin for 15 hours. The culture solution was added to a 100 mL seed culture medium containing ampicillin (Table 4) so that $OD_{600}$ was 0.005. The temperature of the culture solution was maintained at 30° C., and the flask culture was performed (for about 15 hours) until the $OD_{600}$ reached 5, thus obtaining a seed culture solution.

TABLE 4

Seed culture medium

| Reagent | Concentration (g/L) |
| --- | --- |
| Glucose | 5.0 |
| $KH_2PO_4$ | 4.0 |

TABLE 4-continued

Seed culture medium

| Reagent | Concentration (g/L) |
| --- | --- |
| $K_2HPO_4$ | 9.3 |
| Yeast Extract | 6.0 |
| Ampicillin | 0.4 |

The seed culture solution was added to a jar fermenter to which a 500 mL production culture medium (Table 5) was added so that $OD_{600}$ was 0.05. The culture was performed while maintaining the culture solution temperature at 37° C. and constantly controlling the pH to 6.9. Further, the dissolved oxygen concentration in the culture solution was maintained at 20% of the dissolved oxygen saturation concentration.

TABLE 5

Production culture medium

| Reagent | Concentration (g/L) |
| --- | --- |
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| ADEKANOL (Adeka, LG-295S) | 0.1 (mL/L) |

Immediately after glucose in the production culture medium was completely consumed, a feed solution (455 g/1 L of glucose, 120 g/1 L of Yeast Extract) was added at a rate of 1 mL/min. The culture was performed while maintaining the culture solution temperature at 37° C. and constantly controlling the pH to 6.9. Further, the dissolved oxygen concentration in the culture solution was maintained at 20% of the dissolved oxygen saturation concentration, and the culture was performed for 20 hours. Thereafter, 1 M isopropyl-β-thiogalactopyranoside (IPTG) was added to the culture solution to a final concentration of 1 mM to induce the expression of the modified fibroin. The culture solution was centrifuged 20 hours after addition of IPTG, and bacterial cells were recovered. SDS-PAGE was conducted using the bacterial cells prepared from the culture solutions obtained before the addition of IPTG and after the addition of IPTG. The expression of the target modified fibroin which depended on the addition of IPTG was confirmed by the appearance of a band of the size of the target modified fibroin.
(3) Purification of Protein The bacterial cells recovered 2 hours after the addition of IPTG were washed with a 20 mM Tris-HCl buffer (pH 7.4).

The bacterial cells after washing were suspended in a 20 mM Tris-HCl buffer (pH 7.4) containing about 1 mM PMSF and the cells were disrupted with a high-pressure homogenizer (manufactured by GEA Niro Soavi).

The disrupted cells were centrifuged to obtain a precipitate. The obtained precipitate was washed with a 20 mM Tris-HCl buffer (pH 7.4) until the purity of the precipitate became high. The precipitate after washing was suspended in a 8 M guanidine buffer (8 M guanidine hydrochloride, 10 mM sodium dihydrogen phosphate, 20 mM NaCl, 1 mM Tris-HCl, pH 7.0) so that the concentration of the precipitate was 100 mg/mL, and dissolved by stirring with a stirrer for 30 minutes at 60° C. After dissolution, dialysis was performed with water using a dialysis tube (cellulose tube 36/32, manufactured by Sanko Junyaku Co., Ltd.). A white aggregated protein obtained after dialysis was recovered by centrifugation, and moisture was removed in a lyophilizer to recover lyophilized powder, thereby obtaining modified fibroins (PRT918 and PRT799).

PRT918 is hydrophobic modified fibroin having an average HI of more than 0. PRT799 is hydrophilic modified fibroin having an average HI of 0 or less.

[Production of Protein Fiber]

Dimethyl sulfoxide (DMSO) in which LiCl was dissolved so as to be 4.0 mass % was prepared as a solvent, and a lyophilized powder of the modified fibroin was added thereto so as to have a concentration of 24 mass %, and dissolved for 3 hours using a shaker. Thereafter, insoluble matters and foams were removed to obtain a modified fibroin solution (spinning dope).

The prepared spinning dope at 60° C. was filtrated with a metal filter having an opening of 5 μm. Thereafter, the filtrate was allowed to stand in a 30 mL-stainless steel syringe to remove foams. The resulting spinning dope was discharged from a solid nozzle having a needle diameter of 0.2 mm into a 100 mass % methanol coagulation bath. The discharge temperature was 60° C. After completion of the coagulation, the obtained original yarn was wound up, and naturally dried to obtain a modified fibroin fiber (raw material fiber).

For comparison, commercially available silk fibers, cotton fibers, and polyester fibers were prepared as raw material fibers.

[Production of Knitted Fabric]

Knitted fabrics were produced by weft-knitting respective raw material fibers by using a weft-knitting machine. The knitted fabric using PRT918 fibers as raw material fibers had a thickness of 1/30N (metric count, single yarn) and a gauge number of 18. The knitted fabric using PRT799 fibers as raw material fibers had a thickness of 1/30N (metric count, single yarn) and a gauge number of 16. The thickness and gauge number of each of the knitted fabrics formed by using other raw material fibers were adjusted so as to have a cover factor approximately the same as those of the knitted fabrics using PRT918 fibers and PRT799 fibers. Details are as follows.

Silk thickness: 2/60N (single yarn), gauge number: 14
Cotton thickness: 2/34 N (two ply yarn), gauge number: 14
Polyester thickness: 1/60N (single yarn), gauge number: 14

[Evaluation of Water-Absorbing and Quick-Drying Properties]

(Evaluation of Water-Absorbing Properties)

The water-absorbing properties were evaluated by a test in accordance with JIS L 1907 (Testing methods for water-absorbing properties of textiles/dropping method). Specifically, under a standard environment (temperature 20±2° C./humidity 65±4% RH), one drop of water was dropped from the burette onto the surface of the knitted fabric prepared above, and the time until the dropped water droplet was absorbed by the knitted fabric (specular reflection disappeared) was measured (maximum measurement time was 60 seconds). The results are shown in Table 6.

(Evaluation of Quick-Drying Properties)

The quick-drying properties were evaluated by measuring the diffusible residual moisture content. Specifically, under a standard environment (temperature 20±2° C./humidity 65±4% RH), 0.6 mL of tap water was dropped onto the back side of the knitted fabric, and the weight of water was determined by measuring the weight of the knitted fabric at every lapse of a certain time (every 5 minutes), and the diffusible residual moisture content was calculated by the following equation.

Diffusible residual moisture content(%)=weight (g) of water at each time/weight (g) of water at the start of measurement×100

The measurement was performed until the diffusible residual moisture content reached 10% or less (that is, the weight of water reached 10% of 0.6 mL=60 μL (60 mg)), and the time required until the diffusible residual moisture content reached 10% was determined. The results are shown in Table 6.

TABLE 6

|  | Water-absorbing properties (sec) | Rapid-drying properties (min) |
| --- | --- | --- |
| Modified fibroin (PRT918) | >60 | 54 |
| Modified fibroin (PRT799) | 3 | 66 |
| Silk | >60 | 134.3 |
| Cotton | 1 | 125.7 |
| Polyester | >60 | 300.8 |

It can be understood that the modified fibroins (PRT799 and PRT918) are excellent in water-absorbing and quick-drying properties. In particular, it can be understood that the hydrophilic modified fibroin (PRT799) is excellent in both water-absorbing properties and quick-drying properties.

The invention claimed is:

1. A method of imparting water-absorbing and quick-drying properties to an article, the method comprising:
incorporating a water-absorbing and quick-drying property-imparting agent into the article,
wherein the agent comprises modified fibroin as an active ingredient, and
wherein the modified fibroin contains modified spider silk fibroin.

2. The method according to claim 1, wherein the modified fibroin contains modified fibroin having an average value of hydropathy indices (average hydropathy index (HI)) of 0 or less.

3. The method according to claim 1, wherein the agent is in the form of a fiber.

4. The method according to claim 1, wherein the article is selected from the group consisting of fibers, woven fabrics, knitted fabrics, nonwoven fabrics, cotton, sponges, films, resins, and composite materials.

5. The method according to claim 1, wherein the incorporating the agent into the article is performed by mixing the agent with raw material, by forming the article by combining the agent prepared in the form of formed body with another material, or by forming the article by forming the agent.

6. The method according to claim 1, wherein the content of the modified fibroin in the article is 20 mass % or more.

7. The method according to claim 1, wherein the water-absorbing and quick-drying property-imparting agent comprises a modified fibroin including a sequence having at least 90% sequence identity to any one selected from the group consisting of SEQ ID NO: 12-15.

8. The method according to claim 1, the water-absorbing and quick-drying property-imparting agent comprises a modified fibroin including a sequence having at least 90% sequence identity to the amino acid sequence of SEQ ID NO: 15.

9. The method according to claim 1, wherein the water-absorbing and quick-drying property-imparting agent comprises a modified fibroin including a sequence having at least 90% sequence identity to any one selected from the group consisting of SEQ ID NO: 33-44.

10. The method according to claim 1, wherein the water-absorbing and quick-drying property-imparting agent comprises a modified fibroin including a sequence having at least 90% sequence identity to the amino acid sequence of SEQ ID NO: 37.

11. The method according to claim 1, wherein after the incorporating, the article has 60 seconds or less water-absorbing property measured according to JIS L1907.

12. The method according to claim 1, wherein after the incorporating, the article has 5 seconds or less water-absorbing property measured according to JIS L1907.

13. The method according to claim 1, wherein after the incorporating, the article has a diffusible residual moisture content of 100 minutes or less.

14. The method according to claim 1, wherein after the incorporating, the article has a diffusible residual moisture content of 70 minutes or less.

* * * * *

SEQUENCE LISTING

```
<160> NUMBER OF SEQ ID NOS: 44

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45
```

Leu Ala
    50

<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30

<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20

<210> SEQ ID NO 4
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 4

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Ser Ala Ala Ala Ala
        115                 120                 125

Ala Gly Gly Asn Gly Pro Gly Ser Gly Gln Gln Gly Ala Gly Gln Gln
        130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

```
Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
    275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro Gly
                340                 345                 350

Gln Gln Gly Pro Gly Gln Gln Gly Pro Gly Gly Gln Gly Pro Tyr Gly
            355                 360                 365

Pro Gly Ala Ser Ala Ala Ala Ala Ala Gly Gly Tyr Gly Pro Gly
        370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
            435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
                515                 520                 525

Gly Gly Gln Gly Pro Tyr Gly Pro Gly Ala Ala Ser Ala Ala Val Ser
    530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
        595                 600                 605

Gln Gly Pro Tyr Gly Pro Gly Ala Ser Ala Ala Ala Ala Ala Ala Gly
```

-continued

```
            610                 615                 620
Gly Tyr Gly Pro Gly Ser Gly Gln Gln Gly Pro Gly Gln Gly Pro
625                 630                 635                 640

Tyr Gly Pro Gly Ser Ser Ala Ala Ala Ala Ala Gly Gly Asn Gly
                645                 650                 655

Pro Gly Ser Gly Gln Gln Gly Ala Gln Gln Gly Pro Gly Gln Gln
                660                 665                 670

Gly Pro Gly Ala Ser Ala Ala Ala Ala Ala Gly Gly Tyr Gly Pro
            675                 680                 685

Gly Ser Gly Gln Gln Gly Pro Gly Gln Gln Gly Pro Gly Gln Gly
        690                 695                 700

Pro Tyr Gly Pro Gly Ala Ser Ala Ala Ala Ala Ala Gly Gly Tyr
705                 710                 715                 720

Gly Pro Gly Ser Gly Gln Gly Pro Gly Gln Gln Gly Pro Gly Gln
                725                 730                 735

Gly Pro Tyr Gly Pro Gly Ala Ser Ala Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gly Gln Gly Pro Tyr Gly Pro Gly Ala Ser Ala
770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gln Gly Pro Tyr Gly Pro Gly Ala
                805                 810                 815

Ser Ala Ala Ser Ala Ala Ser Gly Gly Tyr Gly Pro Gly Ser Gly Gln
                820                 825                 830

Gln Gly Pro Gly Gln Gln Gly Pro Gly Gln Gly Pro Tyr Gly Pro
            835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
                885                 890                 895

Ala Ala Ala Ala Gly Gly Tyr Gly Pro Gly Ser Gly Gln Gln Gly
                900                 905                 910

Pro Gly Gln Gln Gly Pro Gly Gln Gln Gly Pro Gly Gln Gln Gly Pro
915                 920                 925

Gly Gln Gln Gly Pro Gly Gln Gln Gly Pro Gly Gln Gln Gly Pro Gly
930                 935                 940

Gln Gln Gly Pro Gly Gln Gln Gly Pro Gly Gln Gly Ala Tyr Gly
945                 950                 955                 960

Pro Gly Ala Ser Ala Ala Ala Gly Ala Ala Gly Gly Tyr Gly Pro Gly
                965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
        995                 1000                1005

Gln Gln Gly Pro Gly Gln Gln Gly Pro Tyr Gly Pro Gly Ala Ser
    1010                1015                1020

Ala Ala Ala Ala Ala Ala Gly Gly Tyr Gly Pro Gly Ser Gly Gln
    1025                1030                1035
```

```
Gln Gly Pro Gly Gln Gln Gly Pro Gly Gln Gln Gly Pro Gly Gly
        1040                1045                1050

Gln Gly Pro Tyr Gly Pro Gly Ala Ala Ser Ala Ala Val Ser Val
        1055                1060                1065

Gly Gly Tyr Gly Pro Gln Ser Ser Ser Val Pro Val Ala Ser Ala
        1070                1075                1080

Val Ala Ser Arg Leu Ser Ser Pro Ala Ala Ser Ser Arg Val Ser
        1085                1090                1095

Ser Ala Val Ser Ser Leu Val Ser Ser Gly Pro Thr Lys His Ala
        1100                1105                1110

Ala Leu Ser Asn Thr Ile Ser Ser Val Val Ser Gln Val Ser Ala
        1115                1120                1125

Ser Asn Pro Gly Leu Ser Gly Cys Asp Val Leu Val Gln Ala Leu
        1130                1135                1140

Leu Glu Val Val Ser Ala Leu Val Ser Ile Leu
        1145                1150

<210> SEQ ID NO 5
<211> LENGTH: 24
<212> TYPE: PRT
<213> ORGANISM: Artificial Sequence
<220> FEATURE:
<223> OTHER INFORMATION: His tag and start codon

<400> SEQUENCE: 5

Met His His His His His His His His His Ser Ser Gly Ser Ser
1               5                   10                  15

Leu Glu Val Leu Phe Gln Gly Pro
            20

<210> SEQ ID NO 6
<211> LENGTH: 597
<212> TYPE: PRT
<213> ORGANISM: Artificial Sequence
<220> FEATURE:
<223> OTHER INFORMATION: Met-PRT380

<400> SEQUENCE: 6

Met Gly Pro Gly Gln Gln Gly Pro Tyr Gly Pro Gly Ala Ser Ala
1               5                   10                  15

Ala Ala Ala Gly Gln Asn Gly Pro Gly Ser Gly Gln Gln Gly Pro
                20                  25                  30

Gly Gln Ser Ala Ala Ala Ala Gly Gln Tyr Gly Pro Gly Gln Gln
            35                  40                  45

Pro Gly Gln Gln Gly Pro Gly Ser Ser Ala Ala Ala Ala Gly Pro
        50                  55                  60

Gly Gln Tyr Gly Pro Gly Gln Gln Gly Pro Ser Ala Ser Ala Ala
65                  70                  75                  80

Ala Ala Gly Pro Gly Ser Gly Gln Gln Gly Pro Gly Ala Ser Ala
                85                  90                  95

Ala Ala Ala Gly Gln Tyr Gly Pro Gly Gln Gln Gly Pro Gly Gln
            100                 105                 110

Gly Pro Gly Ser Ser Ala Ala Ala Ala Gly Gln Tyr Gly Ser Gly
        115                 120                 125

Pro Gly Gln Gln Gly Pro Tyr Gly Ser Ala Ala Ala Ala Gly Pro
        130                 135                 140

Gly Ser Gly Gln Tyr Gly Gln Gly Pro Tyr Gly Pro Gly Ala Ser Ala
```

```
               145                 150                 155                 160
      Ala Ala Ala Ala Gly Pro Gly Gln Tyr Gly Pro Gly Gln Gln Gly Pro
                       165                 170                 175

Ser Ala Ser Ala Ala Ala Ala Ala Gly Ser Gln Gln Gly Pro Gly
                       180                 185                 190

Gln Tyr Gly Pro Tyr Ala Ser Ala Ala Ala Ala Gly Gln Tyr Gly
                       195                 200                 205

Ser Gly Pro Gly Gln Gly Pro Tyr Gly Pro Gly Gln Ser Ala Ala
                       210                 215                 220

Ala Ala Ala Gly Ser Gly Gln Gln Gly Pro Gly Gln Gln Gly Pro Tyr
      225                 230                 235                 240

Ala Ser Ala Ala Ala Ala Ala Gly Pro Gly Gln Gln Gly Pro Tyr Gly
                       245                 250                 255

Pro Gly Ser Ser Ala Ala Ala Ala Gly Gln Tyr Gly Tyr Gly Pro
                       260                 265                 270

Gly Gln Gln Gly Pro Tyr Gly Pro Gly Ala Ser Ala Ala Ala Ala
                       275                 280                 285

Gly Gln Asn Gly Pro Gly Ser Gly Gln Tyr Gly Pro Gly Gln Gln Gly
                       290                 295                 300

Pro Gly Gln Ser Ala Ala Ala Ala Gly Pro Gly Gln Gln Gly Pro
      305                 310                 315                 320

Tyr Gly Pro Gly Ala Ser Ala Ala Ala Ala Gly Gln Tyr Gly Pro
                       325                 330                 335

Gly Gln Gln Gly Pro Gly Gln Tyr Gly Pro Gly Ser Ser Ala Ala
                       340                 345                 350

Ala Ala Gly Pro Gly Gln Gln Gly Pro Tyr Gly Pro Gly Ser Ser Ala
                       355                 360                 365

Ala Ala Ala Gly Gln Tyr Gly Pro Gly Gln Gln Gly Pro Tyr Gly
                       370                 375                 380

Pro Gly Gln Ser Ala Ala Ala Ala Gly Gln Tyr Gln Gln Gly Pro
      385                 390                 395                 400

Gly Gln Gln Gly Pro Tyr Gly Pro Gly Ala Ser Ala Ala Ala Ala
                       405                 410                 415

Gly Pro Gly Gln Gln Gly Pro Tyr Gly Pro Gly Ala Ser Ala Ala Ala
                       420                 425                 430

Ala Ala Gly Pro Gly Gln Tyr Gly Pro Gly Gln Gly Pro Ser Ala
                       435                 440                 445

Ser Ala Ala Ala Ala Gly Gln Tyr Gly Ser Gly Pro Gly Gln Tyr
                       450                 455                 460

Gly Pro Tyr Gly Pro Gly Gln Ser Ala Ala Ala Ala Ala Gly Pro Gly
      465                 470                 475                 480

Ser Gly Gln Gln Gly Gln Pro Tyr Gly Pro Gly Ala Ser Ala Ala
                       485                 490                 495

Ala Ala Ala Gly Gln Tyr Gly Pro Gly Gln Gln Gly Pro Tyr Gly Pro
                       500                 505                 510

Gly Gln Ser Ala Ala Ala Ala Ala Gly Pro Gly Ser Gly Gln Tyr Gly
                       515                 520                 525

Pro Gly Ala Ser Ala Ala Ala Ala Gly Gln Asn Gly Pro Gly Ser
                       530                 535                 540

Gly Gln Tyr Gly Pro Gly Gln Gly Pro Gln Ser Ala Ala
      545                 550                 555                 560

Ala Ala Gly Gln Tyr Gln Gln Gly Pro Gly Gln Gly Pro Tyr Gly
                       565                 570                 575
```

```
Pro Gly Ala Ser Ala Ala Ala Ala Gly Pro Gly Ser Gly Gln Gln
            580                 585                 590

Gly Pro Gly Ala Ser
        595

<210> SEQ ID NO 7
<211> LENGTH: 590
<212> TYPE: PRT
<213> ORGANISM: Artificial Sequence
<220> FEATURE:
<223> OTHER INFORMATION: Met-PRT410

<400> SEQUENCE: 7

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gln Gln Gly Pro Gly
            20                  25                  30

Gln Ser Gly Gln Tyr Gly Pro Gly Gln Gln Pro Gly Gln Gln Gly
        35                  40                  45

Pro Gly Ser Ser Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
            165                 170                 175

Gly Gln Tyr Gly Pro Tyr Ala Ser Ala Ala Ala Ala Gly Gln Tyr
        180                 185                 190

Gly Ser Gly Pro Gly Gln Gln Gly Pro Tyr Gly Pro Gln Ser Gly
    195                 200                 205

Ser Gly Gln Gln Gly Pro Gly Gln Gln Gly Pro Tyr Ala Ser Ala Ala
210                 215                 220

Ala Ala Ala Gly Pro Gly Gln Gln Gly Pro Tyr Gly Pro Gly Ser Ser
225                 230                 235                 240

Ala Ala Ala Ala Gly Gln Tyr Gly Tyr Gly Pro Gly Gln Gln Gly
            245                 250                 255

Pro Tyr Gly Pro Gly Ala Ser Gly Gln Asn Gly Pro Gly Ser Gly Gln
        260                 265                 270

Tyr Gly Pro Gly Gln Gln Gly Pro Gly Gln Ser Ala Ala Ala Ala
    275                 280                 285

Gly Pro Gly Gln Gln Gly Pro Tyr Gly Pro Gly Ala Ser Ala Ala Ala
290                 295                 300

Ala Ala Gly Gln Tyr Gly Pro Gly Gln Gln Pro Gly Gln Tyr Gly
            305                 310                 315                 320

Pro Gly Ser Ser Gly Pro Gly Gln Gln Gly Pro Tyr Gly Pro Gly Ser
        325                 330                 335
```

Ser Ala Ala Ala Ala Gly Gln Tyr Gly Pro Gly Gln Gln Gly Pro
        340                 345                 350

Tyr Gly Pro Gly Gln Ser Ala Ala Ala Gly Gln Tyr Gln Gln
        355                 360                 365

Gly Pro Gly Gln Gln Gly Pro Tyr Gly Pro Gly Ala Ser Gly Pro Gly
370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gln Gly Pro Ser Ala Ser Ala Ala
            405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
            435                 440                 445

Tyr Gly Pro Gly Ala Ser Ala Ala Ala Ala Gly Gln Tyr Gly Pro
        450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
            485                 490                 495

Pro Gly Ser Gly Gln Tyr Gly Pro Gly Gln Gln Gly Pro Gly Gln Ser
            500                 505                 510

Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Gly Gln Tyr Gly
        530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
            565                 570                 575

Ala Ala Gly Pro Gly Ser Gly Gln Gln Gly Pro Gly Ala Ser
        580                 585                 590

<210> SEQ ID NO 8
<211> LENGTH: 565
<212> TYPE: PRT
<213> ORGANISM: Artificial Sequence
<220> FEATURE:
<223> OTHER INFORMATION: Met-PRT525

<400> SEQUENCE: 8

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gln Gln Gly
            20                  25                  30

Pro Gly Gln Ser Gly Tyr Gly Pro Gly Gln Gly Pro Gly Gln
        35                  40                  45

Gln Gly Pro Gly Ser Ser Ala Ala Ala Ala Ala Ala Gly Pro Gly
    50                  55                  60

Gln Tyr Gly Pro Gly Gln Gln Pro Ser Ala Ser Ala Ala Ala
65                  70                  75                  80

Ala Ala Ala Gly Pro Gly Ser Gly Gln Gln Gly Pro Gly Ala Ser Gly
            85                  90                  95

Gln Tyr Gly Pro Gly Gln Gln Gly Pro Gly Gln Gln Gly Pro Gly Ser
            100                 105                 110

```
Ser Ala Ala Ala Ala Ala Ala Gly Ser Tyr Gly Ser Pro Gly
    115                 120                 125

Gln Gln Gly Pro Tyr Gly Ser Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Gly Ser Tyr Gly Ser
        195                 200                 205

Gly Pro Gly Gln Gln Gly Pro Tyr Gly Pro Gly Gln Ser Gly Ser Gly
    210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
            245                 250                 255

Ala Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
        275                 280                 285

Gly Gln Tyr Gly Pro Gly Gln Gln Gly Pro Gly Pro Ser Ala Ala Ala
    290                 295                 300

Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
        325                 330                 335

Gly Pro Gly Gln Tyr Gly Pro Gly Ser Ser Gly Pro Gly Gln Gln Gly
    340                 345                 350

Pro Tyr Gly Pro Gly Ser Ser Ala Ala Ala Ala Ala Ala Gly Ser
        355                 360                 365

Tyr Gly Pro Gly Gln Gln Gly Pro Tyr Gly Pro Gly Pro Ser Ala Ala
    370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
        405                 410                 415

Pro Gly Ala Ser Ala Ala Ala Ala Ala Ala Gly Pro Gly Gln Tyr
        420                 425                 430

Gly Pro Gly Gln Gln Gly Pro Ser Ala Ser Ala Ala Ala Ala
    435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Gln Gln Gly Gln Pro Gly Tyr Gly
465                 470                 475                 480

Pro Gly Ala Ser Ala Ala Ala Ala Ala Ala Gly Ser Tyr Gly Pro
        485                 490                 495

Gly Gln Gln Gly Pro Tyr Gly Pro Gly Pro Ser Ala Ala Ala Ala
        500                 505                 510

Ala Ala Gly Pro Gly Ser Gly Gln Tyr Gly Pro Gly Ala Ser Gly Gln
        515                 520                 525
```

-continued

```
Asn Gly Pro Gly Ser Gly Gln Tyr Gly Pro Gly Gln Gly Pro Gly
            530                 535                 540
Pro Ser Ala Ala Ala Ala Ala Ala Gly Pro Gly Ser Gly Gln Gln
545                 550                 555                 560
Gly Pro Gly Ala Ser
            565

<210> SEQ ID NO 9
<211> LENGTH: 2364
<212> TYPE: PRT
<213> ORGANISM: Artificial Sequence
<220> FEATURE:
<223> OTHER INFORMATION: Met-PRT799

<400> SEQUENCE: 9

Met Gly Pro Gly Gln Gln Gly Pro Tyr Gly Pro Gly Ala Ser Ala Ala
1               5                   10                  15
Ala Ala Ala Gly Gln Asn Gly Pro Gly Ser Gly Gln Gln Gly Pro Gly
            20                  25                  30
Gln Ser Gly Gln Tyr Gly Pro Gly Gln Gln Gly Pro Gly Gln Gln Gly
        35                  40                  45
Pro Gly Ser Ser Ala Ala Ala Ala Gly Pro Gly Gln Tyr Gly Pro
50                  55                  60
Gly Gln Gln Gly Pro Ser Ala Ser Ala Ala Ala Ala Gly Pro Gly
65                  70                  75                  80
Ser Gly Gln Gln Gly Pro Gly Ala Ser Gly Gln Tyr Gly Pro Gly Gln
                85                  90                  95
Gln Gly Pro Gly Gln Gln Gly Pro Gly Ser Ser Ala Ala Ala Ala
            100                 105                 110
Gly Gln Tyr Gly Ser Gly Pro Gly Gln Gln Gly Pro Tyr Gly Ser Ala
        115                 120                 125
Ala Ala Ala Ala Gly Pro Gly Ser Gly Gln Tyr Gly Gln Gly Pro Tyr
130                 135                 140
Gly Pro Gly Ala Ser Gly Pro Gly Gln Tyr Gly Pro Gly Gln Gln Gly
145                 150                 155                 160
Pro Ser Ala Ser Ala Ala Ala Ala Gly Ser Gly Gln Gln Gly Pro
            165                 170                 175
Gly Gln Tyr Gly Pro Tyr Ala Ser Ala Ala Ala Ala Gly Gln Tyr
        180                 185                 190
Gly Ser Gly Pro Gly Gln Gln Gly Pro Tyr Gly Pro Gly Gln Ser Gly
    195                 200                 205
Ser Gly Gln Gln Gly Pro Gly Gln Gly Pro Tyr Ala Ser Ala Ala
    210                 215                 220
Ala Ala Ala Gly Pro Gly Gln Gln Gly Pro Tyr Gly Pro Gly Ser Ser
225                 230                 235                 240
Ala Ala Ala Ala Ala Gly Gln Tyr Gly Tyr Gly Pro Gly Gln Gln Gly
                245                 250                 255
Pro Tyr Gly Pro Gly Ala Ser Gly Gln Asn Gly Pro Gly Ser Gly Gln
            260                 265                 270
Tyr Gly Pro Gly Gln Gln Gly Pro Gly Gln Ser Ala Ala Ala Ala
        275                 280                 285
Gly Pro Gly Gln Gln Gly Pro Tyr Gly Pro Gly Ala Ser Ala Ala
    290                 295                 300
Ala Ala Gly Gln Tyr Gly Pro Gly Gln Gln Gly Pro Gly Gln Tyr Gly
305                 310                 315                 320
```

```
Pro Gly Ser Ser Gly Pro Gly Gln Gln Gly Pro Tyr Gly Pro Gly Ser
                325                 330                 335

Ser Ala Ala Ala Ala Ala Gly Gln Tyr Gly Pro Gly Gln Gln Gly Pro
                340                 345                 350

Tyr Gly Pro Gly Gln Ser Ala Ala Ala Ala Gly Gln Tyr Gln Gln
            355                 360                 365

Gly Pro Gly Gln Gln Gly Pro Tyr Gly Pro Gly Ala Ser Gly Pro Gly
        370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Gly Gln Tyr Gly Pro
            450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
                500                 505                 510

Ala Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser Gly Gln
            580                 585                 590

Gln Gly Pro Tyr Gly Pro Gly Ala Ser Ala Ala Ala Ala Gly Gln
        595                 600                 605

Asn Gly Pro Gly Ser Gly Gln Gln Gly Pro Gly Gln Ser Gly Gln Tyr
610                 615                 620

Gly Pro Gly Gln Gln Gly Pro Gly Gln Gln Gly Pro Gly Ser Ser Ala
                625                 630                 635                 640

Ala Ala Ala Gly Pro Gly Gln Tyr Gly Pro Gly Gln Gln Gly Pro
            645                 650                 655

Ser Ala Ser Ala Ala Ala Ala Ala Gly Pro Gly Ser Gly Gln Gln Gly
            660                 665                 670

Pro Gly Ala Ser Gly Gln Tyr Gly Pro Gly Gln Gln Gly Pro Gly Gln
        675                 680                 685

Gln Gly Pro Gly Ser Ser Ala Ala Ala Ala Gly Gln Tyr Gly Ser
690                 695                 700

Gly Pro Gly Gln Gln Gly Pro Tyr Gly Ser Ala Ala Ala Ala Gly
705                 710                 715                 720

Pro Gly Ser Gly Gln Tyr Gly Gln Gly Pro Tyr Gly Pro Gly Ala Ser
            725                 730                 735

Gly Pro Gly Gln Tyr Gly Pro Gly Gln Gln Gly Pro Ser Ala Ser Ala
```

```
            740                 745                 750
Ala Ala Ala Ala Gly Ser Gly Gln Gln Gly Pro Gly Gln Tyr Gly Pro
                755                 760                 765

Tyr Ala Ser Ala Ala Ala Ala Gly Gln Tyr Gly Ser Gly Pro Gly
        770                 775                 780

Gln Gln Gly Pro Tyr Gly Pro Gly Gln Ser Gly Ser Gly Gln Gln Gly
785                 790                 795                 800

Pro Gly Gln Gln Gly Pro Tyr Ala Ser Ala Ala Ala Ala Gly Pro
                805                 810                 815

Gly Gln Gln Gly Pro Tyr Gly Pro Gly Ser Ser Ala Ala Ala Ala
                820                 825                 830

Gly Gln Tyr Gly Tyr Gly Pro Gly Gln Gln Gly Pro Tyr Gly Pro Gly
        835                 840                 845

Ala Ser Gly Gln Asn Gly Pro Gly Ser Gly Gln Tyr Gly Pro Gly Gln
        850                 855                 860

Gln Gly Pro Gly Gln Ser Ala Ala Ala Ala Gly Pro Gly Gln Gln
865                 870                 875                 880

Gly Pro Tyr Gly Pro Gly Ala Ser Ala Ala Ala Ala Gly Gln Tyr
                885                 890                 895

Gly Pro Gly Gln Gln Gly Pro Gly Gln Tyr Gly Pro Gly Ser Ser Gly
                900                 905                 910

Pro Gly Gln Gln Gly Pro Tyr Gly Pro Gly Ser Ser Ala Ala Ala Ala
        915                 920                 925

Ala Gly Gln Tyr Gly Pro Gly Gln Gln Gly Pro Tyr Gly Pro Gly Gln
        930                 935                 940

Ser Ala Ala Ala Ala Gly Gln Tyr Gln Gln Gly Pro Gly Gln Gln
945                 950                 955                 960

Gly Pro Tyr Gly Pro Gly Ala Ser Gly Pro Gly Gln Gln Gly Pro Tyr
                965                 970                 975

Gly Pro Gly Ala Ser Ala Ala Ala Ala Gly Pro Gly Gln Tyr Gly
                980                 985                 990

Pro Gly Gln Gln Gly Pro Ser Ala Ser Ala Ala Ala Ala Gly Gln
        995                 1000                1005

Tyr Gly Ser Gly Pro Gly Gln Tyr Gly Pro Tyr Gly Pro Gly Gln
        1010                1015                1020

Ser Gly Pro Gly Ser Gly Gln Gln Gly Gln Gly Pro Tyr Gly Pro
        1025                1030                1035

Gly Ala Ser Ala Ala Ala Ala Gly Gln Tyr Gly Pro Gly Gln
        1040                1045                1050

Gln Gly Pro Tyr Gly Pro Gly Gln Ser Ala Ala Ala Ala Ala Gly
        1055                1060                1065

Pro Gly Ser Gly Gln Tyr Gly Pro Gly Ala Ser Gly Gln Asn Gly
        1070                1075                1080

Pro Gly Ser Gly Gln Tyr Gly Pro Gly Gln Gln Gly Pro Gly Gln
        1085                1090                1095

Ser Ala Ala Ala Ala Ala Gly Gln Tyr Gln Gln Gly Pro Gly Gln
        1100                1105                1110

Gln Gly Pro Tyr Gly Pro Gly Ala Ser Ala Ala Ala Ala Ala Gly
        1115                1120                1125

Gln Tyr Gly Ser Gly Pro Gly Gln Gln Gly Pro Tyr Gly Pro Gly
        1130                1135                1140

Gln Ser Gly Ser Gly Gln Gln Gly Pro Gly Gln Gln Gly Pro Tyr
        1145                1150                1155
```

```
Ala Ser  Ala Ala Ala Ala  Ala Gly Pro Gly  Ser Gly Gln Gln Gly
    1160             1165              1170

Pro Gly  Ala Ser Gly Gln  Gln Gly Pro Tyr  Gly Pro Gly Ala Ser
    1175             1180              1185

Ala Ala  Ala Ala Ala Gly  Gln Asn Gly Pro  Gly Ser Gly Gln Gln
    1190             1195              1200

Gly Pro  Gly Gln Ser Gly  Gln Tyr Gly Pro  Gly Gln Gln Gly Pro
    1205             1210              1215

Gly Gln  Gln Gly Pro Gly  Ser Ser Ala Ala  Ala Ala Ala Gly Pro
    1220             1225              1230

Gly Gln  Tyr Gly Pro Gly  Gln Gln Gly Pro  Ser Ala Ser Ala Ala
    1235             1240              1245

Ala Ala  Ala Gly Pro Gly  Ser Gly Gln Gln  Gly Pro Gly Ala Ser
    1250             1255              1260

Gly Gln  Tyr Gly Pro Gly  Gln Gln Gly Pro  Gly Gln Gln Gly Pro
    1265             1270              1275

Gly Ser  Ser Ala Ala Ala  Ala Ala Gly Gln  Tyr Gly Ser Gly Pro
    1280             1285              1290

Gly Gln  Gln Gly Pro Tyr  Gly Ser Ala Ala  Ala Ala Ala Gly Pro
    1295             1300              1305

Gly Ser  Gly Gln Tyr Gly  Gln Gly Pro Tyr  Gly Pro Gly Ala Ser
    1310             1315              1320

Gly Pro  Gly Gln Tyr Gly  Pro Gly Gln Gly  Pro Ser Ala Ser
    1325             1330              1335

Ala Ala  Ala Ala Ala Gly  Ser Gly Gln Gln  Gly Pro Gly Gln Tyr
    1340             1345              1350

Gly Pro  Tyr Ala Ser Ala  Ala Ala Ala Ala  Gly Gln Tyr Gly Ser
    1355             1360              1365

Gly Pro  Gly Gln Gln Gly  Pro Tyr Gly Pro  Gly Gln Ser Gly Ser
    1370             1375              1380

Gly Gln  Gln Gly Pro Gly  Gln Gln Gly Pro  Tyr Ala Ser Ala Ala
    1385             1390              1395

Ala Ala  Ala Gly Pro Gly  Gln Gln Gly Pro  Tyr Gly Pro Gly Ser
    1400             1405              1410

Ser Ala  Ala Ala Ala Ala  Gly Gln Tyr Gly  Tyr Gly Pro Gly Gln
    1415             1420              1425

Gln Gly  Pro Tyr Gly Pro  Gly Ala Ser Gly  Gln Asn Gly Pro Gly
    1430             1435              1440

Ser Gly  Gln Tyr Gly Pro  Gly Gln Gln Gly  Pro Gly Gln Ser Ala
    1445             1450              1455

Ala Ala  Ala Ala Gly Pro  Gly Gln Gln Gly  Pro Tyr Gly Pro Gly
    1460             1465              1470

Ala Ser  Ala Ala Ala Ala  Gly Gln Tyr Gly  Pro Gly Gln Gln
    1475             1480              1485

Gly Pro  Gly Gln Tyr Gly  Pro Gly Ser Ser  Gly Pro Gly Gln Gln
    1490             1495              1500

Gly Pro  Tyr Gly Pro Gly  Ser Ser Ala Ala  Ala Ala Gly Gln
    1505             1510              1515

Tyr Gly  Pro Gly Gln Gln  Gly Pro Tyr Gly  Pro Gly Gln Ser Ala
    1520             1525              1530

Ala Ala  Ala Ala Gly Gln  Tyr Gln Gln Gly  Pro Gly Gln Gln Gly
    1535             1540              1545
```

-continued

```
Pro Tyr Gly Pro Gly Ala Ser Gly Pro Gly Gln Gln Gly Pro Tyr
    1550                1555                1560

Gly Pro Gly Ala Ser Ala Ala Ala Ala Ala Gly Pro Gly Gln Tyr
    1565                1570                1575

Gly Pro Gly Gln Gln Gly Pro Ser Ala Ser Ala Ala Ala Ala Ala
    1580                1585                1590

Gly Gln Tyr Gly Ser Gly Pro Gly Gln Tyr Gly Pro Tyr Gly Pro
    1595                1600                1605

Gly Gln Ser Gly Pro Gly Ser Gly Gln Gln Gly Gln Gly Pro Tyr
    1610                1615                1620

Gly Pro Gly Ala Ser Ala Ala Ala Ala Ala Gly Gln Tyr Gly Pro
    1625                1630                1635

Gly Gln Gln Gly Pro Tyr Gly Pro Gly Gln Ser Ala Ala Ala Ala
    1640                1645                1650

Ala Gly Pro Gly Ser Gly Gln Tyr Gly Pro Gly Ala Ser Gly Gln
    1655                1660                1665

Asn Gly Pro Gly Ser Gly Gln Tyr Gly Pro Gly Gln Gln Gly Pro
    1670                1675                1680

Gly Gln Ser Ala Ala Ala Ala Ala Gly Gln Tyr Gln Gln Gly Pro
    1685                1690                1695

Gly Gln Gln Gly Pro Tyr Gly Pro Gly Ala Ser Ala Ala Ala Ala
    1700                1705                1710

Ala Gly Gln Tyr Gly Ser Gly Pro Gly Gln Gln Gly Pro Tyr Gly
    1715                1720                1725

Pro Gly Gln Ser Gly Ser Gly Gln Gln Gly Pro Gly Gln Gln Gly
    1730                1735                1740

Pro Tyr Ala Ser Ala Ala Ala Ala Ala Gly Pro Gly Ser Gly Gln
    1745                1750                1755

Gln Gly Pro Gly Ala Ser Gly Gln Gln Gly Pro Tyr Gly Pro Gly
    1760                1765                1770

Ala Ser Ala Ala Ala Ala Ala Gly Gln Asn Gly Pro Gly Ser Gly
    1775                1780                1785

Gln Gln Gly Pro Gly Gln Ser Gly Gln Tyr Gly Pro Gly Gln Gln
    1790                1795                1800

Gly Pro Gly Gln Gln Gly Pro Gly Ser Ser Ala Ala Ala Ala Ala
    1805                1810                1815

Gly Pro Gly Gln Tyr Gly Pro Gly Gln Gly Pro Ser Ala Ser
    1820                1825                1830

Ala Ala Ala Ala Ala Gly Pro Gly Ser Gly Gln Gln Gly Pro Gly
    1835                1840                1845

Ala Ser Gly Gln Tyr Gly Pro Gly Gln Gln Gly Pro Gly Gln Gln
    1850                1855                1860

Gly Pro Gly Ser Ser Ala Ala Ala Ala Ala Gly Gln Tyr Gly Ser
    1865                1870                1875

Gly Pro Gly Gln Gln Gly Pro Tyr Gly Ser Ala Ala Ala Ala Ala
    1880                1885                1890

Gly Pro Gly Ser Gly Gln Tyr Gly Gln Gly Pro Tyr Gly Pro Gly
    1895                1900                1905

Ala Ser Gly Pro Gly Gln Tyr Gly Pro Gly Gln Gln Gly Pro Ser
    1910                1915                1920

Ala Ser Ala Ala Ala Ala Ala Gly Ser Gly Gln Gln Gly Pro Gly
    1925                1930                1935

Gln Tyr Gly Pro Tyr Ala Ser Ala Ala Ala Ala Ala Gly Gln Tyr
```

-continued

|                                                                          |
|                 1940              1945              1950                 |

Gly Ser Gly Pro Gly Gln Gln Gly Pro Tyr Gly Pro Gly Gln Ser
            1955              1960              1965

Gly Ser Gly Gln Gln Gly Pro Gly Gln Gln Gly Pro Tyr Ala Ser
            1970              1975              1980

Ala Ala Ala Ala Ala Gly Pro Gly Gln Gln Gly Pro Tyr Gly Pro
            1985              1990              1995

Gly Ser Ser Ala Ala Ala Ala Gly Gln Tyr Gly Tyr Gly Pro
            2000              2005              2010

Gly Gln Gln Gly Pro Tyr Gly Pro Gly Ala Ser Gly Gln Asn Gly
            2015              2020              2025

Pro Gly Ser Gly Gln Tyr Gly Pro Gly Gln Gln Gly Pro Gly Gln
            2030              2035              2040

Ser Ala Ala Ala Ala Ala Gly Pro Gly Gln Gln Gly Pro Tyr Gly
            2045              2050              2055

Pro Gly Ala Ser Ala Ala Ala Ala Gly Gln Tyr Gly Pro Gly
            2060              2065              2070

Gln Gln Gly Pro Gly Gln Tyr Gly Pro Gly Ser Ser Gly Pro Gly
            2075              2080              2085

Gln Gln Gly Pro Tyr Gly Pro Gly Ser Ser Ala Ala Ala Ala Ala
            2090              2095              2100

Gly Gln Tyr Gly Pro Gly Gln Gln Gly Pro Tyr Gly Pro Gly Gln
            2105              2110              2115

Ser Ala Ala Ala Ala Gly Gln Tyr Gln Gln Gly Pro Gly Gln
            2120              2125              2130

Gln Gly Pro Tyr Gly Pro Gly Ala Ser Gly Pro Gly Gln Gln Gly
            2135              2140              2145

Pro Tyr Gly Pro Gly Ala Ser Ala Ala Ala Ala Gly Pro Gly
            2150              2155              2160

Gln Tyr Gly Pro Gly Gln Gln Gly Pro Ser Ala Ser Ala Ala Ala
            2165              2170              2175

Ala Ala Gly Gln Tyr Gly Ser Gly Pro Gly Gln Tyr Gly Pro Tyr
            2180              2185              2190

Gly Pro Gly Gln Ser Gly Pro Gly Ser Gly Gln Gln Gly Gln Gly
            2195              2200              2205

Pro Tyr Gly Pro Gly Ala Ser Ala Ala Ala Ala Gly Gln Tyr
            2210              2215              2220

Gly Pro Gly Gln Gln Gly Pro Tyr Gly Pro Gly Gln Ser Ala Ala
            2225              2230              2235

Ala Ala Ala Gly Pro Gly Ser Gly Gln Tyr Gly Pro Gly Ala Ser
            2240              2245              2250

Gly Gln Asn Gly Pro Gly Ser Gly Gln Tyr Gly Pro Gly Gln Gln
            2255              2260              2265

Gly Pro Gly Gln Ser Ala Ala Ala Ala Ala Gly Gln Tyr Gln Gln
            2270              2275              2280

Gly Pro Gly Gln Gln Gly Pro Tyr Gly Pro Gly Ala Ser Ala Ala
            2285              2290              2295

Ala Ala Ala Gly Gln Tyr Gly Ser Gly Pro Gly Gln Gln Gly Pro
            2300              2305              2310

Tyr Gly Pro Gly Gln Ser Gly Ser Gly Gln Gln Gly Pro Gly Gln
            2315              2320              2325

Gln Gly Pro Tyr Ala Ser Ala Ala Ala Ala Ala Gly Pro Gly Ser
            2330              2335              2340

Gly Gln Gln Gly Ser Ser Val Asp Lys Leu Ala Ala Ala Leu Glu
        2345                2350                2355

His His His His His His
        2360

<210> SEQ ID NO 10
<211> LENGTH: 597
<212> TYPE: PRT
<213> ORGANISM: Artificial Sequence
<220> FEATURE:
<223> OTHER INFORMATION: Met-PRT313

<400> SEQUENCE: 10

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gln Gln Gly Pro Gly Gly
            20                  25                  30

Gly Ser Ala Ala Ala Ala Ala Gly Gly Tyr Gly Pro Gly Gly Gln Gly
        35                  40                  45

Pro Gly Gln Gln Gly Pro Gly Ser Ala Ala Ala Ala Ala Ala Gly Pro
    50                  55                  60

Gly Gly Tyr Gly Pro Gly Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gly Tyr Gly Pro Gly Gly Gln Gly Pro Gly Gln Gln
            100                 105                 110

Gly Pro Gly Ser Ser Ala Ala Ala Ala Gly Gly Tyr Gly Ser Gly
        115                 120                 125

Pro Gly Gln Gln Gly Pro Tyr Gly Ser Ala Ala Ala Ala Gly Pro
    130                 135                 140

Gly Ser Gly Gly Tyr Gly Gln Gly Pro Tyr Gly Pro Gly Ala Ser Ala
145                 150                 155                 160

Ala Ala Ala Gly Pro Gly Gly Tyr Gly Pro Gly Gly Gln Gly Pro
                165                 170                 175

Ser Ala Ser Ala Ala Ala Ala Gly Ser Gly Gln Gln Gly Pro Gly
            180                 185                 190

Gly Tyr Gly Pro Tyr Ala Ser Ala Ala Ala Ala Gly Gly Tyr Gly
        195                 200                 205

Ser Gly Pro Gly Gln Gln Gly Pro Tyr Gly Pro Gly Gly Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gly Gln Gly Pro Tyr Gly
                245                 250                 255

Pro Gly Ser Ser Ala Ala Ala Ala Gly Gly Tyr Gly Tyr Gly Pro
            260                 265                 270

Gly Gly Gln Gly Pro Tyr Gly Pro Gly Ala Ser Ala Ala Ala Ala Ala
        275                 280                 285

Gly Gly Asn Gly Pro Gly Ser Gly Gly Tyr Gly Pro Gly Gln Gln Gly
    290                 295                 300

Pro Gly Gly Ser Ala Ala Ala Ala Gly Pro Gly Gly Gln Gly Pro
305                 310                 315                 320

Tyr Gly Pro Gly Ala Ser Ala Ala Ala Ala Gly Gly Tyr Gly Pro
                325                 330                 335

Gly Gly Gln Gly Pro Gly Tyr Gly Pro Gly Ser Ser Ala Ala Ala
            340                 345                 350

Ala Ala Gly Pro Gly Gly Gln Gly Pro Tyr Gly Pro Gly Ser Ser Ala
            355                 360                 365

Ala Ala Ala Ala Gly Gly Tyr Gly Pro Gly Gln Gln Gly Pro Tyr Gly
            370                 375                 380

Pro Gly Gly Ser Ala Ala Ala Ala Gly Tyr Gln Gln Gly Pro
385                 390                 395                 400

Gly Gly Gln Gly Pro Tyr Gly Pro Gly Ala Ser Ala Ala Ala Ala
            405                 410                 415

Gly Pro Gly Gly Gln Gly Pro Tyr Gly Pro Gly Ala Ser Ala Ala
            420                 425                 430

Ala Ala Gly Pro Gly Gly Tyr Gly Pro Gly Gln Gly Pro Ser Ala
            435                 440                 445

Ser Ala Ala Ala Ala Gly Gly Tyr Gly Ser Gly Pro Gly Gly Tyr
    450                 455                 460

Gly Pro Tyr Gly Pro Gly Gly Ser Ala Ala Ala Ala Gly Pro Gly
465                 470                 475                 480

Ser Gly Gln Gln Gly Gln Gly Pro Tyr Gly Pro Gly Ala Ser Ala Ala
            485                 490                 495

Ala Ala Ala Gly Gly Tyr Gly Pro Gly Gln Gln Gly Pro Tyr Gly Pro
            500                 505                 510

Gly Gly Ser Ala Ala Ala Ala Gly Pro Gly Ser Gly Gly Tyr Gly
            515                 520                 525

Pro Gly Ala Ser Ala Ala Ala Ala Gly Gly Asn Gly Pro Gly Ser
530                 535                 540

Gly Gly Tyr Gly Pro Gly Gln Gln Gly Pro Gly Ser Ala Ala Ala
545                 550                 555                 560

Ala Ala Gly Gly Tyr Gln Gln Gly Pro Gly Gly Gln Gly Pro Tyr Gly
            565                 570                 575

Pro Gly Ala Ser Ala Ala Ala Ala Gly Pro Gly Ser Gly Gln Gln
            580                 585                 590

Gly Pro Gly Ala Ser
        595

<210> SEQ ID NO 11
<211> LENGTH: 12
<212> TYPE: PRT
<213> ORGANISM: Artificial Sequence
<220> FEATURE:
<223> OTHER INFORMATION: HisTag

<400> SEQUENCE: 11

Met His His His His His His Ser Ser Gly Ser Ser
1               5                   10

<210> SEQ ID NO 12
<211> LENGTH: 608
<212> TYPE: PRT
<213> ORGANISM: Artificial Sequence
<220> FEATURE:
<223> OTHER INFORMATION: PRT380

<400> SEQUENCE: 12

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln

-continued

```
            20                  25                  30
Asn Gly Pro Gly Ser Gly Gln Gln Gly Pro Gly Gln Ser Ala Ala
            35                  40                  45
Ala Ala Gly Gln Tyr Gly Pro Gly Gln Gln Gly Pro Gly Gln Gln
            50                  55                  60
Gly
Pro Gly Ser Ser Ala Ala Ala Ala Gly Pro Gly Gln Tyr Gly Pro
65                  70                  75                  80
Gly Gln Gln Gly Pro Ser Ala Ser Ala Ala Ala Ala Gly Pro Gly
                    85                  90                  95
Ser Gly Gln Gln Gly Pro Gly Ala Ser Ala Ala Ala Ala Gly Gln
                    100                 105                 110
Tyr Gly Pro Gly Gln Gln Gly Pro Gln Gln Gly Pro Gly Ser Ser
                    115                 120                 125
Ala Ala Ala Ala Ala Gly Gln Tyr Gly Ser Gly Pro Gly Gln Gln Gly
                    130                 135                 140
Pro Tyr Gly Ser Ala Ala Ala Ala Gly Pro Gly Ser Gly Gln Tyr
145                 150                 155                 160
Gly Gln Gly Pro Tyr Gly Pro Gly Ala Ser Ala Ala Ala Ala Gly
                    165                 170                 175
Pro Gly Gln Tyr Gly Pro Gly Gln Gln Gly Pro Ser Ala Ser Ala Ala
                    180                 185                 190
Ala Ala Ala Gly Ser Gly Gln Gln Gly Pro Gly Gln Tyr Gly Pro Tyr
                    195                 200                 205
Ala Ser Ala Ala Ala Ala Gly Gln Tyr Gly Ser Gly Pro Gly Gln
210                 215                 220
Gln Gly Pro Tyr Gly Pro Gly Gln Ser Ala Ala Ala Ala Gly Ser
225                 230                 235                 240
Gly Gln Gln Gly Pro Gln Gln Gly Pro Tyr Ala Ser Ala Ala Ala
                    245                 250                 255
Ala Ala Gly Pro Gly Gln Gln Gly Pro Tyr Gly Pro Gly Ser Ser Ala
                    260                 265                 270
Ala Ala Ala Gly Gln Tyr Gly Tyr Gly Pro Gly Gln Gln Gly Pro
                    275                 280                 285
Tyr Gly Pro Gly Ala Ser Ala Ala Ala Ala Gly Gln Asn Gly Pro
                    290                 295                 300
Gly Ser Gly Gln Tyr Gly Pro Gly Gln Gln Gly Pro Gly Gln Ser Ala
305                 310                 315                 320
Ala Ala Ala Gly Pro Gly Gln Gln Gly Pro Tyr Gly Pro Gly Ala
                    325                 330                 335
Ser Ala Ala Ala Ala Gly Gln Tyr Gly Pro Gly Gln Gln Gly Pro
                    340                 345                 350
Gly Gln Tyr Gly Pro Gly Ser Ser Ala Ala Ala Ala Gly Pro Gly
                    355                 360                 365
Gln Gln Gly Pro Tyr Gly Pro Gly Ser Ser Ala Ala Ala Ala Gly
                    370                 375                 380
Gln Tyr Gly Pro Gly Gln Gln Gly Pro Tyr Gly Pro Gly Gln Ser Ala
385                 390                 395                 400
Ala Ala Ala Gly Gln Tyr Gln Gln Gly Pro Gly Gln Gln Gly Pro
                    405                 410                 415
Tyr Gly Pro Gly Ala Ser Ala Ala Ala Ala Gly Pro Gly Gln Gln
                    420                 425                 430
Gly Pro Tyr Gly Pro Gly Ala Ser Ala Ala Ala Ala Gly Pro Gly
                    435                 440                 445
```

```
Gln Tyr Gly Pro Gly Gln Gly Pro Ser Ala Ser Ala Ala Ala
    450                 455                 460

Ala Gly Gln Tyr Gly Ser Gly Pro Gly Gln Tyr Gly Pro Tyr Gly Pro
465                 470                 475                 480

Gly Gln Ser Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gln
            500                 505                 510

Tyr Gly Pro Gly Gln Gln Gly Pro Tyr Gly Pro Gly Gln Ser Ala Ala
            515                 520                 525

Ala Ala Ala Gly Pro Gly Ser Gly Gln Tyr Gly Pro Gly Ala Ser Ala
530                 535                 540

Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Gly Gln Tyr
            565                 570                 575

Gln Gln Gly Pro Gly Gln Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
            595                 600                 605

<210> SEQ ID NO 13
<211> LENGTH: 601
<212> TYPE: PRT
<213> ORGANISM: Artificial Sequence
<220> FEATURE:
<223> OTHER INFORMATION: PRT410

<400> SEQUENCE: 13

Met His His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gln Gly Pro Gly Ser Ser Ala
            50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
            85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gly Pro Ser Ala Ser Ala
            165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205
```

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Gly Pro Gly Gln Gln
    290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
        355                 360                 365

Ser Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
    515                 520                 525

Gly Gln Tyr Gln Gln Gly Pro Gly Gln Gln Gly Pro Tyr Gly Pro Gly
        530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
    595                 600

<210> SEQ ID NO 14
<211> LENGTH: 576

<212> TYPE: PRT
<213> ORGANISM: Artificial Sequence
<220> FEATURE:
<223> OTHER INFORMATION: PRT525

<400> SEQUENCE: 14

Met His His His His His His Ser Ser Gly Ser Gly Pro Gly Gln
1               5                   10                  15

Gln Gly Pro Tyr Gly Pro Gly Ala Ser Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Gly Pro
                85                  90                  95

Gly Ser Gly Gln Gln Gly Pro Gly Ala Ser Gly Gln Tyr Gly Pro Gly
                100                 105                 110

Gln Gln Gly Pro Gly Gln Gln Gly Pro Gly Ser Ser Ala Ala Ala
                115                 120                 125

Ala Ala Ala Gly Ser Tyr Gly Ser Gly Pro Gly Gln Gln Gly Pro Tyr
130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala
                180                 185                 190

Gly Ser Gly Gln Gln Gly Pro Gly Gln Tyr Gly Pro Tyr Ala Ser Ala
                195                 200                 205

Ala Ala Ala Ala Ala Ala Gly Ser Tyr Gly Ser Gly Pro Gly Gln Gln
210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Gly Pro
                245                 250                 255

Gly Gln Gln Gly Pro Tyr Gly Pro Gly Ser Ser Ala Ala Ala Ala
                260                 265                 270

Ala Ala Gly Ser Tyr Gly Tyr Gly Pro Gly Gln Gln Gly Pro Tyr Gly
275                 280                 285

Pro Gly Ala Ser Gly Gln Asn Gly Pro Gly Ser Gly Gln Tyr Gly Pro
        290                 295                 300

Gly Gln Gln Gly Pro Gly Pro Ser Ala Ala Ala Ala Ala Ala Gly
305                 310                 315                 320

Pro Gly Gln Gln Gly Pro Tyr Gly Pro Gly Ala Ser Ala Ala Ala
                325                 330                 335

Ala Ala Ala Gly Ser Tyr Gly Pro Gly Gln Gln Gly Pro Gly Gln Tyr
                340                 345                 350

Gly Pro Gly Ser Ser Gly Pro Gly Gln Gln Gly Pro Tyr Gly Pro Gly
            355                 360                 365

Ser Ser Ala Ala Ala Ala Ala Ala Gly Ser Tyr Gly Pro Gly Gln
            370                 375                 380

```
Gln Gly Pro Tyr Gly Pro Gly Pro Ser Ala Ala Ala Ala Ala
385                 390                 395                 400

Gly Ser Tyr Gln Gln Gly Pro Gly Gln Gln Gly Pro Tyr Gly Pro Gly
                405                 410                 415

Ala Ser Gly Pro Gly Gln Gln Gly Pro Tyr Gly Pro Gly Ala Ser Ala
            420                 425                 430

Ala Ala Ala Ala Ala Gly Pro Gly Gln Tyr Gly Pro Gly Gln Gln
        435                 440                 445

Gly Pro Ser Ala Ser Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
            485                 490                 495

Ala Ala Ala Ala Ala Gly Ser Tyr Gly Pro Gly Gln Gln Gly Pro
        500                 505                 510

Tyr Gly Pro Gly Pro Ser Ala Ala Ala Ala Ala Gly Pro Gly
            515                 520                 525

Ser Gly Gln Tyr Gly Pro Gly Ala Ser Gly Gln Asn Gly Pro Gly Ser
530                 535                 540

Gly Gln Tyr Gly Pro Gly Gln Gly Pro Gly Pro Ser Ala Ala Ala
545                 550                 555                 560

Ala Ala Ala Ala Gly Pro Gly Ser Gly Gln Gly Pro Gly Ala Ser
            565                 570                 575

<210> SEQ ID NO 15
<211> LENGTH: 2375
<212> TYPE: PRT
<213> ORGANISM: Artificial Sequence
<220> FEATURE:
<223> OTHER INFORMATION: PRT799

<400> SEQUENCE: 15

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
                20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
                100                 105                 110

Gln Gly Pro Gly Ser Ser Ala Ala Ala Ala Ala Gly Gln Tyr Gly Ser
            115                 120                 125

Gly Pro Gly Gln Gln Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175
```

```
Ala Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
            245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
            290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
            355                 360                 365

Ser Ala Ala Ala Ala Gly Gln Tyr Gln Gly Pro Gly Gln Gln
370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
            435                 440                 445

Gly Pro Gly Ser Gly Gln Gln Gly Gln Gly Pro Tyr Gly Pro Gly Ala
            450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
            515                 520                 525

Gly Gln Tyr Gln Gln Gly Pro Gly Gln Gly Pro Tyr Gly Pro Gly
            530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser Gly Gln Gln Gly Pro Tyr Gly
```

-continued

```
                595                 600                 605

Pro Gly Ala Ser Ala Ala Ala Ala Gly Gln Asn Gly Pro Gly Ser
    610                 615                 620

Gly Gln Gln Gly Pro Gly Ser Gly Gln Tyr Gly Pro Gly Gln Gln
625                 630                 635                 640

Gly Pro Gly Gln Gln Gly Pro Gly Ser Ser Ala Ala Ala Ala Gly
                645                 650                 655

Pro Gly Gln Tyr Gly Pro Gly Gln Gln Gly Pro Ser Ala Ser Ala
    660                 665                 670

Ala Ala Ala Gly Pro Gly Ser Gly Gln Gln Gly Pro Gly Ala Ser Gly
    675                 680                 685

Gln Tyr Gly Pro Gly Gln Gln Gly Pro Gly Gln Gln Gly Pro Gly Ser
    690                 695                 700

Ser Ala Ala Ala Ala Gly Gln Tyr Gly Ser Gly Pro Gly Gln Gln
705                 710                 715                 720

Gly Pro Tyr Gly Ser Ala Ala Ala Ala Gly Pro Gly Ser Gly Gln
                725                 730                 735

Tyr Gly Gln Gly Pro Tyr Gly Pro Gly Ala Ser Gly Pro Gly Gln Tyr
    740                 745                 750

Gly Pro Gly Gln Gln Gly Pro Ser Ala Ser Ala Ala Ala Ala Gly
    755                 760                 765

Ser Gly Gln Gln Gly Pro Gly Gln Tyr Gly Pro Tyr Ala Ser Ala Ala
770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
                805                 810                 815

Pro Tyr Ala Ser Ala Ala Ala Ala Gly Pro Gly Gln Gln Gly Pro
    820                 825                 830

Tyr Gly Pro Gly Ser Ser Ala Ala Ala Ala Gly Gln Tyr Gly Tyr
    835                 840                 845

Gly Pro Gly Gln Gln Gly Pro Tyr Gly Pro Gly Ala Ser Gly Gln Asn
850                 855                 860

Gly Pro Gly Ser Gly Gln Tyr Gly Pro Gly Gln Gln Gly Pro Gly Gln
865                 870                 875                 880

Ser Ala Ala Ala Ala Gly Pro Gly Gln Gln Gly Pro Tyr Gly Pro
                885                 890                 895

Gly Ala Ser Ala Ala Ala Ala Gly Gln Tyr Gly Pro Gly Gln Gln
    900                 905                 910

Gly Pro Gly Gln Tyr Gly Pro Gly Ser Ser Gly Pro Gly Gln Gln Gly
    915                 920                 925

Pro Tyr Gly Pro Gly Ser Ser Ala Ala Ala Ala Gly Gln Tyr Gly
    930                 935                 940

Pro Gly Gln Gln Gly Pro Tyr Gly Pro Gly Ser Ala Ala Ala Ala
945                 950                 955                 960

Ala Gly Gln Tyr Gln Gln Gly Pro Gly Gln Gly Pro Tyr Gly Pro
                965                 970                 975

Gly Ala Ser Gly Pro Gly Gln Gln Gly Pro Tyr Gly Pro Gly Ala Ser
    980                 985                 990

Ala Ala Ala Ala Ala Gly Pro Gly  Gln Tyr Gly Pro Gly  Gln Gln Gly
    995                 1000                1005

Pro Ser  Ala Ser Ala Ala Ala  Ala Ala Gly Gln Tyr  Gly Ser Gly
    1010                1015                1020
```

```
Pro Gly Gln Tyr Gly Pro Tyr Gly Pro Gly Gln Ser Gly Pro Gly
    1025                1030                1035

Ser Gly Gln Gln Gly Gln Gly Pro Tyr Gly Pro Gly Ala Ser Ala
    1040                1045                1050

Ala Ala Ala Ala Gly Gln Tyr Gly Pro Gly Gln Gln Gly Pro Tyr
    1055                1060                1065

Gly Pro Gly Gln Ser Ala Ala Ala Ala Gly Pro Gly Ser Gly
    1070                1075                1080

Gln Tyr Gly Pro Gly Ala Ser Gly Gln Asn Gly Pro Gly Ser Gly
    1085                1090                1095

Gln Tyr Gly Pro Gly Gln Gln Gly Pro Gly Gln Ser Ala Ala Ala
    1100                1105                1110

Ala Ala Gly Gln Tyr Gln Gln Gly Pro Gly Gln Gln Gly Pro Tyr
    1115                1120                1125

Gly Pro Gly Ala Ser Ala Ala Ala Ala Ala Gly Gln Tyr Gly Ser
    1130                1135                1140

Gly Pro Gly Gln Gln Gly Pro Tyr Gly Pro Gly Gln Ser Gly Ser
    1145                1150                1155

Gly Gln Gln Gly Pro Gly Gln Gly Pro Tyr Ala Ser Ala Ala
    1160                1165                1170

Ala Ala Ala Gly Pro Gly Ser Gly Gln Gln Gly Pro Gly Ala Ser
    1175                1180                1185

Gly Gln Gln Gly Pro Tyr Gly Pro Gly Ala Ser Ala Ala Ala Ala
    1190                1195                1200

Ala Gly Gln Asn Gly Pro Gly Ser Gly Gln Gln Gly Pro Gly Gln
    1205                1210                1215

Ser Gly Gln Tyr Gly Pro Gly Gln Gln Gly Pro Gly Gln Gln Gly
    1220                1225                1230

Pro Gly Ser Ser Ala Ala Ala Ala Ala Gly Pro Gly Gln Tyr Gly
    1235                1240                1245

Pro Gly Gln Gln Gly Pro Ser Ala Ser Ala Ala Ala Ala Ala Gly
    1250                1255                1260

Pro Gly Ser Gly Gln Gln Gly Pro Gly Ala Ser Gly Gln Tyr Gly
    1265                1270                1275

Pro Gly Gln Gln Gly Pro Gly Gln Gln Gly Pro Gly Ser Ser Ala
    1280                1285                1290

Ala Ala Ala Ala Gly Gln Tyr Gly Ser Gly Pro Gly Gln Gln Gly
    1295                1300                1305

Pro Tyr Gly Ser Ala Ala Ala Ala Ala Gly Pro Gly Ser Gly Gln
    1310                1315                1320

Tyr Gly Gln Gly Pro Tyr Gly Pro Gly Ala Ser Gly Pro Gly Gln
    1325                1330                1335

Tyr Gly Pro Gly Gln Gln Gly Pro Ser Ala Ser Ala Ala Ala Ala
    1340                1345                1350

Ala Gly Ser Gly Gln Gln Gly Pro Gly Gln Tyr Gly Pro Tyr Ala
    1355                1360                1365

Ser Ala Ala Ala Ala Ala Gly Gln Tyr Gly Ser Gly Pro Gly Gln
    1370                1375                1380

Gln Gly Pro Tyr Gly Pro Gly Gln Ser Gly Ser Gly Gln Gln Gly
    1385                1390                1395

Pro Gly Gln Gln Gly Pro Tyr Ala Ser Ala Ala Ala Ala Gly
    1400                1405                1410
```

```
Pro Gly Gln Gln Gly Pro Tyr Gly Pro Gly Ser Ser Ala Ala Ala
    1415                1420            1425

Ala Ala Gly Gln Tyr Gly Tyr Gly Pro Gly Gln Gln Gly Pro Tyr
    1430                1435            1440

Gly Pro Gly Ala Ser Gly Gln Asn Gly Pro Gly Ser Gly Gln Tyr
    1445                1450            1455

Gly Pro Gly Gln Gln Gly Pro Gly Gln Ser Ala Ala Ala Ala Ala
    1460                1465            1470

Gly Pro Gly Gln Gln Gly Pro Tyr Gly Pro Gly Ala Ser Ala Ala
    1475                1480            1485

Ala Ala Ala Gly Gln Tyr Gly Pro Gly Gln Gln Gly Pro Gly Gln
    1490                1495            1500

Tyr Gly Pro Gly Ser Ser Gly Pro Gly Gln Gln Gly Pro Tyr Gly
    1505                1510            1515

Pro Gly Ser Ser Ala Ala Ala Ala Gly Gln Tyr Gly Pro Gly
    1520                1525            1530

Gln Gln Gly Pro Tyr Gly Pro Gly Gln Ser Ala Ala Ala Ala Ala
    1535                1540            1545

Gly Gln Tyr Gln Gly Pro Gly Gln Gln Gly Pro Tyr Gly Pro
    1550                1555            1560

Gly Ala Ser Gly Pro Gly Gln Gln Gly Pro Tyr Gly Pro Gly Ala
    1565                1570            1575

Ser Ala Ala Ala Ala Gly Pro Gly Tyr Gly Pro Gly Gln
    1580                1585            1590

Gln Gly Pro Ser Ala Ser Ala Ala Ala Ala Gly Gln Tyr Gly
    1595                1600            1605

Ser Gly Pro Gly Gln Tyr Gly Pro Tyr Gly Pro Gly Gln Ser Gly
    1610                1615            1620

Pro Gly Ser Gly Gln Gln Gly Gln Gly Pro Tyr Gly Pro Gly Ala
    1625                1630            1635

Ser Ala Ala Ala Ala Gly Gln Tyr Gly Pro Gly Gln Gln Gly
    1640                1645            1650

Pro Tyr Gly Pro Gly Gln Ser Ala Ala Ala Ala Gly Pro Gly
    1655                1660            1665

Ser Gly Gln Tyr Gly Pro Gly Ala Ser Gly Gln Asn Gly Pro Gly
    1670                1675            1680

Ser Gly Gln Tyr Gly Pro Gly Gln Gln Gly Pro Gly Gln Ser Ala
    1685                1690            1695

Ala Ala Ala Gly Gln Tyr Gln Gln Gly Pro Gly Gln Gln Gly
    1700                1705            1710

Pro Tyr Gly Pro Gly Ala Ser Ala Ala Ala Ala Gly Gln Tyr
    1715                1720            1725

Gly Ser Gly Pro Gly Gln Gln Gly Pro Tyr Gly Pro Gly Gln Ser
    1730                1735            1740

Gly Ser Gly Gln Gln Gly Pro Gly Gln Gln Gly Pro Tyr Ala Ser
    1745                1750            1755

Ala Ala Ala Ala Gly Pro Gly Ser Gly Gln Gln Gly Pro Gly
    1760                1765            1770

Ala Ser Gly Gln Gln Gly Pro Tyr Gly Pro Gly Ala Ser Ala Ala
    1775                1780            1785

Ala Ala Ala Gly Gln Asn Gly Pro Gly Ser Gly Gln Gln Gly Pro
    1790                1795            1800

Gly Gln Ser Gly Gln Tyr Gly Pro Gly Gln Gln Gly Pro Gly Gln
```

-continued

```
            1805                1810                1815
Gln Gly Pro Gly Ser Ser Ala Ala Ala Ala Gly Pro Gly Gln
        1820                1825                1830
Tyr Gly Pro Gly Gln Gln Gly Pro Ser Ala Ser Ala Ala Ala
        1835                1840                1845
Ala Gly Pro Gly Ser Gly Gln Gln Gly Pro Gly Ala Ser Gly Gln
        1850                1855                1860
Tyr Gly Pro Gly Gln Gln Gly Pro Gly Gln Gln Gly Pro Gly Ser
        1865                1870                1875
Ser Ala Ala Ala Ala Ala Gly Gln Tyr Gly Ser Gly Pro Gly Gln
        1880                1885                1890
Gln Gly Pro Tyr Gly Ser Ala Ala Ala Ala Gly Pro Gly Ser
        1895                1900                1905
Gly Gln Tyr Gly Gln Gly Pro Tyr Gly Pro Gly Ala Ser Gly Pro
        1910                1915                1920
Gly Gln Tyr Gly Pro Gly Gln Gln Gly Pro Ser Ala Ser Ala Ala
        1925                1930                1935
Ala Ala Ala Gly Ser Gly Gln Gln Gly Pro Gly Gln Tyr Gly Pro
        1940                1945                1950
Tyr Ala Ser Ala Ala Ala Ala Gly Gln Tyr Gly Ser Gly Pro
        1955                1960                1965
Gly Gln Gln Gly Pro Tyr Gly Pro Gly Ser Gly Ser Gly Gln
        1970                1975                1980
Gln Gly Pro Gly Gln Gln Gly Pro Tyr Ala Ser Ala Ala Ala Ala
        1985                1990                1995
Ala Gly Pro Gly Gln Gln Gly Pro Tyr Gly Pro Gly Ser Ser Ala
        2000                2005                2010
Ala Ala Ala Ala Gly Gln Tyr Gly Tyr Gly Pro Gly Gln Gln Gly
        2015                2020                2025
Pro Tyr Gly Pro Gly Ala Ser Gly Gln Asn Gly Pro Gly Ser Gly
        2030                2035                2040
Gln Tyr Gly Pro Gly Gln Gln Gly Pro Gly Gln Ser Ala Ala Ala
        2045                2050                2055
Ala Ala Gly Pro Gly Gln Gln Gly Pro Tyr Gly Pro Gly Ala Ser
        2060                2065                2070
Ala Ala Ala Ala Ala Gly Gln Tyr Gly Pro Gly Gln Gln Gly Pro
        2075                2080                2085
Gly Gln Tyr Gly Pro Gly Ser Ser Gly Pro Gly Gln Gln Gly Pro
        2090                2095                2100
Tyr Gly Pro Gly Ser Ser Ala Ala Ala Ala Gly Gln Tyr Gly
        2105                2110                2115
Pro Gly Gln Gln Gly Pro Tyr Gly Pro Gly Gln Ser Ala Ala Ala
        2120                2125                2130
Ala Ala Gly Gln Tyr Gln Gly Pro Gly Gln Gln Gly Pro Tyr
        2135                2140                2145
Gly Pro Gly Ala Ser Gly Pro Gly Gln Gln Gly Pro Tyr Gly Pro
        2150                2155                2160
Gly Ala Ser Ala Ala Ala Ala Gly Pro Gly Gln Tyr Gly Pro
        2165                2170                2175
Gly Gln Gln Gly Pro Ser Ala Ser Ala Ala Ala Ala Gly Gln
        2180                2185                2190
Tyr Gly Ser Gly Pro Gly Gln Tyr Gly Pro Tyr Gly Pro Gly Gln
        2195                2200                2205
```

-continued

Ser Gly Pro Gly Ser Gly Gln Gln Gly Gln Pro Tyr Gly Pro
    2210            2215                2220

Gly Ala Ser Ala Ala Ala Ala Gly Tyr Gly Pro Gly Gln
    2225            2230                2235

Gln Gly Pro Tyr Gly Pro Gly Gln Ser Ala Ala Ala Ala Gly
    2240            2245                2250

Pro Gly Ser Gly Gln Tyr Gly Pro Gly Ala Ser Gly Gln Asn Gly
    2255            2260                2265

Pro Gly Ser Gly Gln Tyr Gly Pro Gly Gln Gln Gly Pro Gly Gln
    2270            2275                2280

Ser Ala Ala Ala Ala Gly Gln Tyr Gln Gly Pro Gly Gln
    2285            2290                2295

Gln Gly Pro Tyr Gly Pro Gly Ala Ser Ala Ala Ala Ala Gly
    2300            2305                2310

Gln Tyr Gly Ser Gly Pro Gly Gln Gln Gly Pro Tyr Gly Pro Gly
    2315            2320                2325

Gln Ser Gly Ser Gly Gln Gln Gly Pro Gly Gln Gln Gly Pro Tyr
    2330            2335                2340

Ala Ser Ala Ala Ala Ala Ala Gly Pro Gly Ser Gly Gln Gln Gly
    2345            2350                2355

Ser Ser Val Asp Lys Leu Ala Ala Ala Leu Glu His His His His
    2360            2365                2370

His His
    2375

<210> SEQ ID NO 16
<211> LENGTH: 608
<212> TYPE: PRT
<213> ORGANISM: Artificial Sequence
<220> FEATURE:
<223> OTHER INFORMATION: PRT313

<400> SEQUENCE: 16

Met His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
                20                  25                  30

Asn Gly Pro Gly Ser Gly Gln Gln Gly Pro Gly Gly Ser Ala Ala
                35                  40                  45

Ala Ala Gly Gly Tyr Gly Pro Gly Gln Pro Gly Gln Gln Gly
        50                  55              60

Pro Gly Ser Ser Ala Ala Ala Ala Gly Pro Gly Gly Tyr Gly Pro
65              70                  75                  80

Gly Gly Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gly
                100                 105                 110

Tyr Gly Pro Gly Gly Gln Gly Pro Gln Gln Gly Pro Gly Ser Ser
                115                 120                 125

Ala Ala Ala Ala Ala Gly Gly Tyr Gly Ser Gly Pro Gly Gln Gln Gly
                130                 135                 140

Pro Tyr Gly Ser Ala Ala Ala Ala Gly Pro Gly Ser Gly Gly Tyr
145             150                 155                 160

Gly Gln Gly Pro Tyr Gly Pro Gly Ala Ser Ala Ala Ala Ala Gly
                165                 170                 175

```
Pro Gly Gly Tyr Gly Pro Gly Gln Gly Pro Ser Ala Ser Ala Ala
            180                 185                 190

Ala Ala Ala Gly Ser Gly Gln Gln Gly Pro Gly Gly Tyr Gly Pro Tyr
        195                 200                 205

Ala Ser Ala Ala Ala Ala Gly Gly Tyr Gly Ser Pro Gly Gln
    210                 215                 220

Gln Gly Pro Tyr Gly Pro Gly Ser Ala Ala Ala Ala Gly Ser
225                 230                 235             240

Gly Gln Gln Gly Pro Gly Gln Gly Pro Tyr Ala Ser Ala Ala Ala
            245                 250                 255

Ala Ala Gly Pro Gly Gly Gln Gly Pro Tyr Gly Pro Gly Ser Ser Ala
        260                 265                 270

Ala Ala Ala Ala Gly Gly Tyr Gly Tyr Gly Pro Gly Gly Gln Gly Pro
        275                 280                 285

Tyr Gly Pro Gly Ala Ser Ala Ala Ala Ala Gly Gly Asn Gly Pro
    290                 295                 300

Gly Ser Gly Gly Tyr Gly Pro Gly Gln Gln Gly Pro Gly Gly Ser Ala
305                 310                 315                 320

Ala Ala Ala Ala Gly Pro Gly Gly Gln Gly Pro Tyr Gly Pro Gly Ala
            325                 330                 335

Ser Ala Ala Ala Ala Gly Gly Tyr Gly Pro Gly Gln Gly Pro
        340                 345                 350

Gly Gly Tyr Gly Pro Gly Ser Ser Ala Ala Ala Ala Gly Pro Gly
            355                 360                 365

Gly Gln Gly Pro Tyr Gly Pro Gly Ser Ser Ala Ala Ala Ala Gly
        370                 375                 380

Gly Tyr Gly Pro Gly Gln Gln Gly Pro Tyr Gly Pro Gly Gly Ser Ala
385                 390                 395                 400

Ala Ala Ala Gly Gly Tyr Gln Gly Pro Gly Gly Gln Gly Pro
            405                 410                 415

Tyr Gly Pro Gly Ala Ser Ala Ala Ala Ala Gly Pro Gly Gly Gln
    420                 425                 430

Gly Pro Tyr Gly Pro Gly Ala Ser Ala Ala Ala Ala Gly Pro Gly
        435                 440                 445

Gly Tyr Gly Pro Gly Gly Gln Gly Pro Ser Ala Ser Ala Ala Ala Ala
        450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gly
        500                 505                 510

Tyr Gly Pro Gly Gln Gln Gly Pro Tyr Gly Pro Gly Gly Ser Ala Ala
    515                 520                 525

Ala Ala Ala Gly Pro Gly Ser Gly Gly Tyr Gly Pro Gly Ala Ser Ala
        530                 535                 540

Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Gly Gly Tyr
            565                 570                 575

Gln Gln Gly Pro Gly Gly Gln Gly Pro Tyr Gly Pro Gly Ala Ser Ala
            580                 585                 590
```

```
Ala Ala Ala Gly Pro Gly Ser Gly Gln Gln Gly Pro Gly Ala Ser
            595                 600                 605

<210> SEQ ID NO 17
<211> LENGTH: 590
<212> TYPE: PRT
<213> ORGANISM: Artificial Sequence
<220> FEATURE:
<223> OTHER INFORMATION: Met-PRT399

<400> SEQUENCE: 17

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Gly Gly Tyr Gly Pro Gly Gln Gly Pro Gly Gln Gln Gly
        35                  40                  45

Pro Gly Ser Ser Ala Ala Ala Ala Gly Pro Gly Gly Tyr Gly Pro
    50                  55                  60

Gly Gly Gln Gly Pro Ser Ala Ser Ala Ala Ala Ala Gly Pro Gly
65                  70                  75                  80

Ser Gly Gln Gln Gly Pro Gly Ala Ser Gly Gly Tyr Gly Pro Gly Gly
                85                  90                  95

Gln Gly Pro Gly Gln Gln Gly Pro Gly Ser Ser Ala Ala Ala Ala
            100                 105                 110

Gly Gly Tyr Gly Ser Gly Pro Gly Gln Gln Gly Pro Tyr Gly Ser Ala
            115                 120                 125

Ala Ala Ala Gly Pro Gly Ser Gly Gly Tyr Gly Gln Gly Pro Tyr
        130                 135                 140

Gly Pro Gly Ala Ser Gly Pro Gly Gly Tyr Gly Pro Gly Gly Gln Gly
145                 150                 155                 160

Pro Ser Ala Ser Ala Ala Ala Ala Gly Ser Gly Gln Gln Gly Pro
                165                 170                 175

Gly Gly Tyr Gly Pro Tyr Ala Ser Ala Ala Ala Ala Gly Gly Tyr
            180                 185                 190

Gly Ser Gly Pro Gly Gln Gln Gly Pro Tyr Gly Pro Gly Gly Ser Gly
            195                 200                 205

Ser Gly Gln Gln Gly Pro Gly Gln Gln Gly Pro Tyr Ala Ser Ala Ala
210                 215                 220

Ala Ala Ala Gly Pro Gly Gly Gln Gly Pro Tyr Gly Pro Gly Ser Ser
225                 230                 235                 240

Ala Ala Ala Ala Gly Gly Tyr Gly Tyr Gly Pro Gly Gly Gln Gly
            245                 250                 255

Pro Tyr Gly Pro Gly Ala Ser Gly Gly Asn Gly Pro Gly Ser Gly Gly
        260                 265                 270

Tyr Gly Pro Gly Gln Gln Gly Pro Gly Gly Ser Ala Ala Ala Ala
            275                 280                 285

Gly Pro Gly Gly Gln Gly Pro Tyr Gly Pro Gly Ala Ser Ala Ala Ala
            290                 295                 300

Ala Ala Gly Gly Tyr Gly Pro Gly Gly Gln Pro Gly Gly Tyr Gly
305                 310                 315                 320

Pro Gly Ser Ser Gly Pro Gly Gly Gln Gly Pro Tyr Gly Pro Gly Ser
                325                 330                 335

Ser Ala Ala Ala Ala Gly Gly Tyr Gly Pro Gly Gln Gln Gly Pro
            340                 345                 350
```

Tyr Gly Pro Gly Gly Ser Ala Ala Ala Gly Tyr Gln Gln
                355                 360                 365

Gly Pro Gly Gly Gln Gly Pro Tyr Gly Pro Gly Ala Ser Gly Pro Gly
                370                 375                 380

Gly Gln Gly Pro Tyr Gly Pro Gly Ala Ser Ala Ala Ala Ala Gly
385                 390                 395                 400

Pro Gly Gly Tyr Gly Pro Gly Gln Gly Pro Ser Ala Ser Ala Ala
                405                 410                 415

Ala Ala Ala Gly Gly Tyr Gly Ser Pro Gly Gly Tyr Gly Pro Tyr
                420                 425                 430

Gly Pro Gly Gly Ser Gly Pro Gly Ser Gly Gln Gln Gly Gln Gly Pro
                435                 440                 445

Tyr Gly Pro Gly Ala Ser Ala Ala Ala Ala Gly Gly Tyr Gly Pro
                450                 455                 460

Gly Gln Gln Gly Pro Tyr Gly Pro Gly Ser Ala Ala Ala Ala
465                 470                 475                 480

Gly Pro Gly Ser Gly Tyr Gly Pro Gly Ala Ser Gly Gly Asn Gly
                485                 490                 495

Pro Gly Ser Gly Gly Tyr Gly Pro Gly Gln Gln Gly Pro Gly Gly Ser
                500                 505                 510

Ala Ala Ala Ala Ala Gly Gly Tyr Gln Gln Gly Pro Gly Gln Gly
                515                 520                 525

Pro Tyr Gly Pro Gly Ala Ser Ala Ala Ala Ala Gly Gly Tyr Gly
                530                 535                 540

Ser Gly Pro Gly Gln Gln Gly Pro Tyr Gly Pro Gly Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
                580                 585                 590

<210> SEQ ID NO 18
<211> LENGTH: 601
<212> TYPE: PRT
<213> ORGANISM: Artificial Sequence
<220> FEATURE:
<223> OTHER INFORMATION: PRT399

<400> SEQUENCE: 18

Met His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
                20                  25                  30

Asn Gly Pro Gly Ser Gly Gln Gln Gly Pro Gly Gly Ser Gly Gly Tyr
                35                  40                  45

Gly Pro Gly Gly Gln Gly Pro Gly Gln Gly Pro Gly Ser Ser Ala
                50                  55                  60

Ala Ala Ala Ala Gly Pro Gly Gly Tyr Gly Pro Gly Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gly Tyr Gly Pro Gly Gly Gln Gly Pro Gly Gln
                100                 105                 110

Gln Gly Pro Gly Ser Ser Ala Ala Ala Ala Gly Gly Tyr Gly Ser
                115                 120                 125

-continued

```
Gly Pro Gly Gln Gln Gly Pro Tyr Gly Ser Ala Ala Ala Ala Gly
    130                 135                 140
Pro Gly Ser Gly Gly Tyr Gly Gln Gly Pro Tyr Gly Pro Gly Ala Ser
145                 150                 155                 160
Gly Pro Gly Gly Tyr Gly Pro Gly Gly Gln Gly Pro Ser Ala Ser Ala
                165                 170                 175
Ala Ala Ala Ala Gly Ser Gly Gln Gln Gly Pro Gly Gly Tyr Gly Pro
            180                 185                 190
Tyr Ala Ser Ala Ala Ala Ala Ala Gly Gly Tyr Gly Ser Gly Pro Gly
        195                 200                 205
Gln Gln Gly Pro Tyr Gly Pro Gly Gly Ser Gly Ser Gly Gln Gln Gly
    210                 215                 220
Pro Gly Gln Gln Gly Pro Tyr Ala Ser Ala Ala Ala Ala Gly Pro
225                 230                 235                 240
Gly Gly Gln Gly Pro Tyr Gly Pro Gly Ser Ser Ala Ala Ala Ala
                245                 250                 255
Gly Gly Tyr Gly Tyr Gly Pro Gly Gly Gln Gly Pro Tyr Gly Pro Gly
            260                 265                 270
Ala Ser Gly Gly Asn Gly Pro Gly Ser Gly Tyr Gly Pro Gly Gln
        275                 280                 285
Gln Gly Pro Gly Gly Ser Ala Ala Ala Ala Gly Pro Gly Gly Gln
    290                 295                 300
Gly Pro Tyr Gly Pro Gly Ala Ser Ala Ala Ala Ala Gly Gly Tyr
305                 310                 315                 320
Gly Pro Gly Gly Gln Gly Pro Gly Gly Tyr Gly Pro Gly Ser Ser Gly
                325                 330                 335
Pro Gly Gly Gln Gly Pro Tyr Gly Pro Gly Ser Ser Ala Ala Ala Ala
            340                 345                 350
Ala Gly Gly Tyr Gly Pro Gly Gln Gln Gly Pro Tyr Gly Pro Gly Gly
        355                 360                 365
Ser Ala Ala Ala Ala Gly Gly Tyr Gln Gln Gly Pro Gly Gly Gln
    370                 375                 380
Gly Pro Tyr Gly Pro Gly Ala Ser Gly Pro Gly Gly Gln Gly Pro Tyr
385                 390                 395                 400
Gly Pro Gly Ala Ser Ala Ala Ala Ala Gly Pro Gly Gly Tyr Gly
                405                 410                 415
Pro Gly Gly Gln Gly Pro Ser Ala Ser Ala Ala Ala Ala Gly Gly
            420                 425                 430
Tyr Gly Ser Gly Pro Gly Gly Tyr Gly Pro Tyr Gly Pro Gly Gly Ser
        435                 440                 445
Gly Pro Gly Ser Gly Gln Gln Gly Gln Gly Pro Tyr Gly Pro Gly Ala
    450                 455                 460
Ser Ala Ala Ala Ala Gly Gly Tyr Gly Pro Gly Gln Gln Gly Pro
465                 470                 475                 480
Tyr Gly Pro Gly Gly Ser Ala Ala Ala Ala Gly Pro Gly Ser Gly
                485                 490                 495
Gly Tyr Gly Pro Gly Ala Ser Gly Gly Asn Gly Pro Gly Ser Gly Gly
            500                 505                 510
Tyr Gly Pro Gly Gln Gln Gly Pro Gly Gly Ser Ala Ala Ala Ala
        515                 520                 525
Gly Gly Tyr Gln Gln Gly Pro Gly Gly Gln Gly Pro Tyr Gly Pro Gly
    530                 535                 540
Ala Ser Ala Ala Ala Ala Ala Gly Gly Tyr Gly Ser Gly Pro Gly Gln
```

-continued

```
              545                 550                 555                 560
Gln Gly Pro Tyr Gly Pro Gly Ser Gly Ser Gly Gln Gln Gly Pro
                    565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
        595                 600

<210> SEQ ID NO 19
<211> LENGTH: 612
<212> TYPE: PRT
<213> ORGANISM: Artificial Sequence
<220> FEATURE:
<223> OTHER INFORMATION: Met-PRT720

<400> SEQUENCE: 19

Met Gly Pro Gly Gln Gln Gly Pro Tyr Gly Pro Gly Ala Ser Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Gly Pro Gly Gln Tyr Val Leu
50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
            85                  90                  95

Gln Tyr Gly Pro Gly Gln Gln Gly Pro Gly Gln Gln Gly Pro Gly Ser
        100                 105                 110

Ser Ala Ala Ala Ala Gly Ser Tyr Gly Ser Val Leu Ile Gly Pro
    115                 120                 125

Gly Gln Gln Val Leu Ile Gly Pro Tyr Gly Ser Ala Ala Ala Ala
        130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gln Gly Pro Ser Ala Ser
            165                 170                 175

Ala Ala Ala Ala Gly Ser Gly Gln Gln Val Leu Ile Gly Pro Gly
        180                 185                 190

Gln Tyr Val Leu Ile Gly Pro Tyr Ala Ser Ala Ala Ala Ala Gly
    195                 200                 205

Gln Tyr Gly Ser Gly Pro Gly Gln Gln Gly Pro Tyr Gly Pro Gly Gln
        210                 215                 220

Ser Gly Ser Gly Gln Gln Gly Pro Gln Gln Gly Pro Tyr Ala Ser
225                 230                 235                 240

Ala Ala Ala Ala Gly Pro Gly Gln Gln Val Leu Ile Gly Pro Tyr
            245                 250                 255

Val Leu Ile Gly Pro Gly Ser Ser Ala Ala Ala Ala Gly Gln Tyr
        260                 265                 270

Gly Tyr Gly Pro Gly Gln Gln Gly Pro Tyr Gly Pro Gly Ala Ser Gly
    275                 280                 285

Gln Asn Gly Pro Gly Ser Gly Gln Tyr Gly Pro Gly Gln Gln Gly Pro
        290                 295                 300

Gly Gln Ser Ala Ala Ala Ala Ala Gly Pro Gly Gln Gln Val Leu Ile
```

```
                305                 310                 315                 320
Gly Pro Tyr Val Leu Ile Gly Pro Gly Ala Ser Ala Ala Ala Ala
                    325                 330                 335
Gly Gln Tyr Gly Pro Gly Gln Gln Gly Pro Gly Gln Tyr Gly Pro Gly
                340                 345                 350
Ser Ser Gly Pro Gly Gln Gly Pro Tyr Gly Pro Gly Ser Ser Ala
                355                 360                 365
Ala Ala Ala Ala Gly Ser Tyr Gly Pro Gly Gln Val Leu Ile Gly
            370                 375                 380
Pro Tyr Val Leu Ile Gly Pro Gly Pro Ser Ala Ala Ala Ala Gly
385                 390                 395                 400
Gln Tyr Gln Gln Gly Pro Gly Gln Gly Pro Tyr Gly Pro Gly Ala
                405                 410                 415
Ser Gly Pro Gly Gln Gln Gly Pro Tyr Gly Pro Gly Ala Ser Ala Ala
            420                 425                 430
Ala Ala Ala Gly Pro Gly Gln Tyr Val Leu Ile Gly Pro Gly Gln Gln
            435                 440                 445
Val Leu Ile Gly Pro Ser Ala Ser Ala Ala Ala Ala Gly Gln Tyr
        450                 455                 460
Gly Ser Gly Pro Gly Gln Tyr Gly Pro Tyr Gly Pro Gly Gln Ser Gly
465                 470                 475                 480
Pro Gly Ser Gly Gln Gln Gly Gln Gly Pro Tyr Gly Pro Gly Ala Ser
                485                 490                 495
Ala Ala Ala Ala Ala Gly Ser Tyr Gly Pro Gly Gln Gln Val Leu Ile
            500                 505                 510
Gly Pro Tyr Val Leu Ile Gly Pro Gly Pro Ser Ala Ala Ala Ala
            515                 520                 525
Gly Pro Gly Ser Gly Gln Tyr Gly Pro Gly Ala Ser Gly Gln Asn Gly
        530                 535                 540
Pro Gly Ser Gly Gln Tyr Gly Pro Gly Gln Gln Gly Pro Gly Gln Ser
545                 550                 555                 560
Ala Ala Ala Ala Ala Gly Gln Tyr Gln Gln Val Leu Ile Gly Pro Gly
                565                 570                 575
Gln Gln Gly Pro Tyr Val Leu Ile Gly Pro Gly Ala Ser Ala Ala Ala
            580                 585                 590
Ala Ala Gly Pro Gly Ser Gly Gln Gln Val Leu Ile Gly Pro Gly Ala
            595                 600                 605
Ser Val Leu Ile
    610

<210> SEQ ID NO 20
<211> LENGTH: 592
<212> TYPE: PRT
<213> ORGANISM: Artificial Sequence
<220> FEATURE:
<223> OTHER INFORMATION: Met-PRT665

<400> SEQUENCE: 20

Met Gly Pro Gly Gln Gln Gly Pro Tyr Gly Pro Gly Ala Ser Ala Ala
1               5                   10                  15
Ala Ala Ala Ala Ala Gly Ser Asn Gly Pro Gly Ser Gly Gln Gln Gly
            20                  25                  30
Pro Gly Gln Ser Gly Gln Tyr Gly Pro Gly Gln Gln Gly Pro Gly Gln
        35                  40                  45
Gln Gly Pro Gly Ser Ser Ala Ala Ala Ala Ala Ala Gly Pro Gly
```

-continued

```
                50                  55                  60
Gln Tyr Val Leu Ile Gly Pro Gly Gln Gln Gly Pro Ser Ala Ser Ala
 65                  70                  75                  80

Ala Ala Ala Ala Ala Ala Gly Pro Gly Ser Gly Gln Gln Gly Pro Gly
                 85                  90                  95

Ala Ser Gly Gln Tyr Gly Pro Gly Gln Gln Gly Pro Gly Gln Gln Gly
                100                 105                 110

Pro Gly Ser Ser Ala Ala Ala Ala Ala Ala Gly Ser Tyr Gly Ser
                115                 120                 125

Val Leu Ile Gly Pro Gly Gln Gln Gly Pro Tyr Gly Ser Ala Ala Ala
        130                 135                 140

Ala Ala Ala Ala Gly Pro Gly Ser Gly Gln Tyr Gly Gln Gly Pro Tyr
145                 150                 155                 160

Gly Pro Gly Ala Ser Gly Pro Gly Gln Tyr Gly Pro Gly Gln Gln Gly
                165                 170                 175

Pro Ser Ala Ser Ala Ala Ala Ala Ala Ala Gly Ser Gly Gln Gln
                180                 185                 190

Val Leu Ile Gly Pro Gly Gln Tyr Gly Pro Tyr Ala Ser Ala Ala Ala
        195                 200                 205

Ala Ala Ala Gly Ser Tyr Gly Ser Gly Pro Gly Gln Gln Gly Pro
        210                 215                 220

Tyr Gly Pro Gly Gln Ser Gly Ser Gly Gln Gln Gly Pro Gly Gln Gln
225                 230                 235                 240

Gly Pro Tyr Ala Ser Ala Ala Ala Ala Ala Ala Gly Pro Gly Gln
                245                 250                 255

Gln Val Leu Ile Gly Pro Tyr Gly Pro Gly Ser Ser Ala Ala Ala Ala
        260                 265                 270

Ala Ala Ala Gly Ser Tyr Gly Tyr Gly Pro Gly Gln Gln Gly Pro Tyr
        275                 280                 285

Gly Pro Gly Ala Ser Gly Gln Asn Gly Pro Gly Ser Gly Gln Tyr Gly
        290                 295                 300

Pro Gly Gln Gln Gly Pro Gly Pro Ser Ala Ala Ala Ala Ala Ala
305                 310                 315                 320

Gly Pro Gly Gln Gln Val Leu Ile Gly Pro Tyr Gly Pro Gly Ala Ser
                325                 330                 335

Ala Ala Ala Ala Ala Ala Gly Ser Tyr Gly Pro Gly Gln Gln Gly
                340                 345                 350

Pro Gly Gln Tyr Gly Pro Gly Ser Ser Gly Pro Gly Gln Gln Gly Pro
                355                 360                 365

Tyr Gly Pro Gly Ser Ser Ala Ala Ala Ala Ala Ala Gly Ser Tyr
        370                 375                 380

Gly Pro Gly Gln Gln Val Leu Ile Gly Pro Tyr Gly Pro Gly Pro Ser
385                 390                 395                 400

Ala Ala Ala Ala Ala Ala Gly Ser Tyr Gln Gln Gly Pro Gly Gln
                405                 410                 415

Gln Gly Pro Tyr Gly Pro Gly Ala Ser Gly Pro Gly Gln Gln Gly Pro
                420                 425                 430

Tyr Gly Pro Gly Ala Ser Ala Ala Ala Ala Ala Ala Gly Pro Gly
        435                 440                 445

Gln Tyr Val Leu Ile Gly Pro Gly Gln Gln Gly Pro Ser Ala Ser Ala
        450                 455                 460

Ala Ala Ala Ala Ala Ala Gly Ser Tyr Gly Ser Gly Pro Gly Gln Tyr
465                 470                 475                 480
```

```
Gly Pro Tyr Gly Pro Gly Gln Ser Gly Pro Gly Ser Gly Gln Gln Gly
                485                 490                 495

Gln Gly Pro Tyr Gly Pro Gly Ala Ser Ala Ala Ala Ala Ala Ala Ala
            500                 505                 510

Gly Ser Tyr Gly Pro Gly Gln Gln Val Leu Ile Gly Pro Tyr Gly Pro
        515                 520                 525

Gly Pro Ser Ala Ala Ala Ala Ala Ala Gly Pro Gly Ser Gly Gln
    530                 535                 540

Tyr Gly Pro Gly Ala Ser Gly Gln Asn Gly Pro Ser Gly Gln Tyr
545                 550                 555                 560

Gly Pro Gly Gln Gln Gly Pro Gly Ser Ala Ala Ala Ala Ala
                565                 570                 575

Ala Gly Pro Gly Ser Gly Gln Gln Gly Pro Gly Ala Ser Val Leu Ile
            580                 585                 590

<210> SEQ ID NO 21
<211> LENGTH: 619
<212> TYPE: PRT
<213> ORGANISM: Artificial Sequence
<220> FEATURE:
<223> OTHER INFORMATION: Met-PRT666

<400> SEQUENCE: 21

Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Gly Pro Gly
    50                  55                  60

Gln Tyr Val Leu Ile Gly Pro Gly Gln Gln Val Leu Ile Gly Pro Ser
65                  70                  75                  80

Ala Ser Ala Ala Ala Ala Ala Ala Gly Pro Gly Ser Gly Gln Gln
            85                  90                  95

Gly Pro Gly Ala Ser Gly Gln Tyr Gly Pro Gly Gln Gln Gly Pro Gly
            100                 105                 110

Gln Gln Gly Pro Gly Ser Ser Ala Ala Ala Ala Ala Ala Gly Ser
        115                 120                 125

Tyr Gly Ser Val Leu Ile Gly Pro Gly Gln Gln Val Leu Ile Gly Pro
    130                 135                 140

Tyr Gly Ser Ala Ala Ala Ala Ala Ala Gly Pro Gly Ser Gly Gln
145                 150                 155                 160

Tyr Gly Gln Gly Pro Tyr Gly Pro Gly Ala Ser Gly Pro Gly Gln Tyr
                165                 170                 175

Gly Pro Gly Gln Gln Gly Pro Ser Ala Ser Ala Ala Ala Ala Ala
            180                 185                 190

Ala Gly Ser Gly Gln Gln Val Leu Ile Gly Pro Gly Gln Tyr Val Leu
        195                 200                 205

Ile Gly Pro Tyr Ala Ser Ala Ala Ala Ala Ala Gly Ser Tyr
    210                 215                 220

Gly Ser Gly Pro Gly Gln Gly Pro Tyr Gly Pro Gly Gln Ser Gly
225                 230                 235                 240

Ser Gly Gln Gln Gly Pro Gly Gln Gln Gly Pro Tyr Ala Ser Ala Ala
                245                 250                 255
```

Ala Ala Ala Ala Gly Pro Gly Gln Gln Val Leu Ile Gly Pro Tyr
            260                 265                 270

Val Leu Ile Gly Pro Gly Ser Ala Ala Ala Ala Ala Ala Ala Gly
        275                 280                 285

Ser Tyr Gly Tyr Gly Pro Gly Gln Gln Gly Pro Tyr Gly Pro Gly Ala
    290                 295                 300

Ser Gly Gln Asn Gly Pro Gly Ser Gly Gln Tyr Gly Pro Gly Gln Gln
305                 310                 315                 320

Gly Pro Gly Pro Ser Ala Ala Ala Ala Ala Ala Gly Pro Gly Gln
                325                 330                 335

Gln Val Leu Ile Gly Pro Tyr Val Leu Ile Gly Pro Gly Ala Ser Ala
        340                 345                 350

Ala Ala Ala Ala Ala Gly Ser Tyr Gly Pro Gly Gln Gln Gly Pro
            355                 360                 365

Gly Gln Tyr Gly Pro Gly Ser Ser Gly Pro Gly Gln Gln Gly Pro Tyr
    370                 375                 380

Gly Pro Gly Ser Ser Ala Ala Ala Ala Ala Ala Gly Ser Tyr Gly
385                 390                 395                 400

Pro Gly Gln Gln Val Leu Ile Gly Pro Tyr Val Leu Ile Gly Pro Gly
                405                 410                 415

Pro Ser Ala Ala Ala Ala Ala Ala Gly Ser Tyr Gln Gln Gly Pro
            420                 425                 430

Gly Gln Gln Gly Pro Tyr Gly Pro Gly Ala Ser Gly Pro Gly Gln Gln
        435                 440                 445

Gly Pro Tyr Gly Pro Gly Ala Ser Ala Ala Ala Ala Ala Ala Gly
    450                 455                 460

Pro Gly Gln Tyr Val Leu Ile Gly Pro Gly Gln Gln Val Leu Ile Gly
465                 470                 475                 480

Pro Ser Ala Ser Ala Ala Ala Ala Ala Gly Ser Tyr Gly Ser
            485                 490                 495

Gly Pro Gly Gln Tyr Gly Pro Tyr Gly Pro Gly Gln Ser Gly Pro Gly
        500                 505                 510

Ser Gly Gln Gln Gly Gln Gly Pro Tyr Gly Pro Gly Ala Ser Ala Ala
    515                 520                 525

Ala Ala Ala Ala Gly Ser Tyr Gly Pro Gly Gln Gln Val Leu Ile
530                 535                 540

Gly Pro Tyr Val Leu Ile Gly Pro Gly Pro Ser Ala Ala Ala Ala
545                 550                 555                 560

Ala Ala Gly Pro Gly Ser Gly Gln Tyr Gly Pro Gly Ala Ser Gly Gln
        565                 570                 575

Asn Gly Pro Gly Ser Gly Gln Tyr Gly Pro Gly Gln Gln Gly Pro Gly
    580                 585                 590

Pro Ser Ala Ala Ala Ala Ala Ala Gly Pro Gly Ser Gly Gln Gln
            595                 600                 605

Val Leu Ile Gly Pro Gly Ala Ser Val Leu Ile
    610                 615

<210> SEQ ID NO 22
<211> LENGTH: 623
<212> TYPE: PRT
<213> ORGANISM: Artificial Sequence
<220> FEATURE:
<223> OTHER INFORMATION: PRT720

<400> SEQUENCE: 22

```
Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
50                  55                  60

Ala Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
            115                 120                 125

Ala Gly Ser Tyr Gly Ser Val Leu Ile Gly Pro Gly Gln Gln Val Leu
        130                 135                 140

Ile Gly Pro Tyr Gly Ser Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
            165                 170                 175

Tyr Gly Pro Gly Gln Gln Gly Pro Ser Ala Ser Ala Ala Ala Ala
            180                 185                 190

Gly Ser Gly Gln Gln Val Leu Ile Gly Pro Gly Gln Tyr Val Leu Ile
        195                 200                 205

Gly Pro Tyr Ala Ser Ala Ala Ala Ala Gly Gln Tyr Gly Ser Gly
        210                 215                 220

Pro Gly Gln Gln Gly Pro Tyr Gly Pro Gly Gln Ser Gly Ser Gly Gln
225                 230                 235                 240

Gln Gly Pro Gly Gln Gln Gly Pro Tyr Ala Ser Ala Ala Ala Ala
            245                 250                 255

Gly Pro Gly Gln Gln Val Leu Ile Gly Pro Tyr Val Leu Ile Gly Pro
        260                 265                 270

Gly Ser Ser Ala Ala Ala Ala Gly Gln Tyr Gly Tyr Gly Pro Gly
        275                 280                 285

Gln Gln Gly Pro Tyr Gly Pro Gly Ala Ser Gly Gln Asn Gly Pro Gly
        290                 295                 300

Ser Gly Gln Tyr Gly Pro Gly Gln Gln Gly Pro Gly Gln Ser Ala Ala
305                 310                 315                 320

Ala Ala Ala Gly Pro Gly Gln Gln Val Leu Ile Gly Pro Tyr Val Leu
            325                 330                 335

Ile Gly Pro Gly Ala Ser Ala Ala Ala Ala Gly Gln Tyr Gly Pro
        340                 345                 350

Gly Gln Gln Gly Pro Gly Gln Tyr Gly Pro Gly Ser Ser Gly Pro Gly
        355                 360                 365

Gln Gln Gly Pro Tyr Gly Pro Gly Ser Ser Ala Ala Ala Ala Gly
        370                 375                 380

Ser Tyr Gly Pro Gly Gln Gln Val Leu Ile Gly Pro Tyr Val Leu Ile
385                 390                 395                 400

Gly Pro Gly Pro Ser Ala Ala Ala Ala Gly Gln Tyr Gln Gln Gly
        405                 410                 415
```

```
Pro Gly Gln Gln Gly Pro Tyr Gly Pro Gly Ala Ser Gly Pro Gly Gln
                420                 425                 430

Gln Gly Pro Tyr Gly Pro Gly Ala Ser Ala Ala Ala Ala Ala Gly Pro
            435                 440                 445

Gly Gln Tyr Val Leu Ile Gly Pro Gly Gln Gln Val Leu Ile Gly Pro
        450                 455                 460

Ser Ala Ser Ala Ala Ala Ala Ala Gly Gln Tyr Gly Ser Gly Pro Gly
465                 470                 475                 480

Gln Tyr Gly Pro Tyr Gly Pro Gly Gln Ser Gly Pro Gly Ser Gly Gln
                485                 490                 495

Gln Gly Gln Gly Pro Tyr Gly Pro Gly Ala Ser Ala Ala Ala Ala Ala
            500                 505                 510

Gly Ser Tyr Gly Pro Gly Gln Gln Val Leu Ile Gly Pro Tyr Val Leu
        515                 520                 525

Ile Gly Pro Gly Pro Ser Ala Ala Ala Ala Gly Pro Gly Ser Gly
        530                 535                 540

Gln Tyr Gly Pro Gly Ala Ser Gly Gln Asn Gly Pro Gly Ser Gly Gln
545                 550                 555                 560

Tyr Gly Pro Gly Gln Gln Gly Pro Gly Gln Ser Ala Ala Ala Ala
                565                 570                 575

Gly Gln Tyr Gln Gln Val Leu Ile Gly Pro Gly Gln Gln Gly Pro Tyr
            580                 585                 590

Val Leu Ile Gly Pro Gly Ala Ser Ala Ala Ala Ala Gly Pro Gly
        595                 600                 605

Ser Gly Gln Gln Val Leu Ile Gly Pro Gly Ala Ser Val Leu Ile
610                 615                 620

<210> SEQ ID NO 23
<211> LENGTH: 603
<212> TYPE: PRT
<213> ORGANISM: Artificial Sequence
<220> FEATURE:
<223> OTHER INFORMATION: PRT665

<400> SEQUENCE: 23

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Val Leu Ile
65                  70                  75                  80

Gly Pro Gly Gln Gln Gly Pro Ser Ala Ser Ala Ala Ala Ala Ala
            85                  90                  95

Ala Gly Pro Gly Ser Gly Gln Gln Gly Pro Gly Ala Ser Gly Gln Tyr
            100                 105                 110

Gly Pro Gly Gln Gln Gly Pro Gly Gln Gln Gly Pro Gly Ser Ser Ala
            115                 120                 125

Ala Ala Ala Ala Ala Gly Ser Tyr Gly Ser Val Leu Ile Gly Pro
        130                 135                 140

Gly Gln Gln Gly Pro Tyr Gly Ser Ala Ala Ala Ala Ala Ala Gly
145                 150                 155                 160
```

```
Pro Gly Ser Gly Gln Tyr Gly Gln Gly Pro Tyr Gly Pro Gly Ala Ser
            165                 170                 175

Gly Pro Gly Gln Tyr Gly Pro Gly Gln Gln Gly Pro Ser Ala Ser Ala
            180                 185                 190

Ala Ala Ala Ala Ala Gly Ser Gly Gln Gln Val Leu Ile Gly Pro
    195                 200                 205

Gly Gln Tyr Gly Pro Tyr Ala Ser Ala Ala Ala Ala Ala Ala Gly
    210                 215                 220

Ser Tyr Gly Ser Gly Pro Gln Gln Gly Pro Tyr Gly Pro Gly Gln
225                 230                 235                 240

Ser Gly Ser Gly Gln Gln Gly Pro Gly Gln Gln Gly Pro Tyr Ala Ser
            245                 250                 255

Ala Ala Ala Ala Ala Ala Gly Pro Gly Gln Gln Val Leu Ile Gly
    260                 265                 270

Pro Tyr Gly Pro Gly Ser Ser Ala Ala Ala Ala Ala Ala Gly Ser
    275                 280                 285

Tyr Gly Tyr Gly Pro Gln Gln Gly Pro Tyr Gly Pro Gly Ala Ser
    290                 295                 300

Gly Gln Asn Gly Pro Gly Ser Gly Gln Tyr Gly Pro Gly Gln Gln Gly
305                 310                 315                 320

Pro Gly Pro Ser Ala Ala Ala Ala Ala Ala Gly Pro Gly Gln Gln
            325                 330                 335

Val Leu Ile Gly Pro Tyr Gly Pro Gly Ala Ser Ala Ala Ala Ala
            340                 345                 350

Ala Ala Gly Ser Tyr Gly Pro Gly Gln Gln Gly Pro Gly Gln Tyr Gly
            355                 360                 365

Pro Gly Ser Ser Gly Pro Gly Gln Gln Gly Pro Tyr Gly Pro Gly Ser
    370                 375                 380

Ser Ala Ala Ala Ala Ala Ala Gly Ser Tyr Gly Pro Gly Gln Gln
385                 390                 395                 400

Val Leu Ile Gly Pro Tyr Gly Pro Gly Pro Ser Ala Ala Ala Ala
            405                 410                 415

Ala Ala Gly Ser Tyr Gln Gln Gly Pro Gly Gln Gln Gly Pro Tyr Gly
            420                 425                 430

Pro Gly Ala Ser Gly Pro Gly Gln Gln Gly Pro Tyr Gly Pro Gly Ala
    435                 440                 445

Ser Ala Ala Ala Ala Ala Ala Gly Pro Gly Gln Tyr Val Leu Ile
450                 455                 460

Gly Pro Gly Gln Gln Gly Pro Ser Ala Ser Ala Ala Ala Ala Ala
465                 470                 475                 480

Ala Gly Ser Tyr Gly Ser Gly Pro Gly Gln Tyr Gly Pro Tyr Gly Pro
            485                 490                 495

Gly Gln Ser Gly Pro Gly Ser Gly Gln Gln Gly Gln Gly Pro Tyr Gly
            500                 505                 510

Pro Gly Ala Ser Ala Ala Ala Ala Ala Ala Gly Ser Tyr Gly Pro
    515                 520                 525

Gly Gln Gln Val Leu Ile Gly Pro Tyr Gly Pro Gly Pro Ser Ala Ala
            530                 535                 540

Ala Ala Ala Ala Gly Pro Gly Ser Gly Tyr Gly Pro Gly Gly Ala
545                 550                 555                 560

Ser Gly Gln Asn Gly Pro Gly Ser Gly Gln Tyr Gly Pro Gly Gln Gln
            565                 570                 575

Gly Pro Gly Pro Ser Ala Ala Ala Ala Ala Ala Ala Gly Pro Gly Ser
```

```
                    580                 585                 590
Gly Gln Gln Gly Pro Gly Ala Ser Val Leu Ile
            595                 600

<210> SEQ ID NO 24
<211> LENGTH: 630
<212> TYPE: PRT
<213> ORGANISM: Artificial Sequence
<220> FEATURE:
<223> OTHER INFORMATION: PRT666

<400> SEQUENCE: 24

Met His His His His His Ser Ser Gly Ser Gly Pro Gly Gln
1               5                   10                  15

Gln Gly Pro Tyr Gly Pro Gly Ala Ser Ala Ala Ala Ala Ala
                20                  25                  30

Gly Ser Asn Gly Pro Gly Ser Gly Gln Gln Gly Pro Gly Gln Ser Gly
            35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Val Leu Ile
65                  70                  75                  80

Gly Pro Gly Gln Gln Val Leu Ile Gly Pro Ser Ala Ser Ala Ala
                85                  90                  95

Ala Ala Ala Ala Gly Pro Gly Ser Gly Gln Gln Gly Pro Gly Ala Ser
            100                 105                 110

Gly Gln Tyr Gly Pro Gly Gln Gln Gly Pro Gly Gln Gln Gly Pro Gly
    115                 120                 125

Ser Ser Ala Ala Ala Ala Ala Ala Gly Ser Tyr Gly Ser Val Leu
130                 135                 140

Ile Gly Pro Gly Gln Gln Val Leu Ile Gly Pro Tyr Gly Ser Ala Ala
145                 150                 155                 160

Ala Ala Ala Ala Ala Gly Pro Gly Ser Gly Gln Tyr Gln Gly Pro
            165                 170                 175

Tyr Gly Pro Gly Ala Ser Gly Pro Gly Gln Tyr Gly Pro Gly Gln Gln
    180                 185                 190

Gly Pro Ser Ala Ser Ala Ala Ala Ala Ala Gly Ser Gly Gln
            195                 200                 205

Gln Val Leu Ile Gly Pro Gly Gln Tyr Val Leu Ile Gly Pro Tyr Ala
    210                 215                 220

Ser Ala Ala Ala Ala Ala Gly Ser Tyr Gly Ser Gly Pro Gly
225                 230                 235                 240

Gln Gln Gly Pro Tyr Gly Pro Gly Gln Ser Gly Ser Gly Gln Gln Gly
            245                 250                 255

Pro Gly Gln Gln Gly Pro Tyr Ala Ser Ala Ala Ala Ala Ala Ala
            260                 265                 270

Gly Pro Gly Gln Gln Val Leu Ile Gly Pro Tyr Val Leu Ile Gly Pro
    275                 280                 285

Gly Ser Ser Ala Ala Ala Ala Ala Ala Gly Ser Tyr Gly Tyr Gly
            290                 295                 300

Pro Gly Gln Gln Gly Pro Tyr Gly Pro Gly Ala Ser Gly Gln Asn Gly
305                 310                 315                 320

Pro Gly Ser Gly Gln Tyr Gly Pro Gly Gln Gln Gly Pro Gly Pro Ser
            325                 330                 335

Ala Ala Ala Ala Ala Ala Ala Gly Pro Gly Gln Gln Val Leu Ile Gly
```

```
                340             345             350
Pro Tyr Val Leu Ile Gly Pro Gly Ala Ser Ala Ala Ala Ala Ala
            355                 360             365

Ala Gly Ser Tyr Gly Pro Gly Gln Gln Gly Pro Gly Gln Tyr Gly Pro
        370                 375             380

Gly Ser Ser Gly Pro Gly Gln Gln Gly Pro Tyr Gly Pro Gly Ser Ser
385                 390                 395                 400

Ala Ala Ala Ala Ala Ala Gly Ser Tyr Gly Pro Gly Gln Gln Val
                405                 410                 415

Leu Ile Gly Pro Tyr Val Leu Ile Gly Pro Gly Ser Ala Ala
            420                 425             430

Ala Ala Ala Ala Gly Ser Tyr Gln Gln Gly Pro Gly Gln Gln Gly Pro
            435                 440             445

Tyr Gly Pro Gly Ala Ser Gly Pro Gly Gln Gln Gly Pro Tyr Gly Pro
            450                 455             460

Gly Ala Ser Ala Ala Ala Ala Ala Ala Gly Pro Gly Gln Tyr Val
465                 470                 475                 480

Leu Ile Gly Pro Gly Gln Gln Val Leu Ile Gly Pro Ser Ala Ser Ala
            485                 490             495

Ala Ala Ala Ala Ala Gly Ser Tyr Gly Ser Gly Pro Gly Gln Tyr
            500                 505             510

Gly Pro Tyr Gly Pro Gly Gln Ser Gly Pro Gly Ser Gly Gln Gln Gly
            515                 520             525

Gln Gly Pro Tyr Gly Pro Gly Ala Ser Ala Ala Ala Ala Ala Ala
            530                 535             540

Gly Ser Tyr Gly Pro Gly Gln Gln Val Leu Ile Gly Pro Tyr Val Leu
545                 550                 555                 560

Ile Gly Pro Gly Pro Ser Ala Ala Ala Ala Ala Gly Pro Gly
            565                 570             575

Ser Gly Gln Tyr Gly Pro Gly Ala Ser Gly Gln Asn Gly Pro Gly Ser
            580                 585             590

Gly Gln Tyr Gly Pro Gly Gln Gln Gly Pro Gly Pro Ser Ala Ala Ala
            595                 600             605

Ala Ala Ala Ala Gly Pro Gly Ser Gly Gln Gln Val Leu Ile Gly Pro
        610                 615             620

Gly Ala Ser Val Leu Ile
625                 630

<210> SEQ ID NO 25
<211> LENGTH: 593
<212> TYPE: PRT
<213> ORGANISM: Artificial Sequence
<220> FEATURE:
<223> OTHER INFORMATION: Met-PRT888

<400> SEQUENCE: 25

Met Gly Ser Ser Gly Pro Gly Val Leu Gly Pro Tyr Gly Pro Gly Ala
1               5                   10                  15

Ser Ala Ala Ala Ala Gly Gln Asn Gly Pro Gly Ser Gly Val Leu
            20                  25                  30

Gly Pro Gly Gln Ser Gly Gln Tyr Gly Pro Gly Val Leu Gly Pro Gly
            35                  40                  45

Val Leu Gly Pro Gly Ser Ala Ala Ala Ala Gly Pro Gly Gln
        50                  55                  60

Tyr Gly Pro Gly Val Leu Gly Pro Ser Ala Ser Ala Ala Ala Ala Ala
```

-continued

```
                65                  70                  75                  80
Gly Pro Gly Ser Gly Val Leu Gly Pro Gly Ala Ser Gly Gln Tyr Gly
                    85                  90                  95
Pro Gly Val Leu Gly Pro Gly Val Leu Gly Pro Gly Ser Ser Ala Ala
                100                 105                 110
Ala Ala Ala Gly Gln Tyr Gly Ser Gly Pro Gly Val Leu Gly Pro Tyr
                115                 120                 125
Gly Ser Ala Ala Ala Ala Gly Pro Gly Ser Gly Gln Tyr Gly Gln
130                 135                 140
Gly Pro Tyr Gly Pro Gly Ala Ser Gly Pro Gln Tyr Gly Pro Gly
145                 150                 155                 160
Val Leu Gly Pro Ser Ala Ser Ala Ala Ala Ala Gly Ser Gly Val
                165                 170                 175
Leu Gly Pro Gly Gln Tyr Gly Pro Tyr Ala Ser Ala Ala Ala Ala
                180                 185                 190
Gly Gln Tyr Gly Ser Gly Pro Gly Val Leu Gly Pro Tyr Gly Pro Gly
                195                 200                 205
Gln Ser Gly Ser Gly Val Leu Gly Pro Gly Val Leu Gly Pro Tyr Ala
                210                 215                 220
Ser Ala Ala Ala Ala Gly Pro Gly Val Leu Gly Pro Tyr Gly Pro
225                 230                 235                 240
Gly Ser Ser Ala Ala Ala Ala Gly Gln Tyr Gly Tyr Gly Pro Gly
                245                 250                 255
Val Leu Gly Pro Tyr Gly Pro Gly Ala Ser Gly Gln Asn Gly Pro Gly
                260                 265                 270
Ser Gly Gln Tyr Gly Pro Gly Val Leu Gly Pro Gly Gln Ser Ala Ala
                275                 280                 285
Ala Ala Ala Gly Pro Gly Val Leu Gly Pro Tyr Gly Pro Gly Ala Ser
                290                 295                 300
Ala Ala Ala Ala Ala Gly Gln Tyr Gly Pro Gly Val Leu Gly Pro Gly
305                 310                 315                 320
Gln Tyr Gly Pro Gly Ser Ser Gly Pro Gly Val Leu Gly Pro Tyr Gly
                325                 330                 335
Pro Gly Ser Ser Ala Ala Ala Ala Gly Gln Tyr Gly Pro Gly Val
                340                 345                 350
Leu Gly Pro Tyr Gly Pro Gly Gln Ser Ala Ala Ala Ala Gly Gln
                355                 360                 365
Tyr Val Leu Gly Pro Gly Val Leu Gly Pro Tyr Gly Pro Gly Ala Ser
                370                 375                 380
Gly Pro Gly Val Leu Gly Pro Tyr Gly Pro Gly Ala Ser Ala Ala Ala
385                 390                 395                 400
Ala Ala Gly Pro Gly Gln Tyr Gly Pro Gly Val Leu Gly Pro Ser Ala
                405                 410                 415
Ser Ala Ala Ala Ala Gly Gln Tyr Gly Ser Gly Pro Gly Gln Tyr
                420                 425                 430
Gly Pro Tyr Gly Pro Gly Gln Ser Gly Pro Gly Ser Gly Val Leu Gly
                435                 440                 445
Gln Gly Pro Tyr Gly Pro Gly Ala Ser Ala Ala Ala Ala Gly Gln
                450                 455                 460
Tyr Gly Pro Gly Val Leu Gly Pro Tyr Gly Pro Gly Gln Ser Ala Ala
465                 470                 475                 480
Ala Ala Ala Gly Pro Gly Ser Gly Gln Tyr Gly Pro Gly Ala Ser Gly
                485                 490                 495
```

Gln Asn Gly Pro Gly Ser Gly Gln Tyr Gly Pro Gly Val Leu Gly Pro
            500                 505                 510

Gly Gln Ser Ala Ala Ala Ala Gly Gln Tyr Val Leu Gly Pro Gly
            515                 520                 525

Val Leu Gly Pro Tyr Gly Pro Gly Ala Ser Ala Ala Ala Ala Gly
530                 535                 540

Gln Tyr Gly Ser Gly Pro Gly Val Leu Gly Pro Tyr Gly Pro Gly Gln
545                 550                 555                 560

Ser Gly Ser Gly Val Leu Gly Pro Val Leu Gly Pro Tyr Ala Ser
            565                 570                 575

Ala Ala Ala Ala Ala Gly Pro Gly Ser Gly Val Leu Gly Pro Gly Ala
            580                 585                 590

Ser

<210> SEQ ID NO 26
<211> LENGTH: 590
<212> TYPE: PRT
<213> ORGANISM: Artificial Sequence
<220> FEATURE:
<223> OTHER INFORMATION: Met-PRT965

<400> SEQUENCE: 26

Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
            20                  25                  30

Ala Ser Gly Ala Tyr Gly Pro Gly Thr Ser Gly Pro Gly Thr Ser Gly
            35                  40                  45

Pro Gly Ser Ser Ala Ala Ala Ala Gly Pro Gly Ala Tyr Gly Pro
50                  55                  60

Gly Thr Ser Gly Pro Ser Ala Ser Ala Ala Ala Ala Gly Pro Gly
65                  70                  75                  80

Ser Gly Thr Ser Gly Pro Gly Ala Ser Gly Ala Tyr Gly Pro Gly Thr
            85                  90                  95

Ser Gly Pro Gly Thr Ser Gly Pro Gly Ser Ser Ala Ala Ala Ala
            100                 105                 110

Gly Ala Tyr Gly Ser Gly Pro Gly Thr Ser Gly Pro Tyr Gly Ser Ala
            115                 120                 125

Ala Ala Ala Gly Pro Gly Ser Gly Ala Tyr Gly Ala Gly Pro Tyr
            130                 135                 140

Gly Pro Gly Ala Ser Gly Pro Gly Ala Tyr Gly Pro Gly Thr Ser Gly
145                 150                 155                 160

Pro Ser Ala Ser Ala Ala Ala Ala Gly Ser Gly Thr Ser Gly Pro
            165                 170                 175

Gly Ala Tyr Gly Pro Tyr Ala Ser Ala Ala Ala Ala Gly Ala Tyr
            180                 185                 190

Gly Ser Gly Pro Gly Thr Ser Gly Pro Tyr Gly Pro Gly Ala Ser Gly
            195                 200                 205

Ser Gly Thr Ser Gly Pro Gly Thr Ser Gly Pro Tyr Ala Ser Ala Ala
            210                 215                 220

Ala Ala Ala Gly Pro Gly Thr Ser Gly Pro Tyr Gly Pro Gly Ser Ser
225                 230                 235                 240

Ala Ala Ala Ala Ala Gly Ala Tyr Gly Tyr Gly Pro Gly Thr Ser Gly
            245                 250                 255

Pro Tyr Gly Pro Gly Ala Ser Gly Ala Asn Gly Pro Gly Ser Gly Ala
            260                 265                 270

Tyr Gly Pro Gly Thr Ser Gly Pro Gly Ala Ser Ala Ala Ala Ala Ala
        275                 280                 285

Gly Pro Gly Thr Ser Gly Pro Tyr Gly Pro Gly Ala Ser Ala Ala Ala
    290                 295                 300

Ala Ala Gly Ala Tyr Gly Pro Gly Thr Ser Gly Pro Gly Ala Tyr Gly
305                 310                 315                 320

Pro Gly Ser Ser Gly Pro Gly Thr Ser Gly Pro Tyr Gly Pro Gly Ser
            325                 330                 335

Ser Ala Ala Ala Ala Gly Ala Tyr Gly Pro Gly Thr Ser Gly Pro
        340                 345                 350

Tyr Gly Pro Gly Ala Ser Ala Ala Ala Ala Gly Ala Tyr Thr Ser
        355                 360                 365

Gly Pro Gly Thr Ser Gly Pro Tyr Gly Pro Gly Ala Ser Gly Pro Gly
    370                 375                 380

Thr Ser Gly Pro Tyr Gly Pro Gly Ala Ser Ala Ala Ala Ala Gly
385                 390                 395                 400

Pro Gly Ala Tyr Gly Pro Gly Thr Ser Gly Pro Ser Ala Ser Ala Ala
            405                 410                 415

Ala Ala Ala Gly Ala Tyr Gly Ser Gly Pro Gly Ala Tyr Gly Pro Tyr
            420                 425                 430

Gly Pro Gly Ala Ser Gly Pro Gly Ser Gly Thr Ser Gly Ala Gly Pro
            435                 440                 445

Tyr Gly Pro Gly Ala Ser Ala Ala Ala Ala Gly Ala Tyr Gly Pro
        450                 455                 460

Gly Thr Ser Gly Pro Tyr Gly Pro Gly Ala Ser Ala Ala Ala Ala
465                 470                 475                 480

Gly Pro Gly Ser Gly Ala Tyr Gly Pro Gly Ala Ser Gly Ala Asn Gly
            485                 490                 495

Pro Gly Ser Gly Ala Tyr Gly Pro Gly Thr Ser Gly Pro Gly Ala Ser
            500                 505                 510

Ala Ala Ala Ala Ala Gly Ala Tyr Thr Ser Gly Pro Gly Thr Ser Gly
            515                 520                 525

Pro Tyr Gly Pro Gly Ala Ser Ala Ala Ala Ala Gly Ala Tyr Gly
        530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala Ala
            565                 570                 575

Ala Ala Gly Pro Gly Ser Gly Thr Ser Gly Pro Gly Ala Ser
            580                 585                 590

<210> SEQ ID NO 27
<211> LENGTH: 593
<212> TYPE: PRT
<213> ORGANISM: Artificial Sequence
<220> FEATURE:
<223> OTHER INFORMATION: Met-PRT889

<400> SEQUENCE: 27

Met Gly Ser Ser Gly Pro Gly Val Leu Gly Pro Tyr Gly Pro Gly Ala
1               5                   10                  15

Ser Ala Ala Ala Ala Gly Ile Asn Gly Pro Gly Ser Gly Val Leu
            20                  25                  30

Gly Pro Gly Ile Ser Gly Ile Tyr Gly Pro Gly Val Leu Gly Pro Gly
            35                  40                  45

Val Leu Gly Pro Gly Ser Ser Ala Ala Ala Ala Gly Pro Gly Ile
 50                  55                  60

Tyr Gly Pro Gly Val Leu Gly Pro Ser Ala Ser Ala Ala Ala Ala
 65                  70                  75                  80

Gly Pro Gly Ser Gly Val Leu Gly Pro Gly Ala Ser Gly Ile Tyr Gly
                85                  90                  95

Pro Gly Val Leu Gly Pro Gly Val Leu Gly Pro Gly Ser Ser Ala Ala
            100                 105                 110

Ala Ala Ala Gly Ile Tyr Gly Ser Gly Pro Gly Val Leu Gly Pro Tyr
            115                 120                 125

Gly Ser Ala Ala Ala Ala Gly Pro Gly Ser Gly Ile Tyr Gly Ile
 130                 135                 140

Gly Pro Tyr Gly Pro Gly Ala Ser Gly Pro Gly Ile Tyr Gly Pro Gly
 145                 150                 155                 160

Val Leu Gly Pro Ser Ala Ser Ala Ala Ala Ala Gly Ser Gly Val
            165                 170                 175

Leu Gly Pro Gly Ile Tyr Gly Pro Tyr Ala Ser Ala Ala Ala Ala
            180                 185                 190

Gly Ile Tyr Gly Ser Gly Pro Gly Val Leu Gly Pro Tyr Gly Pro Gly
            195                 200                 205

Ile Ser Gly Ser Gly Val Leu Gly Pro Gly Val Leu Gly Pro Tyr Ala
 210                 215                 220

Ser Ala Ala Ala Ala Gly Pro Gly Val Leu Gly Pro Tyr Gly Pro
 225                 230                 235                 240

Gly Ser Ser Ala Ala Ala Ala Gly Ile Tyr Gly Tyr Gly Pro Gly
            245                 250                 255

Val Leu Gly Pro Tyr Gly Pro Gly Ala Ser Gly Ile Asn Gly Pro Gly
            260                 265                 270

Ser Gly Ile Tyr Gly Pro Gly Val Leu Gly Pro Gly Ile Ser Ala Ala
            275                 280                 285

Ala Ala Ala Gly Pro Gly Val Leu Gly Pro Tyr Gly Pro Gly Ala Ser
 290                 295                 300

Ala Ala Ala Ala Ala Gly Ile Tyr Gly Pro Gly Val Leu Gly Pro Gly
 305                 310                 315                 320

Ile Tyr Gly Pro Gly Ser Ser Gly Pro Gly Val Leu Gly Pro Tyr Gly
                325                 330                 335

Pro Gly Ser Ser Ala Ala Ala Ala Gly Ile Tyr Gly Pro Gly Val
            340                 345                 350

Leu Gly Pro Tyr Gly Pro Gly Ile Ser Ala Ala Ala Ala Gly Ile
            355                 360                 365

Tyr Val Leu Gly Pro Gly Val Leu Gly Pro Tyr Gly Pro Gly Ala Ser
 370                 375                 380

Gly Pro Gly Val Leu Gly Pro Tyr Gly Pro Gly Ala Ser Ala Ala Ala
 385                 390                 395                 400

Ala Ala Gly Pro Gly Ile Tyr Gly Pro Gly Val Leu Gly Pro Ser Ala
            405                 410                 415

Ser Ala Ala Ala Ala Gly Ile Tyr Gly Ser Gly Pro Gly Ile Tyr
            420                 425                 430

Gly Pro Tyr Gly Pro Gly Ile Ser Gly Pro Gly Ser Gly Val Leu Gly
            435                 440                 445

Ile Gly Pro Tyr Gly Pro Gly Ala Ser Ala Ala Ala Ala Ala Gly Ile

```
                450             455             460
Tyr Gly Pro Gly Val Leu Gly Pro Tyr Gly Pro Gly Ile Ser Ala Ala
465                     470                 475                 480

Ala Ala Ala Gly Pro Gly Ser Gly Ile Tyr Gly Pro Gly Ala Ser Gly
                485                 490                 495

Ile Asn Gly Pro Gly Ser Gly Ile Tyr Gly Pro Gly Val Leu Gly Pro
            500                 505                 510

Gly Ile Ser Ala Ala Ala Ala Gly Ile Tyr Val Leu Gly Pro Gly
        515                 520                 525

Val Leu Gly Pro Tyr Gly Pro Gly Ala Ser Ala Ala Ala Ala Gly
        530                 535                 540

Ile Tyr Gly Ser Gly Pro Gly Val Leu Gly Pro Tyr Gly Pro Gly Ile
545                 550                 555                 560

Ser Gly Ser Gly Val Leu Gly Pro Gly Val Leu Gly Pro Tyr Ala Ser
                565                 570                 575

Ala Ala Ala Ala Ala Gly Pro Gly Ser Gly Val Leu Gly Pro Gly Ala
                580                 585                 590

Ser
```

<210> SEQ ID NO 28
<211> LENGTH: 590
<212> TYPE: PRT
<213> ORGANISM: Artificial Sequence
<220> FEATURE:
<223> OTHER INFORMATION: Met-PRT916

<400> SEQUENCE: 28

```
Met Gly Pro Gly Val Ile Gly Pro Tyr Gly Pro Gly Ala Ser Ala Ala
1               5                   10                  15

Ala Ala Ala Gly Leu Asn Gly Pro Gly Ser Gly Val Ile Gly Pro Gly
                20                  25                  30

Leu Ser Gly Leu Tyr Gly Pro Gly Val Ile Gly Pro Gly Val Ile Gly
            35                  40                  45

Pro Gly Ser Ser Ala Ala Ala Ala Gly Pro Gly Leu Tyr Gly Pro
    50                  55                  60

Gly Val Ile Gly Pro Ser Ala Ser Ala Ala Ala Ala Gly Pro Gly
65                  70                  75                  80

Ser Gly Val Ile Gly Pro Gly Ala Ser Gly Leu Tyr Gly Pro Gly Val
                85                  90                  95

Ile Gly Pro Gly Val Ile Gly Pro Gly Ser Ser Ala Ala Ala Ala Ala
            100                 105                 110

Gly Leu Tyr Gly Ser Gly Pro Gly Val Ile Gly Pro Tyr Gly Ser Ala
        115                 120                 125

Ala Ala Ala Gly Pro Gly Ser Gly Leu Tyr Gly Leu Gly Pro Tyr
    130                 135                 140

Gly Pro Gly Ala Ser Gly Pro Gly Leu Tyr Gly Pro Gly Val Ile Gly
145                 150                 155                 160

Pro Ser Ala Ser Ala Ala Ala Ala Gly Ser Gly Val Ile Gly Pro
        165                 170                 175

Gly Leu Tyr Gly Pro Tyr Ala Ser Ala Ala Ala Ala Gly Leu Tyr
    180                 185                 190

Gly Ser Gly Pro Gly Val Ile Gly Pro Tyr Gly Pro Gly Leu Ser Gly
        195                 200                 205

Ser Gly Val Ile Gly Pro Gly Val Ile Gly Pro Tyr Ala Ser Ala Ala
        210                 215                 220
```

-continued

Ala Ala Ala Gly Pro Gly Val Ile Gly Pro Tyr Gly Pro Gly Ser Ser
225                 230                 235                 240

Ala Ala Ala Ala Gly Leu Tyr Gly Tyr Gly Pro Gly Val Ile Gly
            245                 250                 255

Pro Tyr Gly Pro Gly Ala Ser Gly Leu Asn Gly Pro Gly Ser Gly Leu
                260                 265                 270

Tyr Gly Pro Gly Val Ile Gly Pro Gly Leu Ser Ala Ala Ala Ala
            275                 280                 285

Gly Pro Gly Val Ile Gly Pro Tyr Gly Pro Gly Ala Ser Ala Ala Ala
            290                 295                 300

Ala Ala Gly Leu Tyr Gly Pro Gly Val Ile Gly Pro Gly Leu Tyr Gly
305                 310                 315                 320

Pro Gly Ser Ser Gly Pro Gly Val Ile Gly Pro Tyr Gly Pro Gly Ser
                325                 330                 335

Ser Ala Ala Ala Ala Ala Gly Leu Tyr Gly Pro Gly Val Ile Gly Pro
                340                 345                 350

Tyr Gly Pro Gly Leu Ser Ala Ala Ala Ala Gly Leu Tyr Val Ile
            355                 360                 365

Gly Pro Gly Val Ile Gly Pro Tyr Gly Pro Gly Ala Ser Gly Pro Gly
            370                 375                 380

Val Ile Gly Pro Tyr Gly Pro Gly Ala Ser Ala Ala Ala Ala Gly
385                 390                 395                 400

Pro Gly Leu Tyr Gly Pro Gly Val Ile Gly Pro Ser Ala Ser Ala Ala
                405                 410                 415

Ala Ala Ala Gly Leu Tyr Gly Ser Gly Pro Gly Leu Tyr Gly Pro Tyr
            420                 425                 430

Gly Pro Gly Leu Ser Gly Pro Gly Ser Gly Val Ile Gly Leu Gly Pro
            435                 440                 445

Tyr Gly Pro Gly Ala Ser Ala Ala Ala Ala Gly Leu Tyr Gly Pro
            450                 455                 460

Gly Val Ile Gly Pro Tyr Gly Pro Gly Leu Ser Ala Ala Ala Ala
465                 470                 475                 480

Gly Pro Gly Ser Gly Leu Tyr Gly Pro Gly Ala Ser Gly Leu Asn Gly
                485                 490                 495

Pro Gly Ser Gly Leu Tyr Gly Pro Gly Val Ile Gly Pro Gly Leu Ser
                500                 505                 510

Ala Ala Ala Ala Ala Gly Leu Tyr Val Ile Gly Pro Gly Val Ile Gly
            515                 520                 525

Pro Tyr Gly Pro Gly Ala Ser Ala Ala Ala Ala Gly Leu Tyr Gly
            530                 535                 540

Ser Gly Pro Gly Val Ile Gly Pro Tyr Gly Pro Gly Leu Ser Gly Ser
545                 550                 555                 560

Gly Val Ile Gly Pro Gly Val Ile Gly Pro Tyr Ala Ser Ala Ala Ala
                565                 570                 575

Ala Ala Gly Pro Gly Ser Gly Val Ile Gly Pro Gly Ala Ser
            580                 585                 590

<210> SEQ ID NO 29
<211> LENGTH: 590
<212> TYPE: PRT
<213> ORGANISM: Artificial Sequence
<220> FEATURE:
<223> OTHER INFORMATION: Met-PRT918

<400> SEQUENCE: 29

```
Met Gly Pro Gly Val Phe Pro Tyr Gly Pro Ala Ser Ala Ala
1               5                   10                  15

Ala Ala Ala Gly Ile Asn Gly Pro Ser Gly Val Phe Gly Pro Gly
                20              25              30

Ile Ser Gly Ile Tyr Gly Pro Gly Val Phe Gly Pro Val Phe Gly
            35              40              45

Pro Gly Ser Ser Ala Ala Ala Ala Gly Pro Gly Ile Tyr Gly Pro
        50              55              60

Gly Val Phe Gly Pro Ser Ala Ser Ala Ala Ala Gly Pro Gly
65              70              75              80

Ser Gly Val Phe Gly Pro Gly Ala Ser Gly Ile Tyr Gly Pro Gly Val
                85              90              95

Phe Gly Pro Gly Val Phe Gly Pro Gly Ser Ser Ala Ala Ala Ala
            100             105             110

Gly Ile Tyr Gly Ser Gly Pro Gly Val Phe Gly Pro Tyr Gly Ser Ala
            115             120             125

Ala Ala Ala Ala Gly Pro Gly Ser Gly Ile Tyr Gly Ile Gly Pro Tyr
        130             135             140

Gly Pro Gly Ala Ser Gly Pro Gly Ile Tyr Gly Pro Gly Val Phe Gly
145             150             155             160

Pro Ser Ala Ser Ala Ala Ala Ala Gly Ser Gly Val Phe Gly Pro
            165             170             175

Gly Ile Tyr Gly Pro Tyr Ala Ser Ala Ala Ala Ala Gly Ile Tyr
            180             185             190

Gly Ser Gly Pro Gly Val Phe Gly Pro Tyr Gly Pro Gly Ile Ser Gly
            195             200             205

Ser Gly Val Phe Gly Pro Gly Val Phe Gly Pro Tyr Ala Ser Ala Ala
            210             215             220

Ala Ala Ala Gly Pro Gly Val Phe Gly Pro Tyr Gly Pro Gly Ser Ser
225             230             235             240

Ala Ala Ala Ala Ala Gly Ile Tyr Gly Tyr Gly Pro Gly Val Phe Gly
                245             250             255

Pro Tyr Gly Pro Gly Ala Ser Gly Ile Asn Gly Pro Gly Ser Gly Ile
            260             265             270

Tyr Gly Pro Gly Val Phe Gly Pro Gly Ile Ser Ala Ala Ala Ala
    275             280             285

Gly Pro Gly Val Phe Gly Pro Tyr Gly Pro Gly Ala Ser Ala Ala Ala
    290             295             300

Ala Ala Gly Ile Tyr Gly Pro Gly Val Phe Gly Pro Gly Ile Tyr Gly
305             310             315             320

Pro Gly Ser Ser Gly Pro Gly Val Phe Gly Pro Tyr Gly Pro Gly Ser
            325             330             335

Ser Ala Ala Ala Ala Gly Ile Tyr Gly Pro Gly Val Phe Gly Pro
            340             345             350

Tyr Gly Pro Gly Ile Ser Ala Ala Ala Ala Gly Ile Tyr Val Phe
        355             360             365

Gly Pro Gly Val Phe Gly Pro Tyr Gly Pro Gly Ala Ser Gly Pro Gly
            370             375             380

Val Phe Gly Pro Tyr Gly Pro Gly Ala Ser Ala Ala Ala Ala Gly
385             390             395             400

Pro Gly Ile Tyr Gly Pro Gly Val Phe Gly Pro Ser Ala Ser Ala Ala
            405             410             415
```

```
Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
        435                 440                 445

Tyr Gly Pro Gly Ala Ser Ala Ala Ala Ala Gly Ile Tyr Gly Pro
450                 455                 460

Gly Val Phe Gly Pro Tyr Gly Pro Gly Ile Ser Ala Ala Ala Ala
465             470              475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
                515                 520                 525

Pro Tyr Gly Pro Gly Ala Ser Ala Ala Ala Ala Gly Ile Tyr Gly
        530                 535                 540

Ser Gly Pro Gly Val Phe Gly Pro Tyr Gly Pro Gly Ile Ser Gly Ser
545             550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser
            580                 585                 590

<210> SEQ ID NO 30
<211> LENGTH: 565
<212> TYPE: PRT
<213> ORGANISM: Artificial Sequence
<220> FEATURE:
<223> OTHER INFORMATION: Met-PRT699

<400> SEQUENCE: 30

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
                20                  25                  30

Pro Gly Gln Ser Gly Gln Tyr Gly Pro Gly Val Leu Gly Pro Gly Val
            35                  40                  45

Leu Gly Pro Gly Ser Ser Ala Ala Ala Ala Ala Ala Gly Pro Gly
    50                  55                  60

Gln Tyr Gly Pro Gly Val Leu Gly Pro Ser Ala Ser Ala Ala Ala
65              70                  75                  80

Ala Ala Ala Gly Pro Gly Ser Gly Val Leu Gly Pro Gly Ala Ser Gly
                85                  90                  95

Gln Tyr Gly Pro Gly Val Leu Gly Pro Gly Val Leu Gly Pro Gly Ser
            100                 105                 110

Ser Ala Ala Ala Ala Ala Ala Gly Ser Tyr Gly Ser Gly Pro Gly
    115                 120                 125

Val Leu Gly Pro Tyr Gly Ser Ala Ala Ala Ala Ala Ala Gly Pro
        130                 135                 140

Gly Ser Gly Gln Tyr Gly Gln Gly Pro Tyr Gly Pro Gly Ala Ser Gly
145             150                 155                 160

Pro Gly Gln Tyr Gly Pro Gly Val Leu Gly Pro Ser Ala Ser Ala Ala
                165                 170                 175

Ala Ala Ala Ala Gly Ser Gly Val Leu Gly Pro Gly Gln Tyr Gly
            180                 185                 190
```

```
Pro Tyr Ala Ser Ala Ala Ala Ala Ala Gly Ser Tyr Gly Ser
        195                 200                 205

Gly Pro Gly Val Leu Gly Pro Tyr Gly Pro Gln Ser Gly Ser Gly
210                 215                 220

Val Leu Gly Pro Gly Val Leu Gly Pro Tyr Ala Ser Ala Ala Ala
225                 230                 235                 240

Ala Ala Ala Gly Pro Gly Val Leu Gly Pro Tyr Gly Pro Gly Ser Ser
                245                 250                 255

Ala Ala Ala Ala Ala Ala Gly Ser Tyr Gly Tyr Gly Pro Gly Val
        260                 265                 270

Leu Gly Pro Tyr Gly Pro Gly Ala Ser Gly Gln Asn Gly Pro Gly Ser
        275                 280                 285

Gly Gln Tyr Gly Pro Gly Val Leu Gly Pro Pro Ser Ala Ala Ala
    290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Gly Ser Tyr Gly Pro Gly Val Leu
                325                 330                 335

Gly Pro Gly Gln Tyr Gly Pro Gly Ser Ser Gly Pro Gly Val Leu Gly
                340                 345                 350

Pro Tyr Gly Pro Gly Ser Ser Ala Ala Ala Ala Ala Ala Gly Ser
        355                 360                 365

Tyr Gly Pro Gly Val Leu Gly Pro Tyr Gly Pro Gly Pro Ser Ala Ala
    370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
                405                 410                 415

Pro Gly Ala Ser Ala Ala Ala Ala Ala Ala Gly Pro Gly Gln Tyr
                420                 425                 430

Gly Pro Gly Val Leu Gly Pro Ser Ala Ser Ala Ala Ala Ala Ala
        435                 440                 445

Ala Gly Ser Tyr Gly Ser Gly Pro Gly Gln Tyr Gly Pro Tyr Gly Pro
450                 455                 460

Gly Gln Ser Gly Pro Gly Ser Gly Val Leu Gly Gln Gly Pro Tyr Gly
465                 470                 475                 480

Pro Gly Ala Ser Ala Ala Ala Ala Ala Gly Ser Tyr Gly Pro
                485                 490                 495

Gly Val Leu Gly Pro Tyr Gly Pro Gly Pro Ser Ala Ala Ala Ala
        500                 505                 510

Ala Ala Gly Pro Gly Ser Gly Gln Tyr Gly Pro Gly Ala Ser Gly Gln
    515                 520                 525

Asn Gly Pro Gly Ser Gly Gln Tyr Gly Pro Gly Val Leu Gly Pro Gly
    530                 535                 540

Pro Ser Ala Ala Ala Ala Ala Ala Gly Pro Gly Ser Gly Val Leu
545                 550                 555                 560

Gly Pro Gly Ala Ser
                565

<210> SEQ ID NO 31
<211> LENGTH: 565
<212> TYPE: PRT
<213> ORGANISM: Artificial Sequence
<220> FEATURE:
<223> OTHER INFORMATION: Met-PRT698
```

<400> SEQUENCE: 31

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Ile Ser Gly Ile Tyr Gly Pro Gly Val Leu Gly Pro Gly Val
        35                  40                  45

Leu Gly Pro Gly Ser Ser Ala Ala Ala Ala Ala Gly Pro Gly
    50                  55                  60

Ile Tyr Gly Pro Gly Val Leu Gly Pro Ser Ala Ser Ala Ala Ala
65              70                  75                  80

Ala Ala Ala Gly Pro Gly Ser Gly Val Leu Gly Pro Gly Ala Ser Gly
            85                  90                  95

Ile Tyr Gly Pro Gly Val Leu Gly Pro Gly Val Leu Gly Pro Gly Ser
            100                 105                 110

Ser Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Gly Pro
130                 135                 140

Gly Ser Gly Ile Tyr Gly Ile Gly Pro Tyr Gly Pro Gly Ala Ser Gly
145                 150                 155                 160

Pro Gly Ile Tyr Gly Pro Gly Val Leu Gly Pro Ser Ala Ser Ala Ala
            165                 170                 175

Ala Ala Ala Ala Ala Gly Ser Gly Val Leu Gly Pro Gly Ile Tyr Gly
            180                 185                 190

Pro Tyr Ala Ser Ala Ala Ala Ala Ala Gly Ser Tyr Gly Ser
        195                 200                 205

Gly Pro Gly Val Leu Gly Pro Tyr Gly Pro Gly Ile Ser Gly Ser Gly
    210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
            245                 250                 255

Ala Ala Ala Ala Ala Ala Gly Ser Tyr Gly Tyr Gly Pro Gly Val
        260                 265                 270

Leu Gly Pro Tyr Gly Pro Gly Ala Ser Gly Ile Asn Gly Pro Gly Ser
    275                 280                 285

Gly Ile Tyr Gly Pro Gly Val Leu Gly Pro Gly Ser Ala Ala Ala
    290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Gly Ser Tyr Gly Pro Gly Val Leu
        325                 330                 335

Gly Pro Gly Ile Tyr Gly Pro Gly Ser Ser Gly Pro Gly Val Leu Gly
            340                 345                 350

Pro Tyr Gly Pro Gly Ser Ser Ala Ala Ala Ala Ala Ala Gly Ser
        355                 360                 365

Tyr Gly Pro Gly Val Leu Gly Pro Tyr Gly Pro Gly Ser Ala Ala
        370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly

-continued

```
                405                 410                 415

Pro Gly Ala Ser Ala Ala Ala Ala Ala Ala Ala Gly Pro Gly Ile Tyr
            420                 425                 430

Gly Pro Gly Val Leu Gly Pro Ser Ala Ser Ala Ala Ala Ala Ala Ala
        435                 440                 445

Ala Gly Ser Tyr Gly Ser Gly Pro Gly Ile Tyr Gly Pro Tyr Gly Pro
    450                 455                 460

Gly Ile Ser Gly Pro Gly Ser Gly Val Leu Gly Ile Gly Pro Tyr Gly
465                 470                 475                 480

Pro Gly Ala Ser Ala Ala Ala Ala Ala Ala Ala Gly Ser Tyr Gly Pro
                485                 490                 495

Gly Val Leu Gly Pro Tyr Gly Pro Gly Pro Ser Ala Ala Ala Ala Ala
            500                 505                 510

Ala Ala Gly Pro Gly Ser Gly Ile Tyr Gly Pro Gly Ala Ser Gly Ile
        515                 520                 525

Asn Gly Pro Gly Ser Gly Ile Tyr Gly Pro Gly Val Leu Gly Pro Gly
    530                 535                 540

Pro Ser Ala Ala Ala Ala Ala Ala Ala Gly Pro Gly Ser Gly Val Leu
545                 550                 555                 560

Gly Pro Gly Ala Ser
                565

<210> SEQ ID NO 32
<211> LENGTH: 1179
<212> TYPE: PRT
<213> ORGANISM: Artificial Sequence
<220> FEATURE:
<223> OTHER INFORMATION: Met-PRT966

<400> SEQUENCE: 32

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
            20                  25                  30

Ile Ser Gly Ile Tyr Gly Pro Gly Val Phe Gly Pro Gly Val Phe Gly
        35                  40                  45

Pro Gly Ser Ser Ala Ala Ala Ala Ala Gly Pro Gly Ile Tyr Gly Pro
    50                  55                  60

Gly Val Phe Gly Pro Ser Ala Ser Ala Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
            100                 105                 110

Gly Ile Tyr Gly Ser Gly Pro Gly Val Phe Gly Pro Tyr Gly Ser Ala
        115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Ala Gly Ser Gly Val Phe Gly Pro
                165                 170                 175

Gly Ile Tyr Gly Pro Tyr Ala Ser Ala Ala Ala Ala Ala Gly Ile Tyr
            180                 185                 190

Gly Ser Gly Pro Gly Val Phe Gly Pro Tyr Gly Pro Gly Ile Ser Gly
```

```
            195                 200                 205
Ser Gly Val Phe Gly Pro Gly Val Phe Gly Pro Tyr Ala Ser Ala Ala
210                 215                 220

Ala Ala Ala Gly Pro Gly Val Phe Gly Pro Tyr Gly Pro Gly Ser Ser
225                 230                 235                 240

Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala
            275                 280                 285

Gly Pro Gly Val Phe Gly Pro Tyr Gly Pro Gly Ala Ser Ala Ala Ala
            290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
            325                 330                 335

Ser Ala Ala Ala Ala Gly Ile Tyr Gly Pro Gly Val Phe Gly Pro
            340                 345                 350

Tyr Gly Pro Gly Ile Ser Ala Ala Ala Ala Gly Ile Tyr Val Phe
            355                 360                 365

Gly Pro Gly Val Phe Gly Pro Tyr Gly Pro Gly Ala Ser Gly Pro Gly
370                 375                 380

Val Phe Gly Pro Tyr Gly Pro Gly Ala Ser Ala Ala Ala Ala Gly
385                 390                 395                 400

Pro Gly Ile Tyr Gly Pro Gly Val Phe Gly Pro Ser Ala Ser Ala Ala
            405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
            435                 440                 445

Tyr Gly Pro Gly Ala Ser Ala Ala Ala Ala Gly Ile Tyr Gly Pro
            450                 455                 460

Gly Val Phe Gly Pro Tyr Gly Pro Gly Ile Ser Ala Ala Ala Ala
465                 470                 475                 480

Gly Pro Gly Ser Gly Ile Tyr Gly Pro Gly Ala Ser Gly Ile Asn Gly
            485                 490                 495

Pro Gly Ser Gly Ile Tyr Gly Pro Gly Val Phe Gly Pro Gly Ile Ser
            500                 505                 510

Ala Ala Ala Ala Gly Ile Tyr Val Phe Gly Pro Gly Val Phe Gly
            515                 520                 525

Pro Tyr Gly Pro Gly Ala Ser Ala Ala Ala Ala Gly Ile Tyr Gly
            530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala
            565                 570                 575

Ala Ala Gly Pro Gly Ser Gly Val Phe Gly Pro Gly Ala Ser Gly Pro
            580                 585                 590

Gly Val Phe Gly Pro Tyr Gly Pro Gly Ala Ser Ala Ala Ala Ala
            595                 600                 605

Gly Ile Asn Gly Pro Gly Ser Gly Val Phe Gly Pro Gly Ile Ser Gly
            610                 615                 620
```

-continued

Ile Tyr Gly Pro Gly Val Phe Gly Pro Gly Val Phe Gly Pro Gly Ser
625             630             635             640

Ser Ala Ala Ala Ala Gly Pro Gly Ile Tyr Gly Pro Gly Val Phe
        645             650             655

Gly Pro Ser Ala Ser Ala Ala Ala Gly Pro Gly Ser Gly Val
    660             665             670

Phe Gly Pro Gly Ala Ser Gly Ile Tyr Gly Pro Gly Val Phe Gly Pro
        675             680             685

Gly Val Phe Gly Pro Gly Ser Ser Ala Ala Ala Ala Gly Ile Tyr
690             695             700

Gly Ser Gly Pro Gly Val Phe Gly Pro Tyr Gly Ser Ala Ala Ala
705             710             715             720

Ala Gly Pro Gly Ser Gly Ile Tyr Gly Ile Gly Pro Tyr Gly Pro Gly
        725             730             735

Ala Ser Gly Pro Gly Ile Tyr Gly Pro Gly Val Phe Gly Pro Ser Ala
        740             745             750

Ser Ala Ala Ala Ala Gly Ser Gly Val Phe Gly Pro Gly Ile Tyr
        755             760             765

Gly Pro Tyr Ala Ser Ala Ala Ala Ala Gly Ile Tyr Gly Ser Gly
770             775             780

Pro Gly Val Phe Gly Pro Tyr Gly Pro Gly Ile Ser Gly Ser Gly Val
785             790             795             800

Phe Gly Pro Gly Val Phe Gly Pro Tyr Ala Ser Ala Ala Ala Ala
        805             810             815

Gly Pro Gly Val Phe Gly Pro Tyr Gly Pro Gly Ser Ser Ala Ala Ala
        820             825             830

Ala Ala Gly Ile Tyr Gly Tyr Gly Pro Gly Val Phe Gly Pro Tyr Gly
835             840             845

Pro Gly Ala Ser Gly Ile Asn Gly Pro Gly Ser Gly Ile Tyr Gly Pro
850             855             860

Gly Val Phe Gly Pro Gly Ile Ser Ala Ala Ala Ala Gly Pro Gly
865             870             875             880

Val Phe Gly Pro Tyr Gly Pro Gly Ala Ser Ala Ala Ala Ala Gly
        885             890             895

Ile Tyr Gly Pro Gly Val Phe Gly Pro Gly Ile Tyr Gly Pro Gly Ser
        900             905             910

Ser Gly Pro Gly Val Phe Gly Pro Tyr Gly Pro Gly Ser Ser Ala Ala
        915             920             925

Ala Ala Ala Gly Ile Tyr Gly Pro Gly Val Phe Gly Pro Tyr Gly Pro
930             935             940

Gly Ile Ser Ala Ala Ala Ala Gly Ile Tyr Val Phe Gly Pro Gly
945             950             955             960

Val Phe Gly Pro Tyr Gly Pro Gly Ala Ser Gly Pro Gly Val Phe Gly
        965             970             975

Pro Tyr Gly Pro Gly Ala Ser Ala Ala Ala Ala Gly Pro Gly Ile
        980             985             990

Tyr Gly Pro Gly Val Phe Gly Pro Ser Ala Ser Ala Ala Ala Ala
        995             1000            1005

Gly Ile Tyr Gly Ser Gly Pro Gly Ile Tyr Gly Pro Tyr Gly Pro
        1010            1015            1020

Gly Ile Ser Gly Pro Gly Ser Gly Val Phe Gly Ile Gly Pro Tyr
        1025            1030            1035

```
Gly Pro Gly Ala Ser Ala Ala Ala Ala Gly Ile Tyr Gly Pro
    1040                1045                1050

Gly Val Phe Gly Pro Tyr Gly Pro Gly Ile Ser Ala Ala Ala Ala
    1055                1060                1065

Ala Gly Pro Gly Ser Gly Ile Tyr Gly Pro Gly Ala Ser Gly Ile
    1070                1075                1080

Asn Gly Pro Gly Ser Gly Ile Tyr Gly Pro Gly Val Phe Gly Pro
    1085                1090                1095

Gly Ile Ser Ala Ala Ala Ala Gly Ile Tyr Val Phe Gly Pro
    1100                1105                1110

Gly Val Phe Gly Pro Tyr Gly Pro Gly Ala Ser Ala Ala Ala
    1115                1120                1125

Ala Gly Ile Tyr Gly Ser Gly Pro Gly Val Phe Gly Pro Tyr Gly
    1130                1135                1140

Pro Gly Ile Ser Gly Ser Gly Val Phe Gly Pro Gly Val Phe Gly
    1145                1150                1155

Pro Tyr Ala Ser Ala Ala Ala Ala Ala Gly Pro Gly Ser Gly Val
    1160                1165                1170

Phe Gly Pro Gly Ala Ser
    1175

<210> SEQ ID NO 33
<211> LENGTH: 601
<212> TYPE: PRT
<213> ORGANISM: Artificial Sequence
<220> FEATURE:
<223> OTHER INFORMATION: PRT888

<400> SEQUENCE: 33

Met His His His His His Ser Ser Gly Ser Ser Gly Pro Gly Val
1               5                   10                  15

Leu Gly Pro Tyr Gly Pro Gly Ala Ser Ala Ala Ala Ala Gly Gln
                20                  25                  30

Asn Gly Pro Gly Ser Gly Val Leu Gly Pro Gly Gln Ser Gly Gln Tyr
                35                  40                  45

Gly Pro Gly Val Leu Gly Pro Gly Val Leu Gly Pro Gly Ser Ser Ala
    50                  55                  60

Ala Ala Ala Ala Gly Pro Gly Gln Tyr Gly Pro Gly Val Leu Gly Pro
65                  70                  75                  80

Ser Ala Ser Ala Ala Ala Ala Gly Pro Gly Ser Gly Val Leu Gly
                85                  90                  95

Pro Gly Ala Ser Gly Gln Tyr Gly Pro Gly Val Leu Gly Pro Gly Val
                100                 105                 110

Leu Gly Pro Gly Ser Ser Ala Ala Ala Ala Gly Gln Tyr Gly Ser
                115                 120                 125

Gly Pro Gly Val Leu Gly Pro Tyr Gly Ser Ala Ala Ala Ala Gly
                130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Val Leu Gly Pro Ser Ala Ser Ala
                165                 170                 175

Ala Ala Ala Ala Gly Ser Gly Val Leu Gly Pro Gly Gln Tyr Gly Pro
                180                 185                 190

Tyr Ala Ser Ala Ala Ala Ala Gly Gln Tyr Gly Ser Gly Pro Gly
                195                 200                 205
```

-continued

```
Val Leu Gly Pro Tyr Gly Pro Gly Gln Ser Gly Ser Gly Val Leu Gly
    210                 215                 220

Pro Gly Val Leu Gly Pro Tyr Ala Ser Ala Ala Ala Ala Ala Gly Pro
225                 230                 235                 240

Gly Val Leu Gly Pro Tyr Gly Pro Gly Ser Ser Ala Ala Ala Ala Ala
                245                 250                 255

Gly Gln Tyr Gly Tyr Gly Pro Gly Val Leu Gly Pro Tyr Gly Pro Gly
            260                 265                 270

Ala Ser Gly Gln Asn Gly Pro Gly Ser Gly Gln Tyr Gly Pro Gly Val
        275                 280                 285

Leu Gly Pro Gly Gln Ser Ala Ala Ala Ala Gly Pro Gly Val Leu
    290                 295                 300

Gly Pro Tyr Gly Pro Gly Ala Ser Ala Ala Ala Ala Gly Gln Tyr
305                 310                 315                 320

Gly Pro Gly Val Leu Gly Pro Gly Gln Tyr Gly Pro Gly Ser Ser Gly
                325                 330                 335

Pro Gly Val Leu Gly Pro Tyr Gly Pro Gly Ser Ser Ala Ala Ala
                340                 345                 350

Ala Gly Gln Tyr Gly Pro Gly Val Leu Gly Pro Tyr Gly Pro Gly Gln
        355                 360                 365

Ser Ala Ala Ala Ala Gly Gln Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Gln Tyr Gly
                405                 410                 415

Pro Gly Val Leu Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Val Leu Gly Gln Gly Pro Tyr Gly Pro Gly Ala
    450                 455                 460

Ser Ala Ala Ala Ala Gly Gln Tyr Gly Pro Gly Val Leu Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Val Leu Gly Pro Gly Gln Ser Ala Ala Ala Ala
        515                 520                 525

Gly Gln Tyr Val Leu Gly Pro Gly Val Leu Gly Pro Tyr Gly Pro Gly
    530                 535                 540

Ala Ser Ala Ala Ala Ala Gly Gln Tyr Gly Ser Gly Pro Gly Val
545                 550                 555                 560

Leu Gly Pro Tyr Gly Pro Gly Gln Ser Gly Ser Gly Val Leu Gly Pro
                565                 570                 575

Gly Val Leu Gly Pro Tyr Ala Ser Ala Ala Ala Ala Gly Pro Gly
                580                 585                 590

Ser Gly Val Leu Gly Pro Gly Ala Ser
            595                 600

<210> SEQ ID NO 34
<211> LENGTH: 601
<212> TYPE: PRT
```

<213> ORGANISM: Artificial Sequence
<220> FEATURE:
<223> OTHER INFORMATION: PRT965

<400> SEQUENCE: 34

Met His His His His His Ser Ser Gly Ser Ser Gly Pro Gly Thr
1               5                   10                  15

Ser Gly Pro Tyr Gly Pro Gly Ala Ser Ala Ala Ala Ala Gly Ala
                20                  25                  30

Asn Gly Pro Gly Ser Gly Thr Ser Gly Pro Gly Ala Ser Gly Ala Tyr
                35                  40                  45

Gly Pro Gly Thr Ser Gly Pro Gly Thr Ser Gly Pro Gly Ser Ser Ala
50                  55                  60

Ala Ala Ala Ala Gly Pro Gly Ala Tyr Gly Pro Gly Thr Ser Gly Pro
65                  70                  75                  80

Ser Ala Ser Ala Ala Ala Ala Gly Pro Gly Ser Gly Thr Ser Gly
                85                  90                  95

Pro Gly Ala Ser Gly Ala Tyr Gly Pro Gly Thr Ser Gly Pro Gly Thr
                100                 105                 110

Ser Gly Pro Gly Ser Ser Ala Ala Ala Ala Gly Ala Tyr Gly Ser
                115                 120                 125

Gly Pro Gly Thr Ser Gly Pro Tyr Gly Ser Ala Ala Ala Ala Gly
                130                 135                 140

Pro Gly Ser Gly Ala Tyr Gly Ala Gly Pro Tyr Gly Pro Gly Ala Ser
145                 150                 155                 160

Gly Pro Gly Ala Tyr Gly Pro Gly Thr Ser Gly Pro Ser Ala Ser Ala
                165                 170                 175

Ala Ala Ala Ala Gly Ser Gly Thr Ser Gly Pro Gly Ala Tyr Gly Pro
                180                 185                 190

Tyr Ala Ser Ala Ala Ala Ala Gly Ala Tyr Gly Ser Gly Pro Gly
                195                 200                 205

Thr Ser Gly Pro Tyr Gly Pro Gly Ala Ser Gly Ser Gly Thr Ser Gly
210                 215                 220

Pro Gly Thr Ser Gly Pro Tyr Ala Ser Ala Ala Ala Ala Gly Pro
225                 230                 235                 240

Gly Thr Ser Gly Pro Tyr Gly Pro Gly Ser Ser Ala Ala Ala Ala
                245                 250                 255

Gly Ala Tyr Gly Tyr Gly Pro Gly Thr Ser Gly Pro Tyr Gly Pro Gly
                260                 265                 270

Ala Ser Gly Ala Asn Gly Pro Gly Ser Gly Ala Tyr Gly Pro Gly Thr
                275                 280                 285

Ser Gly Pro Gly Ala Ser Ala Ala Ala Ala Gly Pro Gly Thr Ser
                290                 295                 300

Gly Pro Tyr Gly Pro Gly Ala Ser Ala Ala Ala Ala Gly Ala Tyr
305                 310                 315                 320

Gly Pro Gly Thr Ser Gly Pro Gly Ala Tyr Gly Pro Gly Ser Ser Gly
                325                 330                 335

Pro Gly Thr Ser Gly Pro Tyr Gly Pro Gly Ser Ser Ala Ala Ala Ala
                340                 345                 350

Ala Gly Ala Tyr Gly Pro Gly Thr Ser Gly Pro Tyr Gly Pro Gly Ala
                355                 360                 365

Ser Ala Ala Ala Ala Gly Ala Tyr Thr Ser Gly Pro Gly Thr Ser
370                 375                 380

Gly Pro Tyr Gly Pro Gly Ala Ser Gly Pro Gly Thr Ser Gly Pro Tyr

-continued

```
              385                 390                 395                 400
        Gly Pro Gly Ala Ser Ala Ala Ala Ala Gly Pro Gly Ala Tyr Gly
                        405                 410                 415
        Pro Gly Thr Ser Gly Pro Ser Ala Ser Ala Ala Ala Ala Gly Ala
                        420                 425                 430
        Tyr Gly Ser Gly Pro Gly Ala Tyr Gly Pro Tyr Gly Pro Gly Ala Ser
                        435                 440                 445
        Gly Pro Gly Ser Gly Thr Ser Gly Ala Gly Pro Tyr Gly Pro Gly Ala
                450                 455                 460
        Ser Ala Ala Ala Ala Gly Ala Tyr Gly Pro Gly Thr Ser Gly Pro
        465                 470                 475                 480
        Tyr Gly Pro Gly Ala Ser Ala Ala Ala Ala Gly Pro Gly Ser Gly
                        485                 490                 495
        Ala Tyr Gly Pro Gly Ala Ser Gly Ala Asn Gly Pro Gly Ser Gly Ala
                        500                 505                 510
        Tyr Gly Pro Gly Thr Ser Gly Pro Gly Ala Ser Ala Ala Ala Ala
                        515                 520                 525
        Gly Ala Tyr Thr Ser Gly Pro Gly Thr Ser Gly Pro Tyr Gly Pro Gly
                530                 535                 540
        Ala Ser Ala Ala Ala Ala Gly Ala Tyr Gly Ser Gly Pro Gly Thr
        545                 550                 555                 560
        Ser Gly Pro Tyr Gly Pro Gly Ala Ser Gly Ser Gly Thr Ser Gly Pro
                        565                 570                 575
        Gly Thr Ser Gly Pro Tyr Ala Ser Ala Ala Ala Ala Gly Pro Gly
                        580                 585                 590
        Ser Gly Thr Ser Gly Pro Gly Ala Ser
                        595                 600

<210> SEQ ID NO 35
<211> LENGTH: 601
<212> TYPE: PRT
<213> ORGANISM: Artificial Sequence
<220> FEATURE:
<223> OTHER INFORMATION: PRT889

<400> SEQUENCE: 35

Met His His His His His Ser Ser Gly Ser Ser Gly Pro Gly Val
1                   5                   10                  15
Leu Gly Pro Tyr Gly Pro Gly Ala Ser Ala Ala Ala Ala Gly Ile
                    20                  25                  30
Asn Gly Pro Gly Ser Gly Val Leu Gly Pro Gly Ile Ser Gly Ile Tyr
                35                  40                  45
Gly Pro Gly Val Leu Gly Pro Gly Val Leu Gly Pro Gly Ser Ser Ala
        50                  55                  60
Ala Ala Ala Gly Pro Gly Ile Tyr Gly Pro Gly Val Leu Gly Pro
65                  70                  75                  80
Ser Ala Ser Ala Ala Ala Ala Gly Pro Gly Ser Gly Val Leu Gly
                    85                  90                  95
Pro Gly Ala Ser Gly Ile Tyr Gly Pro Gly Val Leu Gly Pro Gly Val
                    100                 105                 110
Leu Gly Pro Gly Ser Ser Ala Ala Ala Ala Gly Ile Tyr Gly Ser
                115                 120                 125
Gly Pro Gly Val Leu Gly Pro Tyr Gly Ser Ala Ala Ala Ala Gly
        130                 135                 140
Pro Gly Ser Gly Ile Tyr Gly Ile Gly Pro Tyr Gly Pro Gly Ala Ser
```

```
            145                 150                 155                 160
        Gly Pro Gly Ile Tyr Gly Pro Gly Val Leu Gly Pro Ser Ala Ser Ala
                        165                 170                 175

Ala Ala Ala Ala Gly Ser Gly Val Leu Gly Pro Gly Ile Tyr Gly Pro
                        180                 185                 190

Tyr Ala Ser Ala Ala Ala Ala Gly Ile Tyr Gly Ser Gly Pro Gly
                    195                 200                 205

Val Leu Gly Pro Tyr Gly Pro Gly Ile Ser Gly Ser Gly Val Leu Gly
                    210                 215                 220

Pro Gly Val Leu Gly Pro Tyr Ala Ser Ala Ala Ala Ala Gly Pro
        225                 230                 235                 240

Gly Val Leu Gly Pro Tyr Gly Pro Gly Ser Ser Ala Ala Ala Ala
                            245                 250                 255

Gly Ile Tyr Gly Tyr Gly Pro Gly Val Leu Gly Pro Tyr Gly Pro Gly
                        260                 265                 270

Ala Ser Gly Ile Asn Gly Pro Gly Ser Gly Ile Tyr Gly Pro Gly Val
                    275                 280                 285

Leu Gly Pro Gly Ile Ser Ala Ala Ala Ala Gly Pro Gly Val Leu
                290                 295                 300

Gly Pro Tyr Gly Pro Gly Ala Ser Ala Ala Ala Ala Gly Ile Tyr
        305                 310                 315                 320

Gly Pro Gly Val Leu Gly Pro Ile Tyr Gly Pro Gly Ser Ser Gly
                        325                 330                 335

Pro Gly Val Leu Gly Pro Tyr Gly Pro Gly Ser Ser Ala Ala Ala Ala
                    340                 345                 350

Ala Gly Ile Tyr Gly Pro Gly Val Leu Gly Pro Tyr Gly Pro Gly Ile
                    355                 360                 365

Ser Ala Ala Ala Ala Gly Ile Tyr Val Leu Gly Pro Gly Val Leu
                    370                 375                 380

Gly Pro Tyr Gly Pro Gly Ala Ser Gly Pro Gly Val Leu Gly Pro Tyr
        385                 390                 395                 400

Gly Pro Gly Ala Ser Ala Ala Ala Ala Gly Pro Gly Ile Tyr Gly
                        405                 410                 415

Pro Gly Val Leu Gly Pro Ser Ala Ser Ala Ala Ala Ala Gly Ile
                    420                 425                 430

Tyr Gly Ser Gly Pro Gly Ile Tyr Gly Pro Tyr Gly Pro Gly Ile Ser
                    435                 440                 445

Gly Pro Gly Ser Gly Val Leu Gly Ile Gly Pro Tyr Gly Pro Gly Ala
        450                 455                 460

Ser Ala Ala Ala Ala Ala Gly Ile Tyr Gly Pro Gly Val Leu Gly Pro
        465                 470                 475                 480

Tyr Gly Pro Gly Ile Ser Ala Ala Ala Ala Gly Pro Gly Ser Gly
                        485                 490                 495

Ile Tyr Gly Pro Gly Ala Ser Gly Ile Asn Gly Pro Gly Ser Gly Ile
                    500                 505                 510

Tyr Gly Pro Gly Val Leu Gly Pro Gly Ile Ser Ala Ala Ala Ala
                    515                 520                 525

Gly Ile Tyr Val Leu Gly Pro Gly Val Leu Gly Pro Tyr Gly Pro Gly
                    530                 535                 540

Ala Ser Ala Ala Ala Ala Ala Gly Ile Tyr Gly Ser Gly Pro Gly Val
        545                 550                 555                 560

Leu Gly Pro Tyr Gly Pro Gly Ile Ser Gly Ser Gly Val Leu Gly Pro
                        565                 570                 575
```

```
Gly Val Leu Gly Pro Tyr Ala Ser Ala Ala Ala Ala Gly Pro Gly
            580                 585                 590

Ser Gly Val Leu Gly Pro Gly Ala Ser
            595                 600

<210> SEQ ID NO 36
<211> LENGTH: 601
<212> TYPE: PRT
<213> ORGANISM: Artificial Sequence
<220> FEATURE:
<223> OTHER INFORMATION: PRT916

<400> SEQUENCE: 36

Met His His His His His Ser Ser Gly Ser Ser Gly Pro Gly Val
1               5                   10                  15

Ile Gly Pro Tyr Gly Pro Gly Ala Ser Ala Ala Ala Ala Gly Leu
            20                  25                  30

Asn Gly Pro Gly Ser Gly Val Ile Gly Pro Gly Leu Ser Gly Leu Tyr
            35                  40                  45

Gly Pro Gly Val Ile Gly Pro Gly Val Ile Gly Pro Gly Ser Ser Ala
            50                  55                  60

Ala Ala Ala Gly Pro Gly Leu Tyr Gly Pro Gly Val Ile Gly Pro
65                  70                  75                  80

Ser Ala Ser Ala Ala Ala Ala Gly Pro Gly Ser Gly Val Ile Gly
            85                  90                  95

Pro Gly Ala Ser Gly Leu Tyr Gly Pro Gly Val Ile Gly Pro Gly Val
            100                 105                 110

Ile Gly Pro Gly Ser Ser Ala Ala Ala Ala Gly Leu Tyr Gly Ser
            115                 120                 125

Gly Pro Gly Val Ile Gly Pro Tyr Gly Ser Ala Ala Ala Ala Gly
            130                 135                 140

Pro Gly Ser Gly Leu Tyr Gly Leu Gly Pro Tyr Gly Pro Gly Ala Ser
145                 150                 155                 160

Gly Pro Gly Leu Tyr Gly Pro Gly Val Ile Gly Pro Ser Ala Ser Ala
            165                 170                 175

Ala Ala Ala Gly Ser Gly Val Ile Gly Pro Gly Leu Tyr Gly Pro
            180                 185                 190

Tyr Ala Ser Ala Ala Ala Ala Gly Leu Tyr Gly Ser Gly Pro Gly
            195                 200                 205

Val Ile Gly Pro Tyr Gly Pro Gly Leu Ser Gly Ser Gly Val Ile Gly
            210                 215                 220

Pro Gly Val Ile Gly Pro Tyr Ala Ser Ala Ala Ala Ala Gly Pro
225                 230                 235                 240

Gly Val Ile Gly Pro Tyr Gly Pro Gly Ser Ser Ala Ala Ala Ala
            245                 250                 255

Gly Leu Tyr Gly Tyr Gly Pro Gly Val Ile Gly Pro Tyr Gly Pro Gly
            260                 265                 270

Ala Ser Gly Leu Asn Gly Pro Gly Ser Gly Leu Tyr Gly Pro Gly Val
            275                 280                 285

Ile Gly Pro Gly Leu Ser Ala Ala Ala Ala Gly Pro Gly Val Ile
            290                 295                 300

Gly Pro Tyr Gly Pro Gly Ala Ser Ala Ala Ala Ala Gly Leu Tyr
305                 310                 315                 320

Gly Pro Gly Val Ile Gly Pro Gly Leu Tyr Gly Pro Gly Ser Ser Gly
            325                 330                 335
```

```
Pro Gly Val Ile Gly Pro Tyr Gly Pro Gly Ser Ser Ala Ala Ala Ala
                340                 345                 350

Ala Gly Leu Tyr Gly Pro Gly Val Ile Gly Pro Tyr Gly Pro Gly Leu
                355                 360                 365

Ser Ala Ala Ala Ala Gly Leu Tyr Val Ile Gly Pro Gly Val Ile
370                 375                 380

Gly Pro Tyr Gly Pro Gly Ala Ser Gly Pro Gly Val Ile Gly Pro Tyr
385                 390                 395                 400

Gly Pro Gly Ala Ser Ala Ala Ala Ala Gly Pro Gly Leu Tyr Gly
                405                 410                 415

Pro Gly Val Ile Gly Pro Ser Ala Ser Ala Ala Ala Ala Gly Leu
                420                 425                 430

Tyr Gly Ser Gly Pro Gly Leu Tyr Gly Pro Tyr Gly Pro Gly Leu Ser
                435                 440                 445

Gly Pro Gly Ser Gly Val Ile Gly Leu Gly Pro Tyr Gly Pro Gly Ala
                450                 455                 460

Ser Ala Ala Ala Ala Gly Leu Tyr Gly Pro Gly Val Ile Gly Pro
465                 470                 475                 480

Tyr Gly Pro Gly Leu Ser Ala Ala Ala Ala Gly Pro Gly Ser Gly
                485                 490                 495

Leu Tyr Gly Pro Gly Ala Ser Gly Leu Asn Gly Pro Gly Ser Gly Leu
                500                 505                 510

Tyr Gly Pro Gly Val Ile Gly Pro Gly Leu Ser Ala Ala Ala Ala
                515                 520                 525

Gly Leu Tyr Val Ile Gly Pro Gly Val Ile Gly Pro Tyr Gly Pro Gly
                530                 535                 540

Ala Ser Ala Ala Ala Ala Gly Leu Tyr Gly Ser Gly Pro Gly Val
545                 550                 555                 560

Ile Gly Pro Tyr Gly Pro Gly Leu Ser Gly Ser Gly Val Ile Gly Pro
                565                 570                 575

Gly Val Ile Gly Pro Tyr Ala Ser Ala Ala Ala Ala Gly Pro Gly
                580                 585                 590

Ser Gly Val Ile Gly Pro Gly Ala Ser
                595                 600
```

<210> SEQ ID NO 37
<211> LENGTH: 601
<212> TYPE: PRT
<213> ORGANISM: Artificial Sequence
<220> FEATURE:
<223> OTHER INFORMATION: PRT918

<400> SEQUENCE: 37

```
Met His His His His His Ser Ser Gly Ser Gly Pro Gly Val
1               5                   10                  15

Phe Gly Pro Tyr Gly Pro Gly Ala Ser Ala Ala Ala Ala Gly Ile
                20                  25                  30

Asn Gly Pro Gly Ser Gly Val Phe Gly Pro Gly Ile Ser Gly Ile Tyr
                35                  40                  45

Gly Pro Gly Val Phe Gly Pro Gly Val Phe Gly Pro Gly Ser Ser Ala
                50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Ala Gly Pro Gly Ser Gly Val Phe Gly
                85                  90                  95
```

```
Pro Gly Ala Ser Gly Ile Tyr Gly Pro Gly Val Phe Gly Pro Gly Val
                100                 105                 110
Phe Gly Pro Gly Ser Ser Ala Ala Ala Ala Gly Ile Tyr Gly Ser
            115                 120                 125
Gly Pro Gly Val Phe Gly Pro Tyr Gly Ala Ala Ala Ala Gly
        130                 135                 140
Pro Gly Ser Gly Ile Tyr Gly Ile Gly Pro Tyr Gly Pro Gly Ala Ser
145                 150                 155                 160
Gly Pro Gly Ile Tyr Gly Pro Gly Val Phe Gly Pro Ser Ala Ser Ala
                165                 170                 175
Ala Ala Ala Ala Gly Ser Gly Val Phe Gly Pro Gly Ile Tyr Gly Pro
            180                 185                 190
Tyr Ala Ser Ala Ala Ala Ala Gly Ile Tyr Gly Ser Gly Pro Gly
        195                 200                 205
Val Phe Gly Pro Tyr Gly Pro Gly Ile Ser Gly Ser Gly Val Phe Gly
        210                 215                 220
Pro Gly Val Phe Gly Pro Tyr Ala Ser Ala Ala Ala Ala Gly Pro
225                 230                 235                 240
Gly Val Phe Gly Pro Tyr Gly Pro Gly Ser Ser Ala Ala Ala Ala
                245                 250                 255
Gly Ile Tyr Gly Tyr Gly Pro Gly Val Phe Gly Pro Tyr Gly Pro Gly
            260                 265                 270
Ala Ser Gly Ile Asn Gly Pro Gly Ser Gly Ile Tyr Gly Pro Gly Val
        275                 280                 285
Phe Gly Pro Gly Ile Ser Ala Ala Ala Ala Gly Pro Gly Val Phe
        290                 295                 300
Gly Pro Tyr Gly Pro Gly Ala Ser Ala Ala Ala Ala Gly Ile Tyr
305                 310                 315                 320
Gly Pro Gly Val Phe Gly Pro Gly Ile Tyr Gly Pro Gly Ser Ser Gly
                325                 330                 335
Pro Gly Val Phe Gly Pro Tyr Gly Pro Gly Ser Ser Ala Ala Ala Ala
            340                 345                 350
Ala Gly Ile Tyr Gly Pro Gly Val Phe Gly Pro Tyr Gly Pro Gly Ile
        355                 360                 365
Ser Ala Ala Ala Ala Gly Ile Tyr Val Phe Gly Pro Gly Val Phe
        370                 375                 380
Gly Pro Tyr Gly Pro Gly Ala Ser Gly Pro Gly Val Phe Gly Pro Tyr
385                 390                 395                 400
Gly Pro Gly Ala Ser Ala Ala Ala Ala Gly Pro Gly Ile Tyr Gly
                405                 410                 415
Pro Gly Val Phe Gly Pro Ser Ala Ser Ala Ala Ala Ala Gly Ile
            420                 425                 430
Tyr Gly Ser Gly Pro Gly Ile Tyr Gly Pro Tyr Gly Pro Gly Ile Ser
        435                 440                 445
Gly Pro Gly Ser Gly Val Phe Gly Ile Gly Pro Tyr Gly Pro Gly Ala
        450                 455                 460
Ser Ala Ala Ala Ala Gly Ile Tyr Gly Pro Gly Val Phe Gly Pro
465                 470                 475                 480
Tyr Gly Pro Gly Ile Ser Ala Ala Ala Ala Gly Pro Gly Ser Gly
                485                 490                 495
Ile Tyr Gly Pro Gly Ala Ser Gly Ile Asn Gly Pro Gly Ser Gly Ile
            500                 505                 510
```

```
Tyr Gly Pro Gly Val Phe Gly Pro Gly Ile Ser Ala Ala Ala Ala Ala
            515                 520                 525

Gly Ile Tyr Val Phe Gly Pro Gly Val Phe Gly Pro Tyr Gly Pro Gly
    530                 535                 540

Ala Ser Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Gly Pro Gly
            580                 585                 590

Ser Gly Val Phe Gly Pro Gly Ala Ser
            595                 600

<210> SEQ ID NO 38
<211> LENGTH: 576
<212> TYPE: PRT
<213> ORGANISM: Artificial Sequence
<220> FEATURE:
<223> OTHER INFORMATION: PRT699

<400> SEQUENCE: 38

Met His His His His His Ser Ser Gly Ser Ser Gly Pro Gly Val
1               5                   10                  15

Leu Gly Pro Tyr Gly Pro Gly Ala Ser Ala Ala Ala Ala Ala Ala
                20                  25                  30

Gly Ser Asn Gly Pro Gly Ser Gly Val Leu Gly Pro Gly Gln Ser Gly
            35                  40                  45

Gln Tyr Gly Pro Gly Val Leu Gly Pro Gly Val Leu Gly Pro Gly Ser
50                  55                  60

Ser Ala Ala Ala Ala Ala Ala Gly Pro Gly Gln Tyr Gly Pro Gly
65                  70                  75                  80

Val Leu Gly Pro Ser Ala Ser Ala Ala Ala Ala Ala Gly Pro
                85                  90                  95

Gly Ser Gly Val Leu Gly Pro Gly Ala Ser Gly Gln Tyr Gly Pro Gly
            100                 105                 110

Val Leu Gly Pro Gly Val Leu Gly Pro Gly Ser Ala Ala Ala Ala
                115                 120                 125

Ala Ala Ala Gly Ser Tyr Gly Ser Gly Pro Gly Val Leu Gly Pro Tyr
130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Val Leu Gly Pro Ser Ala Ser Ala Ala Ala Ala Ala Ala
            180                 185                 190

Gly Ser Gly Val Leu Gly Pro Gly Gln Tyr Gly Pro Tyr Ala Ser Ala
            195                 200                 205

Ala Ala Ala Ala Ala Gly Ser Tyr Gly Ser Gly Pro Gly Val Leu
210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Gly Pro
                245                 250                 255

Gly Val Leu Gly Pro Tyr Gly Pro Gly Ser Ser Ala Ala Ala Ala
            260                 265                 270
```

```
Ala Ala Gly Ser Tyr Gly Tyr Gly Pro Gly Val Leu Gly Pro Tyr Gly
            275                 280                 285

Pro Gly Ala Ser Gly Gln Asn Gly Pro Gly Ser Gly Gln Tyr Gly Pro
        290                 295                 300

Gly Val Leu Gly Pro Gly Pro Ser Ala Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Gln Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Gly Ser Tyr Gly Pro Gly Val
370                 375                 380

Leu Gly Pro Tyr Gly Pro Gly Pro Ser Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
                420                 425                 430

Ala Ala Ala Ala Ala Gly Pro Gly Gln Tyr Gly Pro Gly Val Leu
            435                 440                 445

Gly Pro Ser Ala Ser Ala Ala Ala Ala Gly Ser Tyr Gly
        450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Gly Pro Tyr Gly Pro Gly Ala Ser Ala
                485                 490                 495

Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Gly Pro Gly
        515                 520                 525

Ser Gly Gln Tyr Gly Pro Gly Ala Ser Gly Gln Asn Gly Pro Gly Ser
530                 535                 540

Gly Gln Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
            565                 570                 575

<210> SEQ ID NO 39
<211> LENGTH: 576
<212> TYPE: PRT
<213> ORGANISM: Artificial Sequence
<220> FEATURE:
<223> OTHER INFORMATION: PRT698

<400> SEQUENCE: 39

Met His His His His His His Ser Ser Gly Ser Ser Gly Pro Gly Val
1               5                   10                  15

Leu Gly Pro Tyr Gly Pro Gly Ala Ser Ala Ala Ala Ala Ala Ala Ala
            20                  25                  30

Gly Ser Asn Gly Pro Gly Ser Gly Val Leu Gly Pro Gly Ile Ser Gly
        35                  40                  45

Ile Tyr Gly Pro Gly Val Leu Gly Pro Gly Val Leu Gly Pro Gly Ser
    50                  55                  60
```

```
Ser Ala Ala Ala Ala Ala Ala Gly Pro Gly Ile Tyr Gly Pro Gly
65                  70                  75                  80

Val Leu Gly Pro Ser Ala Ser Ala Ala Ala Ala Ala Gly Pro
                85                  90                  95

Gly Ser Gly Val Leu Gly Pro Gly Ala Ser Gly Ile Tyr Gly Pro Gly
            100                 105                 110

Val Leu Gly Pro Gly Val Leu Gly Pro Gly Ser Ser Ala Ala Ala
            115                 120                 125

Ala Ala Ala Gly Ser Tyr Gly Ser Gly Pro Gly Val Leu Gly Pro Tyr
        130                 135                 140

Gly Ser Ala Ala Ala Ala Ala Ala Gly Pro Gly Ser Gly Ile Tyr
145                 150                 155                 160

Gly Ile Gly Pro Tyr Gly Pro Gly Ala Ser Gly Pro Gly Ile Tyr Gly
                165                 170                 175

Pro Gly Val Leu Gly Pro Ser Ala Ser Ala Ala Ala Ala Ala Ala
            180                 185                 190

Gly Ser Gly Val Leu Gly Pro Gly Ile Tyr Gly Pro Tyr Ala Ser Ala
        195                 200                 205

Ala Ala Ala Ala Ala Gly Ser Tyr Gly Ser Gly Pro Gly Val Leu
210                 215                 220

Gly Pro Tyr Gly Pro Gly Ile Ser Gly Ser Gly Val Leu Gly Pro Gly
225                 230                 235                 240

Val Leu Gly Pro Tyr Ala Ser Ala Ala Ala Ala Ala Ala Gly Pro
                245                 250                 255

Gly Val Leu Gly Pro Tyr Gly Pro Gly Ser Ser Ala Ala Ala Ala
            260                 265                 270

Ala Ala Gly Ser Tyr Gly Tyr Gly Pro Gly Val Leu Gly Pro Tyr Gly
        275                 280                 285

Pro Gly Ala Ser Gly Ile Asn Gly Pro Gly Ser Gly Ile Tyr Gly Pro
            290                 295                 300

Gly Val Leu Gly Pro Gly Pro Ser Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Ile Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Gly Ser Tyr Gly Pro Gly Val
370                 375                 380

Leu Gly Pro Tyr Gly Pro Gly Pro Ser Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
            420                 425                 430

Ala Ala Ala Ala Ala Gly Pro Gly Ile Tyr Gly Pro Gly Val Leu
435                 440                 445

Gly Pro Ser Ala Ser Ala Ala Ala Ala Ala Gly Ser Tyr Gly
            450                 455                 460

Ser Gly Pro Gly Ile Tyr Gly Pro Tyr Gly Pro Gly Ile Ser Gly Pro
465                 470                 475                 480

Gly Ser Gly Val Leu Gly Ile Gly Pro Tyr Gly Pro Gly Ala Ser Ala
```

```
                        485             490             495
Ala Ala Ala Ala Ala Ala Gly Ser Tyr Gly Pro Gly Val Leu Gly Pro
                    500             505             510

Tyr Gly Pro Gly Pro Ser Ala Ala Ala Ala Ala Ala Gly Pro Gly
            515                 520             525

Ser Gly Ile Tyr Gly Pro Gly Ala Ser Gly Ile Asn Gly Pro Gly Ser
            530             535             540

Gly Ile Tyr Gly Pro Gly Val Leu Gly Pro Gly Pro Ser Ala Ala Ala
545             550             555             560

Ala Ala Ala Ala Gly Pro Gly Ser Gly Val Leu Gly Pro Gly Ala Ser
                565             570             575

<210> SEQ ID NO 40
<211> LENGTH: 1190
<212> TYPE: PRT
<213> ORGANISM: Artificial Sequence
<220> FEATURE:
<223> OTHER INFORMATION: PRT966

<400> SEQUENCE: 40

Met His His His His His Ser Ser Gly Ser Ser Gly Pro Gly Val
1               5                   10              15

Phe Gly Pro Tyr Gly Pro Gly Ala Ser Ala Ala Ala Ala Gly Ile
                20              25              30

Asn Gly Pro Gly Ser Gly Val Phe Gly Pro Gly Ile Ser Gly Ile Tyr
            35              40              45

Gly Pro Gly Val Phe Gly Pro Gly Val Phe Gly Pro Gly Ser Ser Ala
50              55              60

Ala Ala Ala Ala Gly Pro Gly Ile Tyr Gly Pro Gly Val Phe Gly Pro
65              70              75              80

Ser Ala Ser Ala Ala Ala Ala Gly Pro Gly Ser Gly Val Phe Gly
                85              90              95

Pro Gly Ala Ser Gly Ile Tyr Gly Pro Gly Val Phe Gly Pro Gly Val
            100             105             110

Phe Gly Pro Gly Ser Ser Ala Ala Ala Ala Gly Ile Tyr Gly Ser
            115             120             125

Gly Pro Gly Val Phe Gly Pro Tyr Gly Ser Ala Ala Ala Ala Gly
            130             135             140

Pro Gly Ser Gly Ile Tyr Gly Ile Gly Pro Tyr Gly Pro Gly Ala Ser
145             150             155             160

Gly Pro Gly Ile Tyr Gly Pro Gly Val Phe Gly Pro Ser Ala Ser Ala
                165             170             175

Ala Ala Ala Gly Ser Gly Val Phe Gly Pro Gly Ile Tyr Gly Pro
            180             185             190

Tyr Ala Ser Ala Ala Ala Ala Gly Ile Tyr Gly Ser Gly Pro Gly
            195             200             205

Val Phe Gly Pro Tyr Gly Pro Gly Ile Ser Gly Ser Gly Val Phe Gly
            210             215             220

Pro Gly Val Phe Gly Pro Tyr Ala Ser Ala Ala Ala Ala Gly Pro
225             230             235             240

Gly Val Phe Gly Pro Tyr Gly Pro Gly Ser Ser Ala Ala Ala Ala
                245             250             255

Gly Ile Tyr Gly Tyr Gly Pro Gly Val Phe Gly Pro Tyr Gly Pro Gly
            260             265             270

Ala Ser Gly Ile Asn Gly Pro Gly Ser Gly Ile Tyr Gly Pro Gly Val
```

-continued

```
                275                 280                 285
Phe Gly Pro Gly Ile Ser Ala Ala Ala Ala Gly Pro Val Phe
    290                 295                 300
Gly Pro Tyr Gly Pro Gly Ala Ser Ala Ala Ala Ala Gly Ile Tyr
305                 310                 315                 320
Gly Pro Gly Val Phe Gly Pro Gly Ile Tyr Gly Pro Gly Ser Ser Gly
                325                 330                 335
Pro Gly Val Phe Gly Pro Tyr Gly Pro Gly Ser Ser Ala Ala Ala
                340                 345                 350
Ala Gly Ile Tyr Gly Pro Gly Val Phe Gly Pro Tyr Gly Pro Gly Ile
                355                 360                 365
Ser Ala Ala Ala Ala Gly Ile Tyr Val Phe Gly Pro Gly Val Phe
    370                 375                 380
Gly Pro Tyr Gly Pro Gly Ala Ser Gly Pro Gly Val Phe Gly Pro Tyr
385                 390                 395                 400
Gly Pro Gly Ala Ser Ala Ala Ala Ala Gly Pro Gly Ile Tyr Gly
                405                 410                 415
Pro Gly Val Phe Gly Pro Ser Ala Ser Ala Ala Ala Ala Gly Ile
                420                 425                 430
Tyr Gly Ser Gly Pro Gly Ile Tyr Gly Pro Tyr Gly Pro Gly Ile Ser
                435                 440                 445
Gly Pro Gly Ser Gly Val Phe Gly Ile Gly Pro Tyr Gly Pro Gly Ala
    450                 455                 460
Ser Ala Ala Ala Ala Gly Ile Tyr Gly Pro Gly Val Phe Gly Pro
465                 470                 475                 480
Tyr Gly Pro Gly Ile Ser Ala Ala Ala Ala Gly Pro Gly Ser Gly
                485                 490                 495
Ile Tyr Gly Pro Gly Ala Ser Gly Ile Asn Gly Pro Gly Ser Gly Ile
                500                 505                 510
Tyr Gly Pro Gly Val Phe Gly Pro Gly Ile Ser Ala Ala Ala Ala
                515                 520                 525
Gly Ile Tyr Val Phe Gly Pro Gly Val Phe Gly Pro Tyr Gly Pro Gly
    530                 535                 540
Ala Ser Ala Ala Ala Ala Gly Ile Tyr Gly Ser Gly Pro Gly Val
545                 550                 555                 560
Phe Gly Pro Tyr Gly Pro Gly Ile Ser Gly Ser Gly Val Phe Gly Pro
                565                 570                 575
Gly Val Phe Gly Pro Tyr Ala Ser Ala Ala Ala Ala Gly Pro Gly
                580                 585                 590
Ser Gly Val Phe Gly Pro Gly Ala Ser Gly Pro Gly Val Phe Gly Pro
                595                 600                 605
Tyr Gly Pro Gly Ala Ser Ala Ala Ala Ala Gly Ile Asn Gly Pro
                610                 615                 620
Gly Ser Gly Val Phe Gly Pro Gly Ile Ser Gly Ile Tyr Gly Pro Gly
625                 630                 635                 640
Val Phe Gly Pro Gly Val Phe Gly Pro Gly Ser Ser Ala Ala Ala
                645                 650                 655
Ala Gly Pro Gly Ile Tyr Gly Pro Gly Val Phe Gly Pro Ser Ala Ser
                660                 665                 670
Ala Ala Ala Ala Gly Pro Gly Ser Gly Val Phe Gly Pro Gly Ala
                675                 680                 685
Ser Gly Ile Tyr Gly Pro Gly Val Phe Gly Pro Gly Val Phe Gly Pro
    690                 695                 700
```

```
Gly Ser Ser Ala Ala Ala Ala Gly Ile Tyr Gly Ser Gly Pro Gly
705                 710                 715                 720

Val Phe Gly Pro Tyr Gly Ser Ala Ala Ala Gly Pro Gly Ser
        725                 730                 735

Gly Ile Tyr Gly Ile Gly Pro Tyr Gly Pro Gly Ala Ser Gly Pro Gly
            740                 745                 750

Ile Tyr Gly Pro Gly Val Phe Gly Pro Ser Ala Ser Ala Ala Ala
        755                 760                 765

Ala Gly Ser Gly Val Phe Gly Pro Gly Ile Tyr Gly Pro Tyr Ala Ser
770                 775                 780

Ala Ala Ala Ala Ala Gly Ile Tyr Gly Ser Gly Pro Gly Val Phe Gly
785                 790                 795                 800

Pro Tyr Gly Pro Gly Ile Ser Gly Ser Gly Val Phe Gly Pro Gly Val
            805                 810                 815

Phe Gly Pro Tyr Ala Ser Ala Ala Ala Ala Gly Pro Gly Val Phe
        820                 825                 830

Gly Pro Tyr Gly Pro Gly Ser Ser Ala Ala Ala Ala Gly Ile Tyr
        835                 840                 845

Gly Tyr Gly Pro Gly Val Phe Gly Pro Tyr Gly Pro Gly Ala Ser Gly
850                 855                 860

Ile Asn Gly Pro Gly Ser Gly Ile Tyr Gly Pro Gly Val Phe Gly Pro
865                 870                 875                 880

Gly Ile Ser Ala Ala Ala Ala Gly Pro Gly Val Phe Gly Pro Tyr
            885                 890                 895

Gly Pro Gly Ala Ser Ala Ala Ala Ala Gly Ile Tyr Gly Pro Gly
        900                 905                 910

Val Phe Gly Pro Gly Ile Tyr Gly Pro Gly Ser Ser Gly Pro Gly Val
            915                 920                 925

Phe Gly Pro Tyr Gly Pro Gly Ser Ser Ala Ala Ala Ala Gly Ile
        930                 935                 940

Tyr Gly Pro Gly Val Phe Gly Pro Tyr Gly Pro Gly Ile Ser Ala Ala
945                 950                 955                 960

Ala Ala Gly Ile Tyr Val Phe Gly Pro Gly Val Phe Gly Pro Tyr
            965                 970                 975

Gly Pro Gly Ala Ser Gly Pro Gly Val Phe Gly Pro Tyr Gly Pro Gly
            980                 985                 990

Ala Ser Ala Ala Ala Ala Gly Pro Gly Ile Tyr Gly Pro Gly Val
        995                 1000                1005

Phe Gly Pro Ser Ala Ser Ala Ala Ala Ala Gly Ile Tyr Gly
1010                1015                1020

Ser Gly Pro Gly Ile Tyr Gly Pro Tyr Gly Pro Gly Ile Ser Gly
    1025                1030                1035

Pro Gly Ser Gly Val Phe Ile Gly Pro Tyr Gly Pro Gly Ala
    1040                1045                1050

Ser Ala Ala Ala Ala Gly Ile Tyr Gly Pro Gly Val Phe Gly
    1055                1060                1065

Pro Tyr Gly Pro Gly Ile Ser Ala Ala Ala Ala Ala Gly Pro Gly
    1070                1075                1080

Ser Gly Ile Tyr Gly Pro Gly Ala Ser Gly Ile Asn Gly Pro Gly
    1085                1090                1095

Ser Gly Ile Tyr Gly Pro Gly Val Phe Gly Pro Gly Ile Ser Ala
    1100                1105                1110
```

-continued

```
Ala Ala Ala Ala Gly Ile Tyr Val Phe Gly Pro Gly Val Phe Gly
    1115                1120                1125

Pro Tyr Gly Pro Gly Ala Ser Ala Ala Ala Ala Gly Ile Tyr
    1130                1135                1140

Gly Ser Gly Pro Gly Val Phe Gly Pro Tyr Gly Pro Gly Ile Ser
    1145                1150                1155

Gly Ser Gly Val Phe Gly Pro Gly Val Phe Gly Pro Tyr Ala Ser
    1160                1165                1170

Ala Ala Ala Ala Ala Gly Pro Gly Ser Gly Val Phe Gly Pro Gly
    1175                1180                1185

Ala Ser
    1190

<210> SEQ ID NO 41
<211> LENGTH: 590
<212> TYPE: PRT
<213> ORGANISM: Artificial Sequence
<220> FEATURE:
<223> OTHER INFORMATION: Met-PRT917

<400> SEQUENCE: 41

Met Gly Pro Gly Leu Ile Gly Pro Tyr Gly Pro Gly Ala Ser Ala Ala
1               5                   10                  15

Ala Ala Ala Gly Val Asn Gly Pro Gly Ser Gly Leu Ile Gly Pro Gly
            20                  25                  30

Val Ser Gly Val Tyr Gly Pro Gly Leu Ile Gly Pro Gly Leu Ile Gly
        35                  40                  45

Pro Gly Ser Ser Ala Ala Ala Ala Gly Pro Gly Val Tyr Gly Pro
    50                  55                  60

Gly Leu Ile Gly Pro Ser Ala Ser Ala Ala Ala Ala Gly Pro Gly
65                  70                  75                  80

Ser Gly Leu Ile Gly Pro Gly Ala Ser Gly Val Tyr Gly Pro Gly Leu
                85                  90                  95

Ile Gly Pro Gly Leu Ile Gly Pro Gly Ser Ser Ala Ala Ala Ala
            100                 105                 110

Gly Val Tyr Gly Ser Gly Pro Gly Leu Ile Gly Pro Tyr Gly Ser Ala
        115                 120                 125

Ala Ala Ala Ala Gly Pro Gly Ser Gly Val Tyr Gly Val Gly Pro Tyr
    130                 135                 140

Gly Pro Gly Ala Ser Gly Pro Gly Val Tyr Gly Pro Gly Leu Ile Gly
145                 150                 155                 160

Pro Ser Ala Ser Ala Ala Ala Ala Gly Ser Gly Leu Ile Gly Pro
                165                 170                 175

Gly Val Tyr Gly Pro Tyr Ala Ser Ala Ala Ala Ala Gly Val Tyr
        180                 185                 190

Gly Ser Gly Pro Gly Leu Ile Gly Pro Tyr Gly Pro Gly Val Ser Gly
    195                 200                 205

Ser Gly Leu Ile Gly Pro Gly Leu Ile Gly Pro Tyr Ala Ser Ala Ala
    210                 215                 220

Ala Ala Ala Gly Pro Gly Leu Ile Gly Pro Tyr Gly Pro Gly Ser Ser
225                 230                 235                 240

Ala Ala Ala Ala Ala Gly Val Tyr Gly Tyr Gly Pro Gly Leu Ile Gly
                245                 250                 255

Pro Tyr Gly Pro Gly Ala Ser Gly Val Asn Gly Pro Gly Ser Gly Val
            260                 265                 270
```

```
Tyr Gly Pro Gly Leu Ile Gly Pro Gly Val Ser Ala Ala Ala Ala
            275                 280                 285
Gly Pro Gly Leu Ile Gly Pro Tyr Gly Pro Gly Ala Ser Ala Ala
        290                 295                 300
Ala Ala Gly Val Tyr Gly Pro Gly Leu Ile Gly Pro Gly Val Tyr Gly
305                 310                 315                 320
Pro Gly Ser Ser Gly Pro Gly Leu Ile Gly Pro Tyr Gly Pro Gly Ser
                325                 330                 335
Ser Ala Ala Ala Ala Gly Val Tyr Gly Pro Gly Leu Ile Gly Pro
        340                 345                 350
Tyr Gly Pro Gly Val Ser Ala Ala Ala Ala Gly Val Tyr Leu Ile
        355                 360                 365
Gly Pro Gly Leu Ile Gly Pro Tyr Gly Pro Gly Ala Ser Gly Pro Gly
        370                 375                 380
Leu Ile Gly Pro Tyr Gly Pro Gly Ala Ser Ala Ala Ala Ala Gly
385                 390                 395                 400
Pro Gly Val Tyr Gly Pro Gly Leu Ile Gly Pro Ser Ala Ser Ala Ala
                405                 410                 415
Ala Ala Ala Gly Val Tyr Gly Ser Gly Pro Gly Val Tyr Gly Pro Tyr
            420                 425                 430
Gly Pro Gly Val Ser Gly Pro Gly Ser Gly Leu Ile Gly Val Gly Pro
        435                 440                 445
Tyr Gly Pro Gly Ala Ser Ala Ala Ala Ala Gly Val Tyr Gly Pro
        450                 455                 460
Gly Leu Ile Gly Pro Tyr Gly Pro Gly Val Ser Ala Ala Ala Ala
465                 470                 475                 480
Gly Pro Gly Ser Gly Val Tyr Gly Pro Gly Ala Ser Gly Val Asn Gly
                485                 490                 495
Pro Gly Ser Gly Val Tyr Gly Pro Gly Leu Ile Gly Pro Gly Val Ser
                500                 505                 510
Ala Ala Ala Ala Ala Gly Val Tyr Leu Ile Gly Pro Gly Leu Ile Gly
            515                 520                 525
Pro Tyr Gly Pro Gly Ala Ser Ala Ala Ala Ala Gly Val Tyr Gly
        530                 535                 540
Ser Gly Pro Gly Leu Ile Gly Pro Tyr Gly Pro Gly Val Ser Gly Ser
545                 550                 555                 560
Gly Leu Ile Gly Pro Gly Leu Ile Gly Pro Tyr Ala Ser Ala Ala Ala
                565                 570                 575
Ala Ala Gly Pro Gly Ser Gly Leu Ile Gly Pro Gly Ala Ser
            580                 585                 590

<210> SEQ ID NO 42
<211> LENGTH: 587
<212> TYPE: PRT
<213> ORGANISM: Artificial Sequence
<220> FEATURE:
<223> OTHER INFORMATION: Met-PRT1028

<400> SEQUENCE: 42

Met Gly Pro Gly Ile Phe Gly Pro Tyr Gly Pro Gly Ala Ser Ala Ala
1               5                   10                  15
Ala Ala Ala Gly Thr Gly Pro Gly Ser Gly Ile Phe Gly Pro Gly Thr
            20                  25                  30
Ser Gly Thr Tyr Gly Pro Gly Ile Phe Gly Pro Gly Ile Phe Gly Pro
        35                  40                  45
```

```
Gly Ser Ser Ala Ala Ala Ala Gly Pro Gly Thr Tyr Gly Pro Gly
     50                  55                  60

Ile Phe Gly Pro Ser Ala Ser Ala Ala Ala Ala Gly Pro Gly Ser
 65                  70                  75                  80

Gly Ile Phe Gly Pro Gly Ala Ser Gly Thr Tyr Gly Pro Gly Ile Phe
             85                  90                  95

Gly Pro Gly Ile Phe Gly Pro Gly Ser Ser Ala Ala Ala Ala Gly
            100                 105                 110

Thr Tyr Gly Ser Gly Pro Gly Ile Phe Gly Pro Tyr Gly Ser Ala Ala
            115                 120                 125

Ala Ala Ala Gly Pro Gly Ser Gly Thr Tyr Gly Thr Gly Pro Tyr Gly
            130                 135                 140

Pro Gly Ala Ser Gly Pro Gly Thr Tyr Gly Pro Gly Ile Phe Gly Pro
145                 150                 155                 160

Ser Ala Ser Ala Ala Ala Ala Gly Ser Gly Ile Phe Gly Pro Gly
                165                 170                 175

Thr Tyr Gly Pro Tyr Ala Ser Ala Ala Ala Ala Gly Thr Tyr Gly
            180                 185                 190

Ser Gly Pro Gly Ile Phe Gly Pro Tyr Gly Pro Gly Thr Ser Gly Ser
            195                 200                 205

Gly Ile Phe Gly Pro Gly Ile Phe Gly Pro Tyr Ala Ser Ala Ala Ala
            210                 215                 220

Ala Ala Gly Pro Gly Ile Phe Gly Pro Tyr Gly Pro Gly Ser Ser Ala
225                 230                 235                 240

Ala Ala Ala Gly Thr Tyr Gly Tyr Gly Pro Gly Ile Phe Gly Pro
            245                 250                 255

Tyr Gly Pro Gly Ala Ser Gly Thr Gly Pro Gly Ser Gly Thr Tyr Gly
            260                 265                 270

Pro Gly Ile Phe Gly Pro Gly Thr Ser Ala Ala Ala Ala Gly Pro
            275                 280                 285

Gly Ile Phe Gly Pro Tyr Gly Pro Gly Ala Ser Ala Ala Ala Ala
            290                 295                 300

Gly Thr Tyr Gly Pro Gly Ile Phe Gly Pro Gly Thr Tyr Gly Pro Gly
305                 310                 315                 320

Ser Ser Gly Pro Gly Ile Phe Gly Pro Tyr Gly Pro Gly Ser Ser Ala
            325                 330                 335

Ala Ala Ala Gly Thr Tyr Gly Pro Gly Ile Phe Gly Pro Tyr Gly
            340                 345                 350

Pro Gly Thr Ser Ala Ala Ala Ala Gly Thr Tyr Ile Phe Gly Pro
            355                 360                 365

Gly Ile Phe Gly Pro Tyr Gly Pro Gly Ala Ser Gly Pro Gly Ile Phe
            370                 375                 380

Gly Pro Tyr Gly Pro Gly Ala Ser Ala Ala Ala Ala Gly Pro Gly
385                 390                 395                 400

Thr Tyr Gly Pro Gly Ile Phe Gly Pro Ser Ala Ser Ala Ala Ala
            405                 410                 415

Ala Gly Thr Tyr Gly Ser Gly Pro Gly Thr Tyr Gly Pro Tyr Gly Pro
            420                 425                 430

Gly Thr Ser Gly Pro Gly Ser Gly Ile Phe Gly Thr Gly Pro Tyr Gly
            435                 440                 445

Pro Gly Ala Ser Ala Ala Ala Ala Gly Thr Tyr Gly Pro Gly Ile
            450                 455                 460

Phe Gly Pro Tyr Gly Pro Gly Thr Ser Ala Ala Ala Ala Ala Gly Pro
```

-continued

```
        465                 470                 475                 480
Gly Ser Gly Thr Tyr Gly Pro Gly Ala Ser Gly Thr Gly Pro Gly Ser
                485                 490                 495

Gly Thr Tyr Gly Pro Gly Ile Phe Gly Pro Gly Thr Ser Ala Ala Ala
                500                 505                 510

Ala Ala Gly Thr Tyr Ile Phe Gly Pro Gly Ile Phe Gly Pro Tyr Gly
                515                 520                 525

Pro Gly Ala Ser Ala Ala Ala Ala Gly Thr Tyr Gly Ser Gly Pro
530                 535                 540

Gly Ile Phe Gly Pro Tyr Gly Pro Gly Thr Ser Gly Ser Gly Ile Phe
545                 550                 555                 560

Gly Pro Gly Ile Phe Gly Pro Tyr Ala Ser Ala Ala Ala Ala Gly
                565                 570                 575

Pro Gly Ser Gly Ile Phe Gly Pro Gly Ala Ser
                580                 585

<210> SEQ ID NO 43
<211> LENGTH: 601
<212> TYPE: PRT
<213> ORGANISM: Artificial Sequence
<220> FEATURE:
<223> OTHER INFORMATION: PRT917

<400> SEQUENCE: 43

Met His His His His His Ser Ser Gly Ser Ser Gly Pro Gly Leu
1               5                   10                  15

Ile Gly Pro Tyr Gly Pro Gly Ala Ser Ala Ala Ala Ala Gly Val
                20                  25                  30

Asn Gly Pro Gly Ser Gly Leu Ile Gly Pro Gly Val Ser Gly Val Tyr
                35                  40                  45

Gly Pro Gly Leu Ile Gly Pro Gly Leu Ile Gly Pro Gly Ser Ser Ala
                50                  55                  60

Ala Ala Ala Gly Pro Gly Val Tyr Gly Pro Gly Leu Ile Gly Pro
65                  70                  75                  80

Ser Ala Ser Ala Ala Ala Ala Gly Pro Gly Ser Gly Leu Ile Gly
                85                  90                  95

Pro Gly Ala Ser Gly Val Tyr Gly Pro Gly Leu Ile Gly Pro Gly Leu
                100                 105                 110

Ile Gly Pro Gly Ser Ser Ala Ala Ala Ala Gly Val Tyr Gly Ser
                115                 120                 125

Gly Pro Gly Leu Ile Gly Pro Tyr Gly Ser Ala Ala Ala Ala Gly
                130                 135                 140

Pro Gly Ser Gly Val Tyr Gly Val Gly Pro Tyr Gly Pro Gly Ala Ser
145                 150                 155                 160

Gly Pro Gly Val Tyr Gly Pro Gly Leu Ile Gly Pro Ser Ala Ser Ala
                165                 170                 175

Ala Ala Ala Gly Ser Gly Leu Ile Gly Pro Gly Val Tyr Gly Pro
                180                 185                 190

Tyr Ala Ser Ala Ala Ala Ala Gly Val Tyr Gly Ser Gly Pro Gly
                195                 200                 205

Leu Ile Gly Pro Tyr Gly Pro Gly Val Ser Gly Ser Gly Leu Ile Gly
                210                 215                 220

Pro Gly Leu Ile Gly Pro Tyr Ala Ser Ala Ala Ala Ala Gly Pro
225                 230                 235                 240

Gly Leu Ile Gly Pro Tyr Gly Pro Gly Ser Ser Ala Ala Ala Ala Ala
```

245                 250                 255
Gly Val Tyr Gly Tyr Gly Pro Gly Leu Ile Gly Pro Tyr Gly Pro Gly
                    260                 265                 270
Ala Ser Gly Val Asn Gly Pro Gly Ser Gly Val Tyr Gly Pro Gly Leu
                275                 280                 285
Ile Gly Pro Gly Val Ser Ala Ala Ala Ala Gly Pro Gly Leu Ile
            290                 295                 300
Gly Pro Tyr Gly Pro Gly Ala Ser Ala Ala Ala Ala Gly Val Tyr
305                 310                 315                 320
Gly Pro Gly Leu Ile Gly Pro Gly Val Tyr Gly Pro Gly Ser Ser Gly
                325                 330                 335
Pro Gly Leu Ile Gly Pro Tyr Gly Pro Gly Ser Ser Ala Ala Ala
            340                 345                 350
Ala Gly Val Tyr Gly Pro Gly Leu Ile Gly Pro Tyr Gly Pro Gly Val
                355                 360                 365
Ser Ala Ala Ala Ala Gly Val Tyr Leu Ile Gly Pro Gly Leu Ile
370                 375                 380
Gly Pro Tyr Gly Pro Gly Ala Ser Gly Pro Gly Leu Ile Gly Pro Tyr
385                 390                 395                 400
Gly Pro Gly Ala Ser Ala Ala Ala Ala Gly Pro Gly Val Tyr Gly
                405                 410                 415
Pro Gly Leu Ile Gly Pro Ser Ala Ser Ala Ala Ala Ala Gly Val
                420                 425                 430
Tyr Gly Ser Gly Pro Gly Val Tyr Gly Pro Tyr Gly Pro Gly Val Ser
                435                 440                 445
Gly Pro Gly Ser Gly Leu Ile Gly Val Gly Pro Tyr Gly Pro Gly Ala
            450                 455                 460
Ser Ala Ala Ala Ala Gly Val Tyr Gly Pro Gly Leu Ile Gly Pro
465                 470                 475                 480
Tyr Gly Pro Gly Val Ser Ala Ala Ala Ala Gly Pro Gly Ser Gly
                485                 490                 495
Val Tyr Gly Pro Gly Ala Ser Gly Val Asn Gly Pro Gly Ser Gly Val
                500                 505                 510
Tyr Gly Pro Gly Leu Ile Gly Pro Gly Val Ser Ala Ala Ala Ala
            515                 520                 525
Gly Val Tyr Leu Ile Gly Pro Gly Leu Ile Gly Pro Tyr Gly Pro Gly
            530                 535                 540
Ala Ser Ala Ala Ala Ala Gly Val Tyr Gly Ser Gly Pro Gly Leu
545                 550                 555                 560
Ile Gly Pro Tyr Gly Pro Gly Val Ser Gly Ser Gly Leu Ile Gly Pro
                565                 570                 575
Gly Leu Ile Gly Pro Tyr Ala Ser Ala Ala Ala Ala Gly Pro Gly
            580                 585                 590
Ser Gly Leu Ile Gly Pro Gly Ala Ser
            595                 600

<210> SEQ ID NO 44
<211> LENGTH: 598
<212> TYPE: PRT
<213> ORGANISM: Artificial Sequence
<220> FEATURE:
<223> OTHER INFORMATION: PRT1028

<400> SEQUENCE: 44

Met His His His His His His Ser Ser Gly Ser Ser Gly Pro Gly Ile

-continued

```
1               5                   10                  15
Phe Gly Pro Tyr Gly Pro Gly Ala Ser Ala Ala Ala Gly Thr
                20                  25                  30
Gly Pro Gly Ser Gly Ile Phe Gly Pro Gly Thr Ser Gly Tyr Gly
                35                  40                  45
Pro Gly Ile Phe Gly Pro Gly Ile Phe Gly Pro Gly Ser Ser Ala Ala
                50                  55                  60
Ala Ala Ala Gly Pro Gly Thr Tyr Gly Pro Gly Ile Phe Gly Pro Ser
65                  70                  75                  80
Ala Ser Ala Ala Ala Ala Ala Gly Pro Gly Ser Gly Ile Phe Gly Pro
                85                  90                  95
Gly Ala Ser Gly Thr Tyr Gly Pro Gly Ile Phe Gly Pro Gly Ile Phe
                100                 105                 110
Gly Pro Gly Ser Ser Ala Ala Ala Ala Gly Thr Tyr Gly Ser Gly
                115                 120                 125
Pro Gly Ile Phe Gly Pro Tyr Gly Ser Ala Ala Ala Ala Gly Pro
                130                 135                 140
Gly Ser Gly Thr Tyr Gly Thr Gly Pro Tyr Gly Pro Gly Ala Ser Gly
145                 150                 155                 160
Pro Gly Thr Tyr Gly Pro Gly Ile Phe Gly Pro Ser Ala Ser Ala Ala
                165                 170                 175
Ala Ala Ala Gly Ser Gly Ile Phe Gly Pro Gly Thr Tyr Gly Pro Tyr
                180                 185                 190
Ala Ser Ala Ala Ala Ala Gly Thr Tyr Gly Ser Gly Pro Gly Ile
                195                 200                 205
Phe Gly Pro Tyr Gly Pro Gly Thr Ser Gly Ser Gly Ile Phe Gly Pro
                210                 215                 220
Gly Ile Phe Gly Pro Tyr Ala Ser Ala Ala Ala Ala Gly Pro Gly
225                 230                 235                 240
Ile Phe Gly Pro Tyr Gly Pro Gly Ser Ser Ala Ala Ala Ala Gly
                245                 250                 255
Thr Tyr Gly Tyr Gly Pro Gly Ile Phe Gly Pro Tyr Gly Pro Gly Ala
                260                 265                 270
Ser Gly Thr Gly Pro Gly Ser Gly Thr Tyr Gly Pro Gly Ile Phe Gly
                275                 280                 285
Pro Gly Thr Ser Ala Ala Ala Ala Gly Pro Gly Ile Phe Gly Pro
                290                 295                 300
Tyr Gly Pro Gly Ala Ser Ala Ala Ala Ala Gly Thr Tyr Gly Pro
305                 310                 315                 320
Gly Ile Phe Gly Pro Gly Thr Tyr Gly Pro Gly Ser Ser Gly Pro Gly
                325                 330                 335
Ile Phe Gly Pro Tyr Gly Pro Gly Ser Ser Ala Ala Ala Ala Gly
                340                 345                 350
Thr Tyr Gly Pro Gly Ile Phe Gly Pro Tyr Gly Pro Gly Thr Ser Ala
                355                 360                 365
Ala Ala Ala Gly Thr Tyr Ile Phe Gly Pro Gly Ile Phe Gly Pro
                370                 375                 380
Tyr Gly Pro Gly Ala Ser Gly Pro Gly Ile Phe Gly Pro Tyr Gly Pro
385                 390                 395                 400
Gly Ala Ser Ala Ala Ala Ala Gly Pro Gly Thr Tyr Gly Pro Gly
                405                 410                 415
Ile Phe Gly Pro Ser Ala Ser Ala Ala Ala Ala Gly Thr Tyr Gly
                420                 425                 430
```

-continued

```
Ser Gly Pro Gly Thr Tyr Gly Pro Tyr Gly Pro Gly Thr Ser Gly Pro
        435                 440                 445

Gly Ser Gly Ile Phe Gly Thr Gly Pro Tyr Gly Pro Gly Ala Ser Ala
    450                 455                 460

Ala Ala Ala Ala Gly Thr Tyr Gly Pro Gly Ile Phe Gly Pro Tyr Gly
465                 470                 475                 480

Pro Gly Thr Ser Ala Ala Ala Ala Gly Pro Gly Ser Gly Thr Tyr
            485                 490                 495

Gly Pro Gly Ala Ser Gly Thr Gly Pro Gly Ser Gly Thr Tyr Gly Pro
            500                 505                 510

Gly Ile Phe Gly Pro Gly Thr Ser Ala Ala Ala Ala Gly Thr Tyr
        515                 520                 525

Ile Phe Gly Pro Gly Ile Phe Gly Pro Tyr Gly Pro Gly Ala Ser Ala
        530                 535                 540

Ala Ala Ala Ala Gly Thr Tyr Gly Ser Gly Pro Gly Ile Phe Gly Pro
545                 550                 555                 560

Tyr Gly Pro Gly Thr Ser Gly Ser Gly Ile Phe Gly Pro Gly Ile Phe
                565                 570                 575

Gly Pro Tyr Ala Ser Ala Ala Ala Ala Gly Pro Gly Ser Gly Ile
            580                 585                 590

Phe Gly Pro Gly Ala Ser
        595
```